US009937157B2

(12) United States Patent
Taneja et al.

(10) Patent No.: US 9,937,157 B2
(45) Date of Patent: *Apr. 10, 2018

(54) MODIFIED RELEASE DOSAGE FORMS OF XANTHINE OXIDOREDUCTASE INHIBITOR OR XANTHINE OXIDASE INHIBITORS

(71) Applicant: Takeda Pharmaceuticals U.S.A., Inc., Deerfield, IL (US)

(72) Inventors: Rajneesh Taneja, Libertyville, IL (US); Vijay Gupte, Vernon Hills, IL (US); Majid Vakilynejad, Pleasant Prairie, WI (US)

(73) Assignee: Takeda Pharmaceuticals U.S.A., Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/010,212

(22) Filed: Jan. 29, 2016

(65) Prior Publication Data

US 2016/0317505 A1 Nov. 3, 2016

Related U.S. Application Data

(63) Continuation of application No. 13/160,572, filed on Jun. 15, 2011, now Pat. No. 9,248,119.

(60) Provisional application No. 61/355,164, filed on Jun. 16, 2010.

(51) Int. Cl.
| *A61K 31/426* | (2006.01) |
| *A61K 9/00* | (2006.01) |
| *A61K 9/28* | (2006.01) |
| *A61K 9/20* | (2006.01) |
| *A61K 9/50* | (2006.01) |
| *A61K 9/16* | (2006.01) |
| *A61K 9/24* | (2006.01) |

(52) U.S. Cl.
CPC .......... *A61K 31/426* (2013.01); *A61K 9/0004* (2013.01); *A61K 9/0053* (2013.01); *A61K 9/1629* (2013.01); *A61K 9/2027* (2013.01); *A61K 9/2054* (2013.01); *A61K 9/2833* (2013.01); *A61K 9/5084* (2013.01); *A61K 9/209* (2013.01); *A61K 9/5026* (2013.01); *A61K 9/5047* (2013.01); *A61K 9/5078* (2013.01)

(58) Field of Classification Search
CPC .. A61K 31/426; A61K 9/0004; A61K 9/2027; A61K 9/2054; A61K 9/209; A61K 9/5026; A61K 9/5047; A61K 9/5078; A61K 9/5084; A61K 9/0053; A61K 9/1629; A61K 9/2833; H04W 16/18; H04W 24/10
See application file for complete search history.

(56) References Cited

U.S. PATENT DOCUMENTS

| 5,614,520 | A | 3/1997 | Kondo et al. |
| 6,730,325 | B2 | 5/2004 | Devane |
| 2006/0252808 | A1 | 11/2006 | Joseph-Ridge |
| 2008/0299197 | A1* | 12/2008 | Toneguzzo ............ A61K 9/209 424/473 |
| 2009/0022807 | A1 | 1/2009 | Li |
| 2009/0053308 | A1* | 2/2009 | Ishida .................. A61K 9/4816 424/461 |

FOREIGN PATENT DOCUMENTS

| CN | 1713897 A | 12/2005 |
| CN | 101474175 | 7/2009 |
| CN | 101658505 | 3/2010 |
| CN | 101711743 | 5/2010 |
| CN | 101711751 | 5/2010 |
| CN | 101773498 | 7/2010 |
| EC | SP-99-3280 | 1/2001 |
| EP | 0779074 | 6/1997 |
| WO | WO 00/23055 | 4/2000 |
| WO | WO 00/25752 | 5/2000 |
| WO | WO 2004/024128 | 3/2004 |
| WO | WO 2004/035020 A2 | 4/2004 |
| WO | WO 2006/056711 | 6/2006 |
| WO | WO 2007/036671 | 4/2007 |
| WO | WO 2007/040997 | 4/2007 |
| WO | WO 2008/064015 A1 | 5/2008 |
| WO | WO 2009/143020 A1 | 11/2009 |
| WO | WO 2011/162390 | 12/2011 |
| WO | WO 2012/005365 | 1/2012 |

OTHER PUBLICATIONS

European Patent Office Action Search Report for Application No. 11796331 dated Nov. 7, 2013.
Notice of Opposition for Ecuadorian Patent Application No. SP2013-12394 by Asociacion de Laboratorios Farmaceuticos (ALAFAR) dated Apr. 23, 2014 (with translation).
Notice of Opposition for Chilean Patent Application No. 3548-2012 by Asociacion Industrial de Laboratorios Farmaceuticos AG (ASILFA) dated Aug. 12, 2014 (with translation).
Notice of Opposition for Chilean Patent Application No. 3548-2012 by Laboratorios Recalcine S.A. dated Aug. 12, 2014 (with translation).
Technical Information on Eudragit, EUDRAGIT® L100 and EUDRAGIT® S100 (an Evonik product, Evonik Industries AG, pp. 1-7, Dec. 2012).
Sigma-Aldrich Sigma-Aldrich Allopurinol product information, pp. 1-2, 2013.
Beara-Lasic et al., "Advances in the management of gout: critical appraisalof febuxostat in the control of hyperuricemia," Int. J. Neph. Renovasc. Dis., 2010, 3:1-10.

(Continued)

*Primary Examiner* — Snigdha Maewall
(74) *Attorney, Agent, or Firm* — Foley & Lardner LLP

(57) ABSTRACT

The present disclosure relates to novel dosage forms of xanthine oxidoreductase inhibitors.

20 Claims, 12 Drawing Sheets

(56) References Cited

OTHER PUBLICATIONS

Becker et al., "Febuxostat (TMX-67) a novel, non-purine, selective inhibitor of xanthine oxidase, is safe and decreases serum urate in healthy volunteers," Neucleosides, Nucleotides & Nucleic Acids, 2004, 23(8-9):1111-1116.
Notice of Opposition for Colombian Application No. 12-227085 by Laboratorio Franco Colombiano S.A. dated Jul. 15, 2013 (with translation).
Notice of Opposition for Peruvian Application No. 2433-2012 by Unimed del Peru S.A. dated Aug. 27, 2013 (with translation).
Notice of Opposition for Peruvian Application No. 2433-2012 by Farmindustria S.A. dated Aug. 27, 2013 (with translation).
Khosravan et al., "Pharmacokinetics, pharmacodynamics and safety of febuxostat, a non-purine selective inhibitor of xanthine oxidase, in a dose escalation study in healthy subjects," TAP Pharmaceutical Products, Inc., Lake Forest, Illinois, United States, Clinical Pharmacokinetics, 2006, 45(8):821-841; abstract.
Fukunari et al., "Y-700 [1-[3-Cyano-4-(2,2-dimethylproproxy)phenyl]-1H-pyrazole-4-carboxylic acid]; a potent xanthine oxidoreductase inhibitor with hepatic excretion," J. Pharmacol. Exp. Ther., 2004, 311(2):519-528.
Breithaupt et al., "Kinetics of allopurinol after single intravenous and oral doses. Noninteraction with benzbromarone and hydrochlorothiazide," European Journal of Clinical Pharmacology, 1982, 22(1):77-84; abstract.
Becker et al., "Febuxostat, a novel nonpurine selective inhibitor of xanthine oxidase," Arthritis & Rheumatism, 2005, 52(3):916-923.
Guerra et al., "Bioequivalence of allopurinol and its metabolite oxipurinol in two tablet formulations," Journal of Clinical Pharmacy and Therapeutics, 2001, 26:113-119; abstract.
Graham et al., "Pharmacodynamics of oxypurinol after administration of allopurinol to healthy subjects," Br. J. Clin. Pharmacol., 1996, 41:299-304; abstract.
Mayer et al., "Pharmacokinetics and pharmacodynamics of febuxostat, a new non-purine selective inhibitor of xanthine oxidase in subjects with renal impairment," American Journal of Therapeutics, 2005, 12:22-34; abstract.
International Search Report from International Patent Application Publication No. WO 2011/159745, dated Oct. 25, 2011.
Written Opinion from International Patent Application No. PCT/US2011/040418 dated Oct. 25, 2011, 10 pages.
Dey et al., "Multiparticulate Drug Delivery Systems for Controlled Release," Tropical Journal of Pharmaceutical Research, Sep. 2008, 7(3)1067-1075.

\* cited by examiner

MEAN PLASMA CONCENTRATIONS OF FEBUXOSTAT (LINEAR TOP AND LOG-LINEAR BOTTOM) FOLLOWING ADMINISTRATION OF A SINGLE ORAL DOSE OF 80 mg FEBUXOSTAT RELEASED IN VARIOUS LOCATIONS THE GI TRACT IN 12 SUBJECTS

ESTIMATED PLASMA PROFILE FOR A 3-PULSE 80 mg DOSE OF FEBUXOSTAT, PULSE 1 (D*0.3, t=0) IMMEDIATE RELEASE + PULSE 2 (D*0.3, t=5 h) 5 HOUR DELAYED RELEASE + PULSE 3 (D*0.45*0.4, t=10 h) 10 HOUR DELAYED RELEASE.

ESTIMATED PLASMA PROFILE FOR A 2 PULSE 80 mg DOSE OF FEBUXOSTAT, PULSE 1 (D*0.2, t=0) IMMEDIATE RELEASE + PULSE 2 (D*0.75, t=5 h) 5 HOUR RELEASE + 5% DOSE RELEASE IN COLON (D*0.45*0.05, t= 10 h)

ESTIMATED PLASMA PROFILE FOR AN 80 mg EXTENDED RELEASE (ER) FORMULATION OF FEBUXOSTAT, WHEREIN 90% OF ABSORPTION COMPLETED IN 6 HOURS WITH Ka=0.462 h$^{-1}$, AND 10% OF DOSE WAS ABSORBED FROM THE COLON WITH FREL=0.45.

Fig. 5
FEBUXOSTAT MODIFIED RELEASE MATRIX TABLET FORMULATIONS

| FORMULATION | A1 | B1 | C1 | D1 | E1 | F1 | G1 | H1 |
|---|---|---|---|---|---|---|---|---|
| FEBUXOSTAT % | 16.7 | 16.7 | 16.7 | 16.7 | 16.7 | 16.7 | 16.7 | 16.7 |
| HYPROMELLOSE K100LV % | 30.0 | 30.0 | 15.0 | 15.0 | 30.0 | 15.0 | 15.0 | 30.0 |
| AVICEL PH 101 % | 34.7 | 11.6 | 50.5 | 15.3 | 13.1 | 16.8 | 46.0 | 39.2 |
| EUDRAGIT EPO % | 6.0 | 6.0 | 0 | 6.0 | 0.0 | 0.0 | 6.0 | 0.0 |
| LACTOSE % | 11.6 | 34.7 | 16.8 | 46.0 | 39.2 | 50.5 | 15.3 | 13.1 |
| MG STEARATE | 1.0 | 1.0 | 1.0 | 1.0 | 1.0 | 1.0 | 1.0 | 1.0 |

DISSOLUTION PROFILES OF FEBUXOSTAT MODIFIED RELEASE MATRIX TABLETS (50 mg) IN pH 6.8, 0.5M PHOSPHATE BUFFER

PLASMA CONCENTRATION VERSUS TIME PROFILES IN DOGS FOR THE FEBUXOSTAT FORMULATIONS DESCRIBED IN EXAMPLE 10

Extended-Release Formulation B

|      | Tmax(a) (hr) | Cmax (ng/mL) | AUC(0-tlqc) ng.hr/mL) | AUC(0-inf) ng.hr/mL) | T1/2 (h) | CL/F (L/hr) | Vz/F (L) |
|------|--------------|--------------|-----------------------|----------------------|----------|-------------|----------|
| N    | 34           | 34           | 34                    | 27                   | 27       | 27          | 27       |
| Mean | 3.0          | 1186.6       | 6749.3                | 7133.2               | 9.7      | 12.52       | 171.1    |
| SD   | 0.5-6.0      | 407.31       | 2198.84               | 2497.88              | 3.65     | 4.333       | 78.2     |
| %CV  | -            | 34           | 33                    | 35                   | 38       | 35          | 46       |

MODIFIED RELEASE DOSAGE FORMS OF XANTHINE OXIDOREDUCTASE INHIBITOR OR XANTHINE OXIDASE INHIBITORS

RELATED APPLICATION INFORMATION

This application is a Continuation of U.S. application Ser. No. 13/160,572, filed Jun. 15, 2011, which issued as U.S. Pat. No. 9,248,119, on Feb. 2, 2016, and which claims priority to U.S. Provisional Application No. 61/355,164 filed on Jun. 16, 2010, the contents of which are herein incorporated by reference in their entirety.

FIELD OF THE INVENTION

The present disclosure relates to novel dosage forms comprising at least one xanthine oxidoreductase inhibitor or xanthine oxidase inhibitor. In addition, the present disclosure also relates to methods of treating certain diseases using the novel dosage forms of the present disclosure.

BACKGROUND OF THE INVENTION

2-[3-cyano-4-(2-methylpropoxy)phenyl]-4-methylthiazole-5-carboxylic acid (also known as "febuxostat" and "TMX-67") is a potent, non-purine selective inhibitor of xanthine oxidoreductase. Febuxostat 40 and 80 mg once daily (QD) is approved in the United States for the chronic management of hyperuricemia in patients with gout. Gout is a disease that results from the deposition of urate crystals in synovial fluid and other tissues when there is an oversaturation of urate in the blood. Febuxostat is a potent selective inhibitor of the xanthine oxidoreductase enzyme (or xanthine oxidoreductase inhibitor) that is required for the synthesis of uric acid.

The xanthine oxidoreductase enzyme can be present in two different forms (See, Enroth C, et al., "Crystal structures of bovine milk xanthine dehydrogenase A and xanthine oxidase: structure-based mechanism of conversion," *Proc. Natl. Acad. Sci. USA*, 97(20):10723-8 (Sep. 26, 2000)). In one form, the xanthine oxidoreductase enzyme is synthesized as xanthine dehydrogenase. This form of the enzyme exhibits a very low reactivity with oxygen. However, under stress or disease conditions, such as ischemia reperfusion injury and congestive heart failure, xanthine dehydrogenase can undergo the formation of intramolecular disulfide bonds or proteolytic cleavage, which converts the enzyme to the second form, xanthine oxidase. Xanthine oxidase exhibits a high reactivity with oxygen. Therefore, the synthesis of uric acid from xanthine and hypoxanthine by the xanthine oxidoreductase enzyme in the form of xanthine oxidase is associated with the generation of oxygen free radicals, such as superoxide anion and hydrogen peroxide. These free radicals are capable of causing a variety of toxic activities in the body such as inactivation of proteins, DNA breakdown, lipid peroxidation (which causes cell membrane disruption) and increasing pro-inflammatory cytokines.

A number of disease conditions are associated with elevated xanthine oxidoreductase activity, especially, elevated xanthine oxidase activity. Such diseases include, but are not limited to, hyperuricemia, hypertension, metabolic syndrome, diabetes, myocardial ischemia, atherosclerosis, stroke, congestive heart failure, inflammatory bowel disease, renal disease progression, prostatitis, sleep apnea and autoimmune diseases. Hyperuricemia is also associated with a number of disease conditions, such as renal injury and hypertension.

Allopurinol is used in the treatment of hyperuricemia. Allopurinol has been shown to prevent the renal injury and hypertension associated with hyperuricemia by inhibiting xanthine oxidoreductase, thus reducing uric acid levels. In contrast, it has been found that the extent of protection against renal injury and hypertension in subjects suffering hyperuricemia is lower in subjects treated with the uricosuric agent benziodarone. Benziodarone does not inhibit xanthine oxidoreductase activity, but instead reduces plasma uric acid levels by increasing the excretion of uric acid in the kidney (See, Mazzali M, et al., "Elevated uric acid increases blood pressure in the rat by a novel crystal-independent mechanism," *Hypertension*, 38:1101-1106 (2001) and Mazzali M, et al., "Hyperuricemia induces a primary renal arteriolopathy in rats by a blood pressure-independent mechanism," *Am. J. Physiol Renal Physiol.*, 282:F991-F997 (2002)). Therefore, there is a need in the art for new dosage forms that not only reduce uric acid levels in subjects suffering hyperuricemia, but are also capable of maintaining a high level of (namely, at least 80%) inhibition of xanthine oxidoreductase activity in a subject in order to protect subjects receiving these dosage forms throughout their treatment regimen (i.e., dosing interval which is typically twenty-four hours) against increasing concentrations of oxygen free radicals.

As referenced above, another treatment for hyperuricemia is with the compound febuxostat. Extensive pharmacokinetic and pharmacodynamic data have established that maintaining a concentration of febuxostat in plasma over a prolonged period of time provides similar efficacy to treatment with high doses of the drug. Generally, these studies have shown that maintaining a febuxostat plasma concentration of 100 ng/ml is required to provide 95% or greater inhibition of xanthine oxidase. Currently, there the only commercially available formulations of febuxostat are immediate release formulations. There are no currently commercially available extended or delayed release formulations of febuxostat. Therefore, a formulation of febuxostat that maintains the drug concentration above the critical concentration of 100 ng/ml for an extended period of time is expected to result in higher efficacy of the drug, and would be a desirable treatment option for the control of hyperuricemia, gout, and many other disease states.

SUMMARY OF THE INVENTION

In one embodiment, the present disclosure relates to modified release dosage forms. The modified release dosage forms can comprise at least one xanthine oxidoreductase inhibitor or at least one xanthine oxidase inhibitor.

In another embodiment, the modified release dosage forms of the present disclosure comprise: a xanthine oxidoreductase inhibitor or a pharmaceutically acceptable salt thereof, wherein said dosage form, after oral administration to a subject in need of treatment thereof exhibits at least one of the following:

(a) maintains in the subject a plasma concentration of xanthine oxidoreductase inhibitor or pharmaceutically acceptable salt thereof greater than about 0.1 μg/mL for a period of from about 5 hours to about 24 hours; and (b) produces in the subject a maximum plasma concentration ($C_{max}$) of a xanthine oxidoreductase inhibitor or a pharmaceutically acceptable salt thereof in an amount between about 2.5 μg/mL to about 0.5 μg/mL.

Alternatively, the modified release dosage form, after oral administration to a subject in need of treatment thereof, exhibits the following:

(a) maintains in the subject a plasma concentration of xanthine oxidoreductase inhibitor or pharmaceutically acceptable salt thereof greater than about 0.1 µg/mL for a period of from about 5 hours to about 24 hours; and (b) produces in the subject a maximum plasma concentration ($C_{max}$) of a xanthine oxidoreductase inhibitor or a pharmaceutically acceptable salt thereof of between about 2.0 µg/mL to about 1.0 µg/mL.

Still further alternatively, the modified release dosage form, after oral administration to a subject in need of treatment thereof, can exhibit each of the following:

(a) maintains in the subject a plasma concentration of xanthine oxidoreductase inhibitor or pharmaceutically acceptable salt thereof greater than about 0.1 µg/mL for a period of from about 5 hours to about 24 hours; and (b) produces in the subject a maximum plasma concentration ($C_{max}$) of a xanthine oxidoreductase inhibitor or a pharmaceutically acceptable salt thereof of between about 2.5 µg/mL to about 0.5 µg/mL.

In one aspect, the modified release dosage forms of the present disclosure can contain from about 5 to about 240 mg of at least one xanthine oxidoreductase inhibitor or a pharmaceutically acceptable salt thereof. In another aspect, the the modified release dosage forms of the present disclosure can contain from about 40 to about 240 mg of at least one xanthine oxidoreductase inhibitor or a pharmaceutically acceptable salt thereof When administered orally to a subject in need of treatment thereof, the modified release dosage forms of the present disclosure can produce in the subject a $C_{max}$ of a xanthine oxidoreductase inhibitor or a pharmaceutically acceptable salt thereof in an amount of about 2.5 µg/mL, about 2.4 µg/mL, about 2.3 µg/mL, about 2.2 µg/mL, about 2.1 µg/mL, 2.0 µg/mL about 1.9 µg/mL, about 1.8 µg/mL, about 1.7 µg/mL, about 1.6 µg/mL, about 1.5 µg/mL, about 1.4 µg/mL, about 1.3 µg/mL, about 1.2 µg/mL, about 1.1 µg/mL, about 1.0 µg/mL, about 0.9 µg/mL, about 0.8 µg/mL, about 0.7 µg/mL, about 0.6 µg/mL or about 0.5 µg/mL. Specifically, the modified release dosage forms of the present disclosure, when administered orally to a subject in need of treatment thereof, can produce in that subject a $C_{max}$ of a xanthine oxidoreductase inhibitor or a pharmaceutically acceptable salt thereof in a range of about 2.5 µg/mL to about 1.0 µg/mL. Even more specifically, the modified release dosage forms of the present disclosure, when administered orally to a subject in need of treatment thereof, can produce in that subject a $C_{max}$ of a xanthine oxidoreductase inhibitor or a pharmaceutically acceptable salt thereof in a range of about 2.0 µg/mL to about 1.5 µg/mL.

In yet another embodiment, the modified release dosage forms of the present disclosure comprise: a xanthine oxidoreductase inhibitor or a pharmaceutically acceptable salt thereof, wherein said dosage form, after oral administration to a subject in need of treatment thereof exhibits at least one of the following:

(a) maintains in the subject a plasma concentration of xanthine oxidoreductase inhibitor or pharmaceutically acceptable salt thereof greater than about 0.1 µg/mL for a period of from about 5 hours to about 16 hours; and (b) produces in the subject a maximum plasma concentration ($C_{max}$) of a xanthine oxidoreductase inhibitor or a pharmaceutically acceptable salt thereof in an amount between about 2.5 µg/mL to about 0.050 µg/mL.

Alternatively, the modified release dosage form, after oral administration to a subject in need of treatment thereof, exhibits the following:

(a) maintains in the subject a plasma concentration of xanthine oxidoreductase inhibitor or pharmaceutically acceptable salt thereof greater than about 0.1 µg/mL for a period of from about 5 hours to about 16 hours; and (b) produces in the subject a maximum plasma concentration ($C_{max}$) of a xanthine oxidoreductase inhibitor or a pharmaceutically acceptable salt thereof of between about 2.0 µg/mL to about 0.075 µg/mL.

Still further alternatively, the modified release dosage form, after oral administration to a subject in need of treatment thereof, can exhibit each of the following:

(a) maintains in the subject a plasma concentration of xanthine oxidoreductase inhibitor or pharmaceutically acceptable salt thereof greater than about 0.1 µg/mL for a period of from about 5 hours to about 16 hours; and (b) produces in the subject a maximum plasma concentration ($C_{max}$) of a xanthine oxidoreductase inhibitor or a pharmaceutically acceptable salt thereof of between about 2.5 µg/mL to about 0.050 µg/mL.

The modified release dosage forms of the present disclosure can contain from about 40 to about 240 mg of at least one xanthine oxidoreductase inhibitor or a pharmaceutically acceptable salt thereof.

When administered orally to a subject in need of treatment thereof, the modified release dosage forms of the present disclosure can produce in the subject a $C_{max}$ of a xanthine oxidoreductase inhibitor or a pharmaceutically acceptable salt thereof in an amount of about 2.5 µg/mL, about 2.4 µg/mL, about 2.3 µg/mL, about 2.2 µg/mL, about 2.1 µg/mL, 2.0 µg/mL about 1.9 µg/mL, about 1.8 µg/mL, about 1.7 µg/mL, about 1.6 µg/mL, about 1.5 µg/mL, about 1.4 µg/mL, about 1.3 µg/mL, about 1.2 µg/mL, about 1.1 µg/mL, about 1.0 µg/mL, about 0.9 µg/mL, about 0.8 µg/mL, about 0.7 µg/mL, about 0.6 µg/mL, about 0.5 µg/mL, about 0.4 µg/mL, about 0.3 µg/mL, about 0.2 µg/mL, about 0.1 µg/mL, about 0.099 µg/mL, about 0.098 µg/mL, about 0.097 µg/mL, about 0.096 µg/mL, about 0.095 µg/mL, about 0.094 µg/mL, about 0.093 µg/mL, about 0.092 µg/mL, about 0.091 µg/mL, about 0.090 µg/mL, about 0.089 µg/mL, about 0.088 µg/mL, about 0.087 µg/mL, about 0.086 µg/mL, about 0.085 µg/mL, about 0.084 µg/mL, about 0.083 µg/mL, about 0.082 µg/mL, about 0.081 µg/mL, about 0.080 µg/mL, about 0.079 µg/mL, about 0.078 µg/mL, about 0.077 µg/mL, about 0.076 µg/mL, about 0.075 µg/mL, about 0.074 µg/mL, about 0.073 µg/mL, about 0.072 µg/mL, about 0.071 µg/mL, about 0.070 µg/mL, about 0.069 µg/mL, about 0.068 µg/mL, about 0.067 µg/mL, about 0.066 µg/mL, about 0.065 µg/mL, about 0.064 µg/mL, about 0.063 µg/mL, about 0.062 µg/mL, about 0.061 µg/mL, about 0.060 µg/mL, about 0.059 µg/mL, about 0.058 µg/mL, about 0.057 µg/mL, about 0.056 µg/mL, about 0.055 µg/mL, about 0.054 µg/mL, about 0.053 µg/mL, about 0.052 µg/mL, about 0.051 µg/mL or about 0.050 µg/mL. Specifically, the modified release dosage forms of the present disclosure, when administered orally to a subject in need of treatment thereof, can produce in that subject a $C_{max}$ of a xanthine oxidoreductase inhibitor or a pharmaceutically acceptable salt thereof in a range of about 2.5 µg/mL to about 0.050 µg/mL. Even more specifically, the modified release dosage forms of the present disclosure, when administered orally to a subject in need of treatment thereof, can produce in that subject a $C_{max}$ of a xanthine oxidoreductase inhibitor or a pharmaceutically acceptable salt thereof in a range of about 2.0 µg/mL to about 0.075 µg/mL.

In yet another embodiment, the modified release dosage forms of the present disclosure comprise: a xanthine oxidoreductase inhibitor or a pharmaceutically acceptable salt thereof, wherein said dosage form, after oral administration to a subject in need of treatment thereof exhibits at least one of the following:

(a) maintains in the subject a plasma concentration of xanthine oxidoreductase inhibitor or pharmaceutically acceptable salt thereof greater than about 0.1 µg/mL for a period of from about 5 hours to about 14 hours; and (b) produces in the subject a maximum plasma concentration ($C_{max}$) of a xanthine oxidoreductase inhibitor or a pharmaceutically acceptable salt thereof in an amount between about 2.5 µg/mL to about 0.090 µg/mL.

Alternatively, the modified release dosage form, after oral administration to a subject in need of treatment thereof, exhibits the following:

(a) maintains in the subject a plasma concentration of xanthine oxidoreductase inhibitor or pharmaceutically acceptable salt thereof greater than about 0.1 µg/mL for a period of from about 5 hours to about 14 hours; and (b) produces in the subject a maximum plasma concentration ($C_{max}$) of a xanthine oxidoreductase inhibitor or a pharmaceutically acceptable salt thereof of between about 2.0 µg/mL to about 0.095 µg/mL.

Still further alternatively, the modified release dosage form, after oral administration to a subject in need of treatment thereof, can exhibit each of the following:

(a) maintains in the subject a plasma concentration of xanthine oxidoreductase inhibitor or pharmaceutically acceptable salt thereof greater than about 0.1 µg/mL for a period of from about 5 hours to about 14 hours; and (b) produces in the subject a maximum plasma concentration ($C_{max}$) of a xanthine oxidoreductase inhibitor or a pharmaceutically acceptable salt thereof of between about 2.5 µg/mL to about 0.090 µg/mL.

The modified release dosage forms of the present disclosure can contain from about 40 to about 240 mg of at least one xanthine oxidoreductase inhibitor or a pharmaceutically acceptable salt thereof.

When administered orally to a subject in need of treatment thereof, the modified release dosage forms of the present disclosure can produce in the subject a $C_{max}$ of a xanthine oxidoreductase inhibitor or a pharmaceutically acceptable salt thereof in an amount of about 2.5 µg/mL, about 2.4 µg/mL, about 2.3 µg/mL, about 2.2 µg/mL, about 2.1 µg/mL, 2.0 µg/mL about 1.9 µg/mL, about 1.8 µg/mL, about 1.7 µg/mL, about 1.6 µg/mL, about 1.5 µg/mL, about 1.4 µg/mL, about 1.3 µg/mL, about 1.2 µg/mL, about 1.1 µg/mL, about 1.0 µg/mL, about 0.9 µg/mL, about 0.8 µg/mL, about 0.7 µg/mL, about 0.6 µg/mL, about 0.5 µg/mL, about 0.4 µg/mL, about 0.3 µg/mL, about 0.2 µg/mL, about 0.1 µg/mL, about 0.099 µg/mL, about 0.098 µg/mL, about 0.097 µg/mL, about 0.096 µg/mL, about 0.095 µg/mL, about 0.094 µg/mL, about 0.093 µg/mL, about 0.092 µg/mL or about 0.091 µg/mL. Specifically, the modified release dosage forms of the present disclosure, when administered orally to a subject in need of treatment thereof, can produce in that subject a $C_{max}$ of a xanthine oxidoreductase inhibitor or a pharmaceutically acceptable salt thereof in a range of about 2.5 µg/mL to about 0.090 µg/mL. Even more specifically, the modified release dosage forms of the present disclosure, when administered orally to a subject in need of treatment thereof, can produce in that subject a $C_{max}$ of a xanthine oxidoreductase inhibitor or a pharmaceutically acceptable salt thereof in a range of about 2.0 µg/mL to about 0.095 µg/mL.

An example of a xanthine oxidoreductase inhibitor that can be used in the modified release dosage forms of the present disclosure are xanthine oxidoreductase inhibitors that comprise the formula:

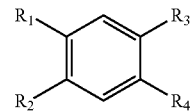

wherein $R_1$ and $R_2$ are each independently a hydrogen, a hydroxyl group, a COOH group, an unsubstituted or substituted $C_1$-$C_{10}$ alkyl group, an unsubstituted or substituted $C_1$-$C_{10}$ alkoxy, an unsubstituted or substituted hydroxyalkoxy, a phenylsulfinyl group or a cyano (—CN) group;

wherein $R_3$ and $R_4$ are each independently a hydrogen or A, B, C or D as shown below:

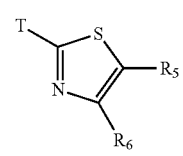

A

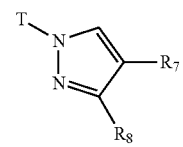

B

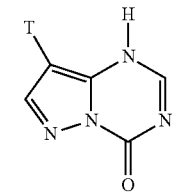

C

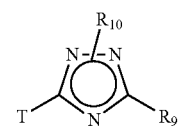

D wherein T connects A, B, C or D to the aromatic ring shown above at $R_1$, $R_2$, $R_3$ or $R_4$.

wherein $R_5$ and $R_6$ are each independently a hydrogen, a hydroxyl group, a COOH group, an unsubstituted or substituted $C_1$-$C_{10}$ alkyl group, an unsubstituted or substituted $C_1$-$C_{10}$ alkoxy, an unsubstituted or substituted hydroxyalkoxy, COO-Glucoronide or COO-Sulfate;

wherein $R_7$ and $R_8$ are each independently a hydrogen, a hydroxyl group, a COOH group, an unsubstituted or substituted $C_1$-$C_{10}$ alkyl group, an unsubstituted or substituted $C_1$-$C_{10}$ alkoxy, an unsubstituted or substituted hydroxyalkoxy, COO-Glucoronide or COO-Sulfate;

wherein $R_9$ is an unsubstituted pyridyl group or a substituted pyridyl group; and wherein $R_{10}$ is a hydrogen or a lower alkyl group, a lower alkyl group substituted with a pivaloyloxy group and in each case, $R_{10}$ bonds to one of the nitrogen atoms in the 1, 2, 4-triazole ring shown above.

Examples of compounds having the above formula are:
(a) 2-[3-cyano-4-(2-methylpropoxy)phenyl]-4-methylthiazole-5-carboxylic acid or a pharmaceutically acceptable salt thereof; (b) 2-[3-cyano-4-(3-hydroxy-2-methylpropoxy)phenyl]-4-methyl-5-thiazolecarboxylic acid or a pharmaceutically acceptable salt thereof; (c) 2-[3-cyano-4-(2-hydroxy-2-methylpropoxy)phenyl]-4-methyl-5-thiazolecarboxylic acid or a pharmaceutically acceptable salt thereof; (d) 2-(3-cyano-4-hydroxyphenyl)-4-methyl-5-thiazolecarboxylic acid or a pharmaceutically acceptable salt thereof; (e) 2-[4-(2-carboxypropoxy)-3-cyanophenyl]-4-methyl-5-thiazolecarboxylic acid or a pharmaceutically acceptable salt thereof; (f) 1-3-cyano-4-(2,2-dimethylpropoxy)phenyl]-1H-pyrazole-4-carboxylic acid or a pharmaceutically acceptable salt thereof, (g) pyrazolo [1,5-a]-1,3,5-triazin-4-(1H)-one, 8-[3-methoxy-4-(phenylsulfinyl)phenyl]-sodium salt (±); and (h) 3-(2-methyl-4-pyridyl)-5-cyano-4-isobutoxyphenyl)-1,2,4-triazole or a pharmaceutically acceptable salt thereof.

Another example of at least one xanthine oxidoreductase inhibitor that can be used in the modified release dosage forms of the present disclosure are xanthine oxidoreductase inhibitors that comprise the formula:

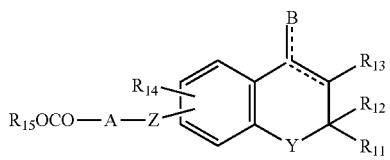

wherein $R_{11}$ and $R_{12}$ are each independently a hydrogen, a substituted or unsubstituted lower alkyl group, a substituted or unsubstituted phenyl, or $R_{11}$ and $R_{12}$ may together form a four- to eight-membered carbon ring together with the carbon atom to which they are attached;

wherein $R_{13}$ is a hydrogen or a substituted or unsubstituted lower alkyl group;

wherein $R_{14}$ is one or two radicals selected from a group consisting of a hydrogen, a halogen, a nitro group, a substituted or unsubstituted lower alkyl, a substituted or unsubstituted phenyl, —$OR_{16}$ and —$SO_2NR_{17}R_{17'}$, wherein $R_{16}$ is a hydrogen, a substituted or unsubstituted lower alkyl, a phenyl-substituted lower alkyl, a carboxymethyl or ester thereof, a hydroxyethyl or ether thereof, or an allyl; $R_{17}$ and $R_{17'}$ are each independently a hydrogen or a substituted or unsubstituted lower alkyl;

wherein $R_{15}$ is a hydrogen or a pharmaceutically active ester-forming group;

wherein A is a straight or branched hydrocarbon radical having one to five carbon atoms;

wherein B is a halogen, an oxygen, or a ethylenedithio;

wherein Y is an oxygen, a sulfur, a nitrogen or a substituted nitrogen;

wherein Z is an oxygen, a nitrogen or a substituted nitrogen; and the dotted line refers to either a single bond, a double bond, or two single bonds.

In another embodiment, the present disclosure relates to a method of treating a patient suffering from gout, hyperuricemia, prostatitis, inflammatory bowel disease, QT interval prolongation, myocardial infarction, cardiac hypertrophy, hypertension, nephrolithiasis, renal impairment, chronic kidney disease, metabolic syndrome, diabetes, diabetic nephropathy or congestive heart failure and in need of treatment thereof. The method comprises the step of: administering to a subject suffering from gout, hyperuricemia, prostatitis, inflammatory bowel disease, QT interval prolongation, myocardial infarction, cardiac hypertrophy, hypertension, nephrolithiasis, renal impairment, chronic kidney disease, metabolic syndrome, diabetes, diabetic nephropathy or congestive heart failure and in need of treatment thereof, a therapeutically effective amount of above described modified release dosage form comprising at least one xanthine oxidoreductase inhibitor or at least one xanthine oxidase inhibitor.

In a further embodiment, the present disclosure relates to a pharmaceutical composition that comprises a xanthine oxidoreductase inhibitor or a pharmaceutically acceptable salt thereof or at least one xanthine oxidase inhibitor or a pharmaceutically acceptable salt thereof and at least one pharmaceutically acceptable polymer, wherein the pharmaceutical composition includes at least one of the following: an immediate release component, a delayed release component, and/or a controlled release component. Examples of xanthine oxidoreductase inhibitors that may be incorporated in the pharmaceutical composition include all those previously cited. An example of a xanthine oxidase inhibitor is oxypurinol or allopurinol. In addition, the immediate release component, delayed release component, and controlled release component may comprise one or more beads capable of various release profiles. Immediate release beads release the xanthine oxidoreductase inhibitor immediately after ingestion, the delayed release beads release the xanthine oxidoreductase inhibitor upon exposure to internal environments with specified pH levels, and the controlled release beads release the xanthine oxidoreductase inhibitor over an extended period of time compared to the immediate release bead. The various beads comprise an inert core coated with a xanthine oxidoreductase inhibitor compound and one or more layers of a pharmaceutically acceptable polymer.

In an additional embodiment, the current disclosure encompasses a single pharmaceutical composition that incorporates both immediate release beads and delayed release beads with solubility at pH levels greater than or equal to 6.8. The pharmaceutical composition of this embodiment comprises immediate release xanthine oxidoreductase inhibitor or xanthine oxidase inhibitor beads in an amount ranging from approximately 20% to approximately 40% (w/w) of the total composition weight delayed release xanthine oxidoreductase inhibitor or xanthine oxidase inhibitor beads that release at a pH of 6.8 in an amount ranging from approximately 60% to approximately 80% (w/w) of the total composition weight. For example, in one aspect, the pharmaceutical composition comprises comprises immediate release xanthine oxidoreductase inhibitor or xanthine oxidase inhibitor beads in an amount of approximately 20% (w/w) of the total composition weight delayed release xanthine oxidoreductase inhibitor or xanthine oxidase inhibitor beads that release at a pH of 6.8 in an amount of approximately 80% (w/w) of the total composition weight. In yet another aspect, the pharmaceutical composition comprises immediate release xanthine oxidoreductase inhibitor or xanthine oxidase inhibitor beads in an amount of approximately 25% (w/w) of the total composition weight delayed release xanthine oxidoreductase inhibitor or xanthine oxidase inhibitor beads that release at a pH of 6.8 in an amount of approximately 75% (w/w) of the total composition weight. In still yet another aspect, the pharmaceutical composition comprises immediate release xanthine oxidoreductase inhibitor or xanthine oxidase inhibitor beads in an amount of approximately 30% (w/w) of the total composition weight delayed release xanthine oxidoreductase inhibitor or xanthine oxidase inhibitor beads that release at a pH of 6.8 in an amount of approximately 70% (w/w) of the total composition weight. In still yet another aspect, the pharmaceutical composition comprises immediate release xanthine oxidoreductase inhibitor or xanthine oxidase inhibitor beads in an amount of approximately 40% (w/w) of the total composition weight delayed release xanthine oxidoreductase inhibitor or xanthine oxidase inhibitor beads that release at a pH of 6.8 in an amount of approximately 60% (w/w) of the total composition weight.

In yet another embodiment of the current disclosure, the pharmaceutical dosage form encompasses a single pharmaceutical composition that incorporates immediate release beads, delayed release beads with solubility at pH levels greater than or equal to 6.0, and delayed release beads with solubility at pH levels greater than or equal to 6.8. The pharmaceutical composition of this embodiment comprises immediate release xanthine oxidoreductase inhibitor beads in an amount ranging from approximately 25% to approximately 35% (w/w) of the total composition weight, pH 6.0 delayed release xanthine oxidoreductase inhibitor or xanthine oxidase inhibitor beads in an amount ranging from approximately 25% to approximately 35% (w/w) of the total composition weight, and pH 6.8 delayed release xanthine oxidoreductase inhibitor or xanthine oxidase inhibitor beads in an amount ranging from approximately 35% to approximately 45% (w/w) of the total composition weight.

In a further embodiment of the current disclosure, the pharmaceutical composition encompasses a single pharmaceutical composition that incorporates immediate release beads and delayed-controlled release beads, with the delayed release beads having solubility at a pH level of at least 6.8 and a controlled release rate of approximately four to six hours. The pharmaceutical composition of this embodiment comprises immediate release xanthine oxidoreductase inhibitor or xanthine oxidase inhibitor beads in an amount ranging from approximately 20% to approximately 40% (w/w) of the total composition weight and delayed-controlled release xanthine oxidoreductase inhibitor or xanthine oxidase inhibitor beads having solubility at pH levels greater than or equal to 6.8 and providing prolonged release of xanthine oxidoreductase inhibitor or xanthine oxidase inhibitor over a period of about 4 hours to about 6 hours, in an amount ranging from approximately 60% to approximately 80% (w/w) of the total composition weight.

In still another embodiment of the current disclosure, the pharmaceutical composition encompasses a single pharmaceutical composition that incorporates immediate release beads and controlled release beads capable of active release over approximately ten to approximately twelve hours. The pharmaceutical composition of this embodiment generally comprises immediate release xanthine oxidoreductase inhibitor or xanthine oxidase inhibitor beads in an amount ranging from approximately 10% to approximately 30% (w/w) of the total composition weight and controlled release xanthine oxidoreductase inhibitor or xanthine oxidase inhibitor beads providing prolonged release of xanthine oxidoreductase inhibitor or xanthine oxidase inhibitor over a period of about 10 hours to about 12 hours, in an amount ranging from approximately 70% to approximately 90% (w/w) of the total composition weight.

The development of the previously described embodiments resulted from a long drug development process. Initially, a dose-escalation, placebo-controlled, double blind study was performed on twelve healthy subjects, designed to assess the safety and maximum tolerated dose of febuxostat by oral administration. The study was also designed to assess the pharmacokinetic and pharmacodynamic profiles of multiple daily oral doses over a range of doses and ranges, including both once-daily and twice-daily administration. The results of this study established valuable pharmacokinetic and pharmacodynamic information pertaining to febuxostat bioavailability in vivo. The results of this study were published in the article: Reza Khosravan et al., *Pharmcokinetics, Pharmacodynamics and Safety of Febuxostat, a Non-Purine Selective Inhibitor of Xanthine Oxidase, in a Dose Escalation Study in Healthy Subjects*, CLINICAL PHARMACOKINETICS, 2006: 45 (8): 821-841. Specifically, the pharmacokinetic parameters of the study are discussed on page 829 of the article, and are shown in Table 1 of Example 1, included herein.

In a Phase 1, multiple-dose, randomized, placebo-controlled, double-blind, single-center, multiple-location dose escalation study involving febuxostat, the pharmacokinetics and pharmacodynamics of febuxostat was studied in healthy subjects. In this study, oral doses of an immediate release dosage form of febuxostat (a xanthine oxidoreductase inhibitor) ranged from 10 mg once a day to 240 mg once a day (hereinafter "QD") and as 30 mg twice a day (hereinafter "BID"). In this study, it was determined that a dose of 30 mg febuxostat administered twice daily (for a total dose of 60 mg daily) was as effective in lowering uric acid levels as a once daily 120 mg febuxostat dose. Given these findings, it was determined that maintenance of drug levels above a minimum concentration was critical to improved uric acid lowering. Through further research and gathering of pharmacokinetic data, it was determined that maintenance of in vivo febuxostat concentrations at or above 100 ng/mL (0.1 µg/mL) resulted in 80% or greater inhibition of uric acid levels. In view of this surprising determination, the inventors developed an extended release febuxostat formulation effective in maximizing time spent above the minimum critical febuxostat concentration of 100 ng/mL (0.1 µg/mL).

The pharmacokinetic data obtained in the clinical trial referenced above was subsequently used to develop estimated plasma profiles for various febuxostat formulations, including extended release matrix tablets, two-pulse febuxostat formulations, and three-pulse febuxostat formulations. The estimated extended release formulation data was based on a matrix formulation incorporating one or more polymers, and the estimated two-pulse and three-pulse formulation data was based on a formulation incorporating two or more types of beads with differing release profiles. This information and methodology is discussed in Example 2. Additionally, as part of the development process for an extended release febuxostat formulation, various sites of absorption were investigated to determine the optimal physiologic sites of drug absorption for an extended release febuxostat formulation. In early pre-clinical studies, absorption of febuxostat from various regions of the gastrointestinal tract was studied in rats. The testing in rat models showed that absorption of febuxostat was very poor from the colonic region. To guide development of a dosage form that provided the desired plasma concentration-time profile, a site of absorption study was conducted in humans. This data and the methodology for gathering the information are included in Example 3. The site of absorption data surprisingly showed that absorption of febuxostat in the colon was only approximately 40% compared to the absorption profiles witnessed with immediate release, proximal intestine, and distal intestine formulations, higher than what would be expected from the rat data.

In view of this surprising test data, the inventors began development of an extended release febuxostat formulation that minimized febuxostat exposure in the colon, and maximized febuxostat exposure in other areas, including the stomach, proximal intestine, and distal intestine. Novel febuxostat formulations were developed by producing febuxostat formulations with immediate release components, delayed release components based on pH levels, and continuous release components based on release profile over an extended time period. Specific formulations are described in Examples 4-9. The novel febuxostat formulations were then tested in a dog model, as described in Example 10. The results of testing in the dog model were expected given the well-recognized limitations of pharmacokinetic testing in dog models. Despite the limitations regarding the length of the dog gastrointestinal tract, the delayed release (i.e., pH dependent) formulations exhibited improved pharmacokinetic parameters compared to the reference immediate release febuxostat formulation. These formulations were then tested in humans in a single-dose study as described in Example 11.

The specific parameters and scope of the extended release febuxostat formulations are described in greater detail in the Detailed Description.

BRIEF DESCRIPTION OF THE FIGURES

FIG. 1 illustrates the average plasma febuxostat concentration over time for a dosage form designed to release febuxostat immediately in the stomach, in the proximal small intestine, in the distal small intestine, and in the colon.

FIG. 5 shows a table listing the compositions of eight febuxostat modified release matrix tablet formulations.

In FIGS. 8A and 8B the formulations are as follows:

Formulation A (reference): Febuxostat (Uloric) IR 80 mg tablet.
Formulation B (test): Two-pulsatile prototype (80 mg) febuxostat capsule (TMX-67 XR Formulation B).
Formulation C (test): Three-pulsatile prototype (80 mg) febuxostat capsule (TMX-67 XR Formulation C).
Formulation D (test): Combination of pulsatile and continuous release (80 mg) febuxostat capsule (TMX-67 Formulation D).
Formulation E (test): Continuous release (80 mg) prototype febuxostat capsule (TMX-67 XR Formulation E).

Figure 9:
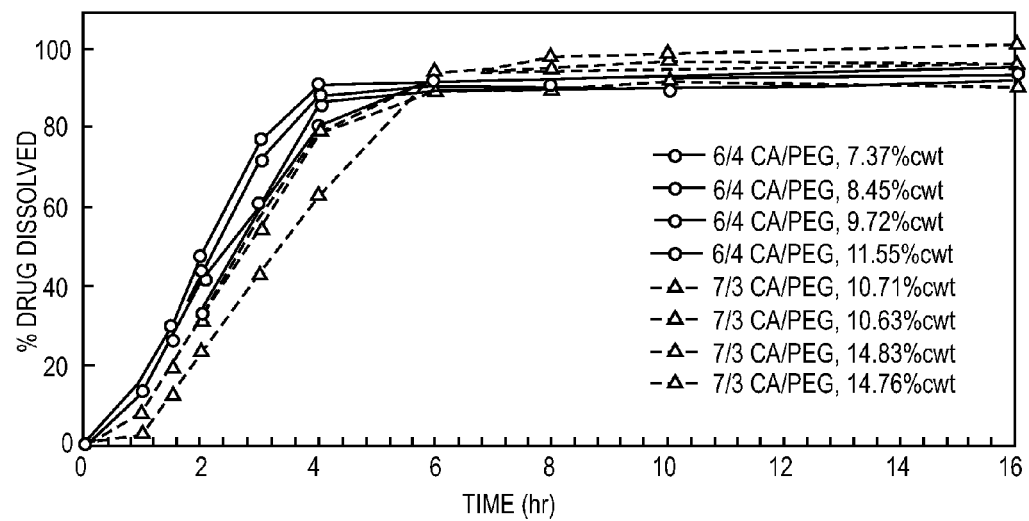

FIG. 9 shows how the dissolution profile of the formulations described in Example 12 can be varied pending on the ratio of cellulose acetate to polyethylene glycol (PEG).

Figure 10:
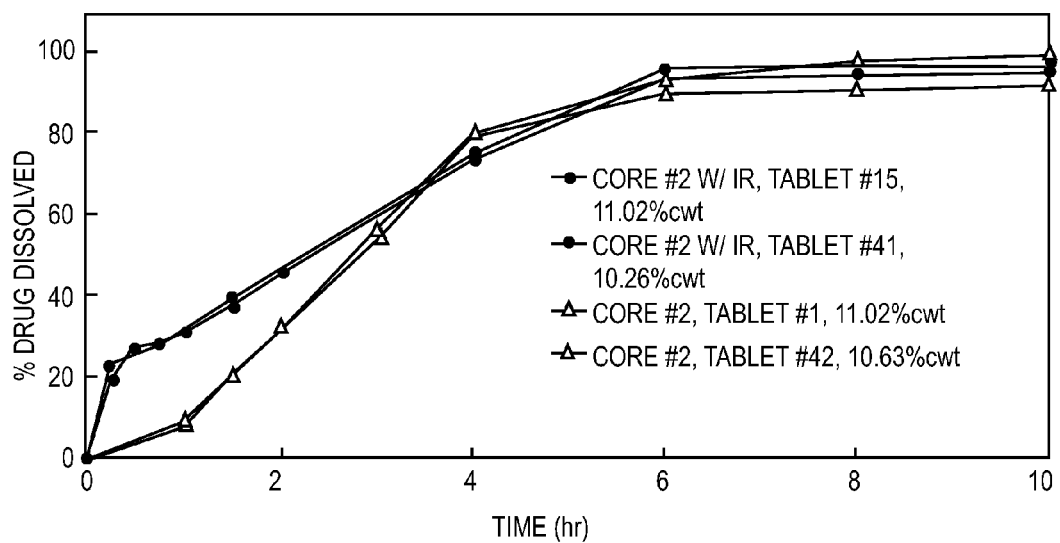

FIG. 10 shows how a formulation described in Example 12 can be overcoated with an immediate release layer of the drug (febuxostat) to overcome a time-lag.

Figure 11:
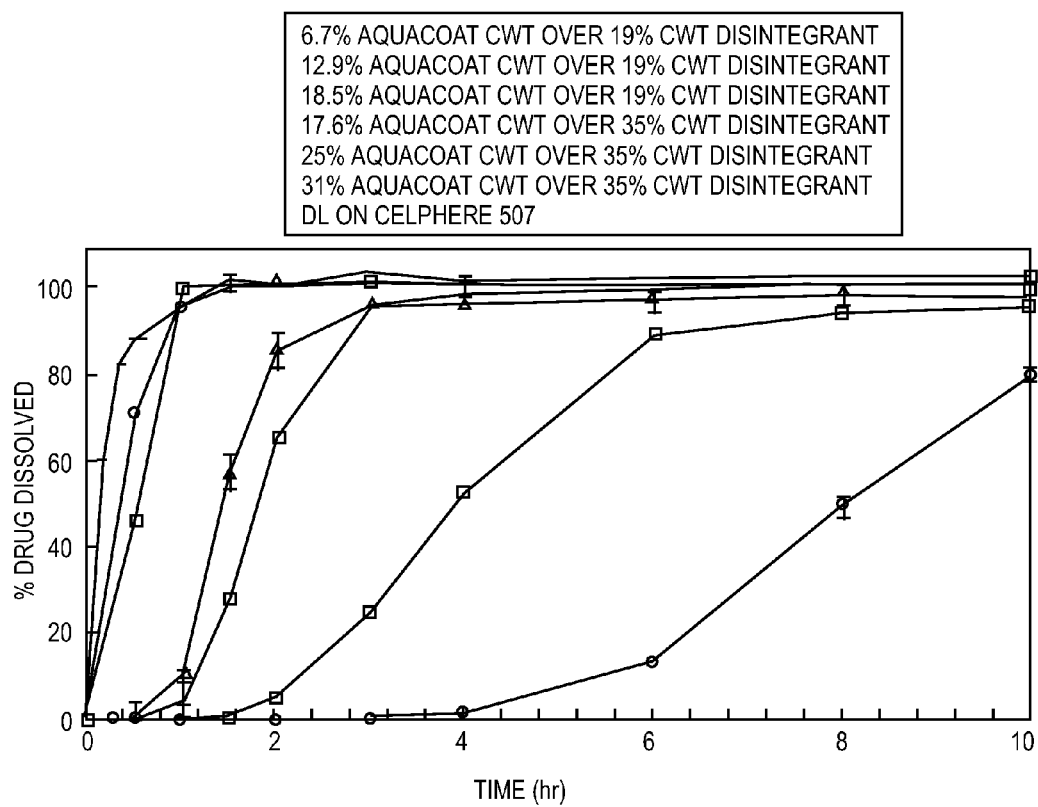

FIG. 11 shows how multiparticulate formulations described in Example 12 can be prepared to have desired release characteristics by varying the amount of ethylcellulose coating contained on said formulations.

DETAILED DESCRIPTION OF THE DISCLOSURE

I. Definitions

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the use of the term "about" indicates that values slightly outside the cited values, namely, plus or minus 10%. Such dosages are thus encompassed by the scope of the claims reciting the terms "about" and "approximately."

As used herein, the term "AUC" refers to the area under the plasma concentration time curve of the active agent and which is calculated using the trapezoidal rule. The term "$AUC_t$" means the area under the plasma concentration time curve from time 0 to 120 hours after administration in units of ng·h/mL as determined using the trapezoidal rule. The term "$AUC\infty$" means the area under the plasma concentration time curve from time 0 to infinite time. $AUC\infty$ is calculated as $AUC_t+LMT/(-\beta)$, where "LMT" is the last measurable plasma concentration and $\beta$ is the terminal phase elimination rate constant. Unless otherwise noted herein, the reported value for the AUC is the central value of the AUC. The "central value" of the AUC is the mean AUC±standard deviation.

The terms "administer", "administering", "administered" or "administration" refer to any manner of providing a drug (such as, a xanthine oxidoreductase inhibitor or a pharmaceutically acceptable salt thereof) to a subject or patient. Routes of administration can be accomplished through any means known by those skilled in the art. Such means include, but are not limited to, oral, buccal, intravenous, subcutaneous, intramuscular, transdermal, by inhalation and the like.

The term "active agent" as used herein refers to (1) a xanthine oxidoreductase inhibitor or a pharmaceutically acceptable salt thereof or (2) a xanthine oxidase inhibitor or a pharmaceutically acceptable salt thereof. The term "active agent" and "drug" are used interchangeably herein. The solid state form of the active agent used in preparing the dosage forms of the present disclosure is not critical. For example, active agent used in preparing the modified release dosage forms of the present disclosure can be amorphous or crystalline. The final dosage form contains at least a detectable amount of crystalline active agent. The crystalline nature of the active agent can be detected using powder X-ray diffraction analysis, by differential scanning calorimetry or any other techniques known in the art.

The term "$C_{max}$" refers to the maximum observed plasma concentration of a xanthine oxidoreductase inhibitor or salt thereof produced by the ingestion of the dosage forms of the present disclosure. Unless otherwise noted herein, the reported value for the $C_{max}$ is the central value of the $C_{max}$. The "central value" of the $C_{max}$ is the mean $C_{max}$±standard deviation.

As used herein, the term "delayed release" refers to a type of modified release wherein a drug dosage form exhibits a time delay between oral administration of the drug dosage form and the release of the drug from said dosage form. Pulsed release systems (also known as "pulsatile drug release") and the use of enteric coatings, which are well known to those skilled in the art, are examples of delayed release mechanisms. Generally, delayed release dosage forms release little or no active compound for a predetermined time or until a predetermined condition is met, such as exposure to a certain pH level, then release of the active compound occurs immediately thereafter.

As used herein, the term "delayed-controlled release" refers to a type of modified release wherein a drug dosage form exhibits a prolonged release of the drug over a set time period, with release not initiated until after a certain time delay post ingestion of the dosage form. Generally, a "delayed-controlled release" dosage form releases little or no active compound, for a predetermined time or until a predetermined condition is met, such as exposure to a certain pH range, then release of the active compound occurs over an additional prolonged period of time.

The term "dosage form" refers to any solid object, semisolid, or liquid composition designed to contain a specific pre-determined amount (i.e., dose) of a certain active agent. Suitable dosage forms may be pharmaceutical drug delivery systems, including those for oral administration, buccal administration, rectal administration, topical or mucosal delivery or subcutaneous implants, or other implanted drug delivery systems and the like. Preferably, the dosage forms of the present disclosure are considered to be solid, however, they may contain liquid or semi-solid components. More preferably, the dosage form is an orally administered system for delivering an active agent to the gastrointestinal tract of a subject. The dosage form of the present disclosure exhibit modified release of the active agent.

By an "effective amount" or a "therapeutically effective amount" of an active agent is meant a nontoxic but sufficient amount of the active agent to provide the desired effect. The amount of active agent that is "effective" will vary from subject to subject, depending on the age and general condition of the individual, the particular active agent or agents, and the like. Thus, it is not always possible to specify an exact "effective amount." However, an appropriate "effective amount" in any individual case may be determined by one of ordinary skill in the art using routine experimentation.

As used herein, the term "extended release" refers to a drug formulation that provides for the gradual release of a drug over an extended period of time. The term "controlled" release refers to a type of extended release formulation where the gradual release of the drug is controlled or manipulated over a certain extended period of time.

The term "immediate release" is used in its conventional sense to refer to a dosage form that provides for release of the active agent immediately after drug administration.

As used herein, the term "modified" refers to a drug containing formulation in which release of the drug is not immediate (See, for example, *Guidance for Industry SUPAC-MR: Modified Release Solid Oral Dosage Forms, Scale-Up and Postapproval Changes: Chemistry, Manufacturing, and Controls; In Vitro Dissolution, Testing and In Vivo Bioequivalence Documentation*, U.S. Department of Health and Human Services, Food and Drug Administration, Center for Drug Evaluation and Research ("CDER"), September 1997 CMC 8, page 34, herein incorporated by reference.). In a modified formulation, modified release dosage form or modified dosage form, administration of said formulation or dosage form does not result in immediate release of the drug or active agent into an absorption pool. The term is used interchangeably with "nonimmediate release" as defined in *Remington: The Science and Practice of Pharmacy*, Nineteenth Ed. (Easton, Pa.: Mack Publishing Company, 1995). As used herein, the term "modified release" includes extended or controlled release, delayed release and delayed-controlled release formulations.

By "pharmaceutically acceptable," such as in the recitation of a "pharmaceutically acceptable excipient," or a "pharmaceutically acceptable additive," is meant a material that is not biologically or otherwise undesirable, i.e., the material may be incorporated into a pharmaceutical composition administered to a patient without causing any undesirable biological effects.

The term "subject" refers to an animal, preferably a mammal, including a human or non-human. The terms patient and subject may be used interchangeably herein. The terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual by inhibiting or causing regression of a disorder or disease.

As used herein, the term "xanthine oxidoreductase" refers to at least one form of xanthine oxidoreductase enzyme, namely xanthine oxidase and/or xanthine dehydrogenase.

As used herein, the phrase "xanthine oxidoreductase inhibitor" refers to any compound that (1) is an inhibitor of a xanthine oxidoreductase, such as, but not limited to, xanthine oxidase; and (2) chemically, does not contain a purine ring in its structure (i.e. is a "non-purine"). The phrase "xanthine oxidoreductase inhibitor" as defined herein also includes metabolites, polymorphs, solvates and prodrugs of the such compounds, including metabolites, polymorphs, solvates and prodrugs of the compounds described in Formula I and Formula II below. Examples of xanthine oxidoreductase inhibitors include, but are not limited to, 2-[4-(2-carboxypropoxy)-3-cyanophenyl]-4-methyl-5-thiazolecarboxylic acid and compounds having the following Formula I or Formula II:

Compounds of Formula I

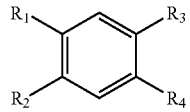

wherein $R_1$ and $R_2$ are each independently a hydrogen, a hydroxyl group, a COOH group, an unsubstituted or substituted $C_1$-$C_{10}$ alkyl group, an unsubstituted or substituted $C_1$-$C_{10}$ alkoxy, an unsubstituted or substituted hydroxyalkoxy, a phenylsulfinyl group or a cyano (—CN) group; wherein $R_3$ and $R_4$ are each independently a hydrogen or A, B, C or D as shown below:

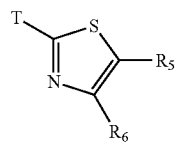 A

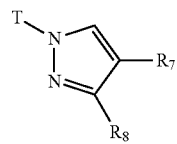 B

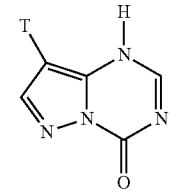 C

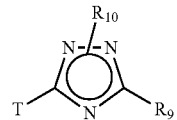 D wherein T connects or attaches A, B, C or D to the aromatic ring shown above at $R_1$, $R_2$, $R_3$ or $R_4$.

wherein $R_5$ and $R_6$ are each independently a hydrogen, a hydroxyl group, a COOH group, an unsubstituted or substituted $C_1$-$C_{10}$ alkyl group, an unsubstituted or substituted $C_1$-$C_{10}$ alkoxy, an unsubstituted or substituted hydroxyalkoxy, COO-Glucoronide or COO-Sulfate;

wherein $R_7$ and $R_8$ are each independently a hydrogen, a hydroxyl group, a COOH group, an unsubstituted or substituted $C_1$-$C_{10}$ alkyl group, an unsubstituted or substituted $C_1$-$C_{10}$ alkoxy, an unsubstituted or substituted hydroxyalkoxy, COO-Glucoronide or COO-Sulfate;

wherein $R_9$ is an unsubstituted pyridyl group or a substituted pyridyl group; and wherein $R_{10}$ is a hydrogen or a lower alkyl group, a lower alkyl group substituted with a pivaloyloxy group and in each case, $R_{10}$ bonds to one of the nitrogen atoms in the 1, 2, 4-triazole ring shown above in Formula I.

Compounds of Formula II:

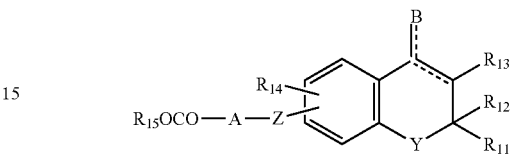

wherein $R_{11}$ and $R_{12}$ are each independently a hydrogen, a substituted or unsubstituted lower alkyl group, a substituted or unsubstituted phenyl (the substituted phenyl in this Formula II refers to a phenyl substituted with a halogen or lower alkyl, and the like. Examples include, but are not limited to, p-tolyl and p-chlorophenyl), or $R_{11}$ and $R_{12}$ may together form a four- to eight-membered carbon ring together with the carbon atom to which they are attached;

wherein $R_{13}$ is a hydrogen or a substituted or unsubstituted lower alkyl group;

wherein $R_{14}$ is one or two radicals selected from a group consisting of a hydrogen, a halogen, a nitro group, a substituted or unsubstituted lower alkyl group, a substituted or unsubstituted phenyl (the substituted phenyl in this Formula II refers to a phenyl substituted with a halogen or lower alkyl group, and the like. Examples include, but are not limited to, p-tolyl and p-chlorophenyl), —$OR_{16}$ and —$SO_2NR_{17}R_{17'}$, wherein $R_{16}$ is a hydrogen, a substituted or unsubstituted lower alkyl, a phenyl-substituted lower alkyl, a carboxymethyl or ester thereof, a hydroxyethyl or ether thereof, or an allyl; $R_{17}$ and $R_{17'}$ are each independently a hydrogen or a substituted or unsubstituted lower alkyl group;

wherein $R_{15}$ is a hydrogen or a pharmaceutically active ester-forming group;

wherein A is a straight or branched hydrocarbon radical having one to five carbon atoms;

wherein B is a halogen, an oxygen, or an ethylenedithio;

wherein Y is an oxygen, a sulfur, a nitrogen or a substituted nitrogen;

wherein Z is an oxygen, a nitrogen or a substituted nitrogen; and the dotted line refers to either a single bond, a double bond, or two single bonds (for example, when B is ethylenedithio, the dotted line shown in the ring structure can be two single bonds).

As used herein, the term "lower alkyl(s)" group refers to a $C_1$-$C_7$ alkyl group, including, but not limited to, including methyl, ethyl, n-propyl, isopropyl, butyl, isobutyl, sec-butyl, tert-butyl, pentyl, isopentyl, hexyl, heptal and the like.

As used herein, the term "lower alkoxy" refers to those groups formed by the bonding of a lower alkyl group to an oxygen atom, including, but not limited to, methoxy, ethoxy, propoxy, isopropoxy, butoxy, isobutoxy, pentoxy, hexoxy, heptoxy and the like.

As used herein, the term "lower alkylthio group" refers to those groups formed by the bonding of a lower alkyl to a sulfur atom.

As used herein, the term "halogen" refers to fluorine, chlorine, bromine and iodine.

As used herein, the term "substituted pyridyl" refers to a pyridyl group that can be substituted with a halogen, a cyano group, a lower alkyl, a lower alkoxy or a lower alkylthio group.

As used herein, the term "four- to eight-membered carbon ring" refers to cyclobutyl, cyclopentyl, cyclohexyl, cycloheptyl, cyclooctyl and the like.

As used herein, the phrase "pharmaceutically active ester-forming group" refers to a group which binds to a carboxyl group through an ester bond. Such ester-forming groups can be selected from carboxy-protecting groups commonly used for the preparation of pharmaceutically active substances, especially prodrugs. For the purpose of the present disclosure, said group should be selected from those capable of binding to compounds having Formula II wherein $R_{15}$ is hydrogen through an ester bond. Resultant esters are effective to increase the stability, solubility, and absorption in gastrointestinal tract of the corresponding non-esterified forms of said compounds having Formula II, and also prolong the effective blood-level of it. Additionally, the ester bond can be cleaved easily at the pH of body fluid or by enzymatic actions in vivo to provide a biologically active form of the compound having Formula II. Preferred pharmaceutically active ester-forming groups include, but are not limited to, 1-(oxygen substituted)-$C_2$ to $C_{15}$ alkyl groups, for example, a straight, branched, ringed, or partially ringed alkanoyloxyalkyl groups, such as acetoxymethyl, acetoxyethyl, propionyloxymethyl, pivaloyloxymethyl, pivaloyloxyethyl, cyclohexaneacetoxyethyl, cyclohexanecarbonyloxycyclohexylmethyl, and the like, $C_3$ to $C_{15}$ alkoxycarbonyloxyalkyl groups, such as ethoxycarbonyloxyethyl, isopropoxycarbonyloxyethyl, isopropoxycarbonyloxypropyl, t-butoxycarbonyloxyethyl, isopentyloxycarbonyloxypropyl, cyclohexyloxycarbonyloxyethyl, cyclohexyl methoxycarbonyloxyethyl, bornyloxycarbonyloxyisopropyl, and the like, $C_2$ to $C_8$ alkoxyalkyls, such as methoxy methyl, methoxy ethyl, and the like, $C_4$ to $C_8$ 2-oxacycloalkyls such as, tetrahydropyranyl, tetrahydrofuranyl, and the like, substituted $C_8$ to $C_{12}$ aralkyls, for example, phenacyl, phthalidyl, and the like, $C_6$ to $C_{12}$ aryl, for example, phenyl xylyl, indanyl, and the like, $C_2$ to $C_{12}$ alkenyl, for example, allyl, (2-oxo-1,3-dioxolyl)methyl, and the like, and [4,5-dihydro-4-oxo-1H-pyrazolo[3,4-d]pyrimidin-1-yl] methyl, and the like.

In $R_{16}$ in Formula II, the term "ester" as used in the phrase "the ester of carboxymethyl" refers to a lower alkyl ester, such as methyl or ethyl ester; and the term "ether" used in the phrase "the ether of hydroxyethyl" means an ether which is formed by substitution of the hydrogen atom of hydroxyl group in the hydroxyethyl group by aliphatic or aromatic alkyl group, such as benzyl.

The carboxy-protecting groups may be substituted in various ways. Examples of substituents include halogen atom, alkyl groups, alkoxy groups, alkylthio groups and carboxy groups.

As used herein, the term "straight or branched hydrocarbon radical" in the definition of A in Formula II above refers to methylene, ethylene, propylene, methylmethylene, or isopropylene.

As used herein, the substituent of the "substituted nitrogen" in the definition of Y and Z in Formula II above are hydrogen, lower alkyl, or acyl.

As used herein, the term "phenyl-substituted lower alkyl" refers to a lower alkyl group substituted with phenyl, such as benzyl, phenethyl or phenylpropyl. As used herein, the term "prodrug" refers to a derivative of the compounds shown in the above-described Formula I and Formula II that have chemically or metabolically cleavable groups and become by solvolysis or under physiological conditions compounds that are pharmaceutically active in vivo. Esters of carboxylic acids are an example of prodrugs that can be used in the dosage forms of the present disclosure. Methyl ester prodrugs may be prepared by reaction of a compound having the above-described formula in a medium such as methanol with an acid or base esterification catalyst (e. g., NaOH, $H_2SO_4$). Ethyl ester prodrugs are prepared in similar fashion using ethanol in place of methanol.

Examples of compounds having the above Formula I are: 2-[3-cyano-4-(2-methylpropoxy)phenyl]-4-methylthiazole-5-carboxylic acid (also known as "febuxostat"), 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid, 1-(3-cyano-4-(2,2-dimethylpropoxy)phenyl)-1H-pyrazole-4-carboxylic acid, 1-3-cyano-4-(2,2-dimethylpropoxy)phenyl]-1H-pyrazole-4-carboxylic acid, pyrazolo [1,5-a]-1,3,5-triazin-4-(1H)-one, 8-[3-methoxy-4-(phenylsulfinyl)phenyl]-sodium salt (±) or 3-(2-methyl-4-pyridyl)-5-cyano-4-isobutoxyphenyl)-1,2,4-triazole.

Preferred compounds having the above Formula I are: 2-[3-cyano-4-(2-methylpropoxy)phenyl]-4-methylthiazole-5-carboxylic acid, 2-[3-cyano-4-(3-hydroxy-2-methylpropoxy)phenyl]-4-methyl-5-thiazolecarboxylic acid, 2-[3-cyano-4-(2-hydroxy-2-methylpropoxy)phenyl]-4-methyl-5-thiazolecarboxylic acid, 2-(3-cyano-4-hydroxyphenyl)-4-methyl-5-thiazolecarboxylic acid, 2-[4-(2-carboxypropoxy)-3-cyanophenyl]-4-methyl-5-thiazolecarboxylic acid. These preferred compounds have also been found not have an effect at a therapeutically effective amount in a subject on the activity of any of the following enzymes involved in purine and pyrimidine metabolism: guanine deaminase, hypoxanthine-guanine phosphoribosyltransferse, purine nucleotide phosphorylase, orotate phosphoribosyltransferase or orotidine-5-monophosphate decarboxylase (i.e., meaning that it is "selective" for none of these enzymes which are involved in purine and pyrimidine metabolism). Assays for determining the activity for each of the above-described enzymes is described in Yasuhiro Takano, et al., *Life Sciences*, 76:1835-1847 (2005). These preferred compounds have also been referred to in the literature as nonpurine, selective inhibitors of xathine oxidase (NP/SIXO).

Examples of compounds having the above Formula II are described in U.S. Pat. No. 5,268,386 and EP 0 415 566 A1, and are incorporated, in their entirety, herein.

With the exception of pyrazolo [1,5-a]-1,3,5-triazin-4-(1H)-one, 8-[3-methoxy-4-(phenylsulfinyl)phenyl]-sodium salt (±), methods for making xanthine oxidoreductase inhibiting compounds of Formulas I and II for use in the methods of the present disclosure are known in the art and are described, for example, in U.S. Pat. Nos. 5,268,386, 5,614,520, 6,225,474, 7,074,816 and EP 0 415 566 A1 and in the publications Ishibuchi, S. et al., *Bioorg. Med. Chem. Lett.*, 11:879-882 (2001) and which are each herein incorporated by reference. Other xanthine oxidoreductase inhibiting compounds can be found using xanthine oxidoreductase and xanthine in assays to determine if such candidate compounds inhibit conversion of xanthine into uric acid. Such assays are well known in the art.

Pyrazolo [1,5-a]-1,3,5-triazin-4-(1H)-one, 8-[3-methoxy-4-(phenylsulfinyl)phenyl]-sodium salt (±) is available from Otsuka Pharmaceutical Co. Ltd. (Tokyo, Japan) and is described in the following publications: Uematsu T., et al., "Pharmacokinetic and Pharmacodynamic Properties of a Novel Xanthine Oxidase Inhibitor, BOF-4272, in Healthy Volunteers, *J. Pharmacology and Experimental Therapeutics*, 270:453-459 (August 1994), Sato, S., A Novel Xanthine Deydrogenase Inhibitor (BOF-4272). *In Purine and Pyrimidine Metabolism in Man*, Vol. VII, Part A, ed. By P. A. Harkness, pp. 135-138, Plenum Press, New York. Pyrazolo [1,5-a]-1,3,5-triazin-4-(1H)-one, 8-[3-methoxy-4-(phenylsulfinyl)phenyl]-sodium salt (±) can be made using routine techniques known in the art.

II. Dosage Forms

The present disclosure relates to modified release solid dosage forms comprising at least one active agent. Specifically, the at least one active agent contained in the modified release solid dosage forms of the present disclosure is at least one xanthine oxidoreductase inhibitor or at least one xanthine oxidase inhibitor.

The modified release dosage forms of the present disclosure can achieve any one of a number of objects. First, the modified release dosage forms of the present disclosure, when administered to a subject in need of treatment thereof, provide a high percentage of xanthine oxidoreductase inhibition or xanthine oxidase inhibition at a maximum observed plasma concentration (namely $C_{max}$) that is significantly lower than that provided by an immediate release dosage form containing at least one xanthine oxidoreductase inhibitor (for example, an immediate release dosage form containing 40 mg, 80 mg, 120 mg or 240 mg of febuxostat which is administered to a subject once a day) similar to or lower than the highest doses xanthine oxidoreductase inhibitors currently available (namely, currently available dosage (e.g., 80 mg (US) or 120 mg (Europe)) of 2-[3-cyano-4-(2-methylpropoxy)phenyl]-4-methylthiazole-5-carboxylic acid (which is also known as "febuxostat") or at least one xanthine oxidase inhibitor (for example, an immediate release dosage form containing 300 mg of allopurinol which is administered to a subject once a day). Second, because the dosage forms of the present disclosure provide for xanthine oxidoreductase inhibition or xanthine oxidase inhibition, for extended time (dosing) periods, these solid dosage forms can be used to treat a variety of different conditions or diseases, such as, but not limited to, gout, hyperuricemia, prostatitis, inflammatory bowel disease, QT interval prolongation, myocardial infarction, cardiac hypertrophy, hypertension, nephrolithiasis, renal impairment, chronic kidney disease, metabolic syndrome, diabetes, diabetic nephropathy, congestive heart failure and other disorders. Third, the modified release dosage forms of the present disclosure protect subjects receiving these dosage forms throughout their treatment regimen against increasing concentrations of oxygen free radicals.

In order to obtain these benefits, the modified release dosage forms of the present disclosure must achieve a certain pharmacokinetic profile when compared to immediate release xanthine oxidoreductase inhibitor or xanthine oxidase inhibitor dosage forms.

In one embodiment, the modified release dosage forms of the present disclosure containing at least one xanthine oxidoreductase inhibitor after oral administration to a subject in need of treatment thereof exhibit at least two of the following: (a) maintain in the subject a plasma concentration of xanthine oxidoreductase inhibitor or pharmaceutically acceptable salt thereof greater than about 0.1 µg/mL for a period of about 5 hours to about 24 hours; or (b) produce in the subject a maximum plasma concentration ($C_{max}$) of a xanthine oxidoreductase inhibitor or a pharmaceutically acceptable salt thereof in an amount of between about 2.5 µg/mL to about 0.5 µg/mL. In another embodiment, the modified release dosage forms of the present disclosure after oral administration to a subject in need of treatment thereof exhibit at least two of the following: (a) maintain in the subject a plasma concentration of xanthine oxidoreductase inhibitor or pharmaceutically acceptable salt thereof greater than about 0.1 µg/mL for a period of about 5 hours to about 24 hours; or (b) produce in the subject a maximum plasma concentration ($C_{max}$) of a xanthine oxidoreductase inhibitor or a pharmaceutically acceptable salt thereof of between about 2.0 µg/mL to about 1.0 µg/mL. In still yet another embodiment, the modified release dosage forms of the present disclosure after oral administration to a subject in need of treatment thereof exhibit each of the following: (a) maintain in the subject a plasma concentration of xanthine oxidoreductase inhibitor or pharmaceutically acceptable salt thereof greater than 0.1 µg/mL for a period of about 5 hours to about 24 hours; and (b) produce in the subject a about maximum plasma concentration ($C_{max}$) of a xanthine oxidoreductase inhibitor or a pharmaceutically acceptable salt thereof in an amount of between about 2.5 µg/mL to about 0.5 µg/mL.

As mentioned previously herein, the modified dosage forms of the present disclosure, after oral administration to a subject in need of treatment thereof, can maintain in the subject, a plasma concentration of xanthine oxidoreductase inhibitor or pharmaceutically acceptable salt thereof greater than about 0.1 µg/mL for a period of from about 5 to about 24 hours. More specifically, the modified dosage forms of the present disclosure after oral administration to a subject in need of treatment thereof, can maintain in the subject, a plasma concentration of xanthine oxidoreductase inhibitor or pharmaceutically acceptable salt thereof greater than about 0.1 µg/mL for a period for about 5.0 hours, for about 6.0 hours, for about 7.0 hours, for about 8.0 hours, for about 9.0 hours, for about 10.0 hours, for about 11.0 hours, for about 12.0 hours, for about 13.0 hours, for about 14.0 hours, for about 15.0 hours, for about 16.0 hours, for about 17.0 hours, for about 18.0 hours, for about 19.0 hours, for about 20.0 hours, for about 21.0 hours, for about 22.0 hours, for about 23.0 hours or for about 24.0 hours.

As also mentioned previously herein, the modified dosage forms of the present disclosure after oral administration to a subject in need of treatment thereof, can produce, in the subject, a maximum plasma concentration ($C_{max}$) of a xanthine oxidoreductase inhibitor or a pharmaceutically acceptable salt thereof in an amount of between about 2.5 µg/mL to about 0.5 µg/mL (as well as any combination of ranges in between, such as, for example, about 2.5 µg/mL to about 0.6 µg/mL, about 2.5 µg/mL to about 0.7 µg/mL, about 2.5 µg/mL to about 0.8 µg/mL, about 2.4 µg/mL to about 0.5 µg/mL, about 2.4 µg/mL to about 0.6 µg/mL, about 2.3 µg/mL to about 0.5 µg/mL, about 2.2 µg/mL to about 0.5 µg/mL, about 2.1 µg/mL to about 0.5 µg/mL, about 2.0 µg/mL to about 0.5 µg/mL, about 2.0 µg/mL to about 1.0 µg/mL, about 1.9 µg/mL to about 0.5 µg/mL, about 1.9 µg/mL to about 1.0 µg/mL, about 1.8 µg/mL to about 0.5 µg/mL, about 1.8 µg/mL to about 1.0 µg/mL, about 1.7 µg/mL to about 0.5 µg/mL, about 1.7 µg/mL to about 0.6 µg/mL, about 1.7 µg/mL to about 0.7 µg/mL, about 1.7 µg/mL to about 0.8 µg/mL, about 1.7 µg/mL to about 1.0

μg/mL, about 1.6 μg/mL to about 0.5 μg/mL, about 1.5 μg/mL to about 1.0 μg/mL etc.). More specifically, the modified dosage forms of the present disclosure can, after oral administration to a subject in need of treatment thereof, produce in the subject, a $C_{max}$ of a xanthine oxidoreductase inhibitor or a pharmaceutically acceptable salt thereof in an amount of about 2.5 μg/mL, about 2.4 μg/mL, about 2.3 μg/mL, about 2.2 μg/mL, about 2.1 μg/mL, 2.0 μg/mL about 1.9 μg/mL, about 1.8 μg/mL, about 1.7 μg/mL, about 1.6 μg/mL, about 1.5 μg/mL, about 1.4 μg/mL, about 1.3 μg/mL, about 1.2 μg/mL, about 1.1 μg/mL, about 1.0 μg/mL, about 0.9 μg/mL, about 0.8 μg/mL, about 0.7 μg/mL, about 0.6 μg/mL or about 0.5 μg/mL.

The dosage forms of the present disclosure can contain from about 5 mg to about 240 mg of at least one xanthine oxidoreductase inhibitor. More specifically, the dosage form can contain about 5 mg, about 6.25 mg, about 10 mg, about 20 mg, about 25 mg, about 30 mg, about 40 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg or about 240 mg of at least one xanthine oxidoreductase inhibitor.

In another embodiment, the modified release dosage forms of the present disclosure containing at least one xanthine oxidoreductase inhibitor after oral administration to a subject in need of treatment thereof exhibit at least two of the following: (a) maintain in the subject a plasma concentration of xanthine oxidoreductase inhibitor or pharmaceutically acceptable salt thereof greater than about 0.1 μg/mL for a period of about 5 hours to about 16 hours; or (b) produce in the subject a maximum plasma concentration ($C_{max}$) of a xanthine oxidoreductase inhibitor or a pharmaceutically acceptable salt thereof in an amount of between about 2.5 μg/mL to about 0.05 μg/mL. In yet another embodiment, the modified release dosage forms of the present disclosure after oral administration to a subject in need of treatment thereof exhibit at least two of the following: (a) maintain in the subject a plasma concentration of xanthine oxidoreductase inhibitor or pharmaceutically acceptable salt thereof greater than about 0.1 μg/mL for a period of about 5 hours to about 16 hours; or (b) produce in the subject a maximum plasma concentration ($C_{max}$) of a xanthine oxidoreductase inhibitor or a pharmaceutically acceptable salt thereof of between about 2.0 μg/mL to about 0.075 μg/mL. In still yet another embodiment, the modified release dosage forms of the present disclosure after oral administration to a subject in need of treatment thereof exhibit each of the following: (a) maintain in the subject a plasma concentration of xanthine oxidoreductase inhibitor or pharmaceutically acceptable salt thereof greater than 0.1 μg/mL for a period of about 5 hours to about 16 hours; and (b) produce in the subject a about maximum plasma concentration ($C_{max}$) of a xanthine oxidoreductase inhibitor or a pharmaceutically acceptable salt thereof in an amount of between about 2.5 μg/mL to about 0.05 μg/mL.

As mentioned previously herein, the modified dosage forms of the present disclosure, after oral administration to a subject in need of treatment thereof, can maintain in the subject, a plasma concentration of xanthine oxidoreductase inhibitor or pharmaceutically acceptable salt thereof greater than about 0.1 μg/mL for a period of from about 5 to about 16 hours. More specifically, the modified dosage forms of the present disclosure after oral administration to a subject in need of treatment thereof, can maintain in the subject, a plasma concentration of xanthine oxidoreductase inhibitor or pharmaceutically acceptable salt thereof greater than about 0.1 μg/mL for a period for about 5.0 hours, for about 6.0 hours, for about 7.0 hours, for about 8.0 hours, for about 9.0 hours, for about 10.0 hours, for about 11.0 hours, for about 12.0 hours, for about 13.0 hours, for about 14.0 hours, for about 15.0 hours, or for about 16.0 hours.

As also mentioned previously herein, the modified dosage forms of the present disclosure after oral administration to a subject in need of treatment thereof, can produce, in the subject, a maximum plasma concentration ($C_{max}$) of a xanthine oxidoreductase inhibitor or a pharmaceutically acceptable salt thereof in an amount of between about 2.5 μg/mL to about 0.05 μg/mL (as well as any combination of ranges in between, such as, for example, about 2.5 μg/mL to about 0.06 μg/mL, about 2.5 μg/mL to about 0.07 μg/mL, about 2.5 μg/mL to about 0.08 μg/mL, about 2.5 μg/mL to about 0.09 μg/mL, about 2.5 μg/mL to about 0.1 μg/mL, about 2.5 μg/mL to about 0.2 μg/mL, about 2.5 μg/mL to about 0.3 μg/mL, about 2.5 μg/mL to about 0.40 μg/mL, about 2.5 μg/mL to about 0.5 μg/mL about 2.5 μg/mL to about 0.6 μg/mL, about 2.5 μg/mL to about 0.7 μg/mL, about 2.5 μg/mL to about 0.8 μg/mL, about 2.5 μg/mL to about 0.9 μg/mL, about 2.5 μg/mL to about 1.0 μg/mL, 2.4 μg/mL to about 0.05 μg/mL, 2.4 μg/mL to about 0.06 μg/mL, about 2.4 μg/mL to about 0.07 μg/mL, about 2.4 μg/mL to about 0.08 μg/mL, about 2.4 μg/mL to about 0.09 μg/mL, about 2.4 μg/mL to about 0.1 μg/mL, about 2.4 μg/mL to about 0.2 μg/mL, about 2.4 μg/mL to about 0.3 μg/mL, about 2.4 μg/mL to about 0.40 μg/mL, about 2.4 μg/mL to about 0.5 μg/mL about 2.4 μg/mL to about 0.6 μg/mL, about 2.4 μg/mL to about 0.7 μg/mL, about 2.4 μg/mL to about 0.8 μg/mL, about 2.4 μg/mL to about 0.9 μg/mL, 2.4 μg/mL to about 1.0 μg/mL, 2.3 μg/mL to about 0.06 μg/mL, about 2.3 μg/mL to about 0.07 μg/mL, about 2.3 μg/mL to about 0.08 μg/mL, about 2.3 μg/mL to about 0.09 μg/mL, about 2.3 μg/mL to about 0.1 μg/mL, about 2.3 μg/mL to about 0.2 μg/mL, about 2.3 μg/mL to about 0.3 μg/mL, about 2.3 μg/mL to about 0.40 μg/mL, about 2.3 μg/mL to about 0.5 μg/mL about 2.3 μg/mL to about 0.6 μg/mL, about 2.3 μg/mL to about 0.7 μg/mL, about 2.3 μg/mL to about 0.8 μg/mL, about 2.3 μg/mL to about 0.9 μg/mL, about 2.3 μg/mL to about 1.0 μg/mL, 2.2 μg/mL to about 0.05 μg/mL, 2.2 μg/mL to about 0.06 μg/mL, about 2.2 μg/mL to about 0.07 μg/mL, about 2.2 μg/mL to about 0.08 μg/mL, about 2.2 μg/mL to about 0.09 μg/mL, about 2.2 μg/mL to about 0.1 μg/mL, about 2.2 μg/mL to about 0.2 μg/mL, about 2.2 μg/mL to about 0.3 μg/mL, about 2.2 μg/mL to about 0.40 μg/mL, about 2.2 μg/mL to about 0.5 μg/mL about 2.2 μg/mL to about 0.6 μg/mL, about 2.4 μg/mL to about 0.7 μg/mL, about 2.2 μg/mL to about 0.8 μg/mL, about 2.2 μg/mL to about 0.9 μg/mL, about 2.2 μg/mL to about 1.0 μg/mL, 2.1 μg/mL to about 0.05 μg/mL, 2.1 μg/mL to about 0.06 μg/mL, about 2.1 μg/mL to about 0.07 μg/mL, about 2.1 μg/mL to about 0.08 μg/mL, about 2.1 μg/mL to about 0.09 μg/mL, about 2.1 μg/mL to about 0.1 μg/mL, about 2.1 μg/mL to about 0.2 μg/mL, about 2.1 μg/mL to about 0.3 μg/mL, about 2.1 μg/mL to about 0.40 μg/mL, about 2.1 μg/mL to about 0.5 μg/mL about 2.1 μg/mL to about 0.6 μg/mL, about 2.1 μg/mL to about 0.7 μg/mL, about 2.1 μg/mL to about 0.8 μg/mL, about 2.1 μg/mL to about 0.9 μg/mL, about 2.1 μg/mL to about 1.0 μg/mL, 2.0 μg/mL to about 0.05 μg/mL, 2.0 μg/mL to about 0.06 μg/mL, about 2.0 μg/mL to about 0.07 μg/mL, about 2.0 μg/mL to about 0.08 μg/mL, about 2.0 μg/mL to about 0.09 μg/mL, about 2.0 μg/mL to about 0.1 μg/mL, about 2.0 μg/mL to about 0.2 μg/mL, about 2.0 μg/mL to about 0.3 μg/mL, about 2.0 μg/mL to about 0.40 μg/mL, about 2.0 μg/mL to about 0.5

µg/mL about 2.0 µg/mL to about 0.6 µg/mL, about 2.0 µg/mL to about 0.7 µg/mL, about 2.0 µg/mL to about 0.8 µg/mL, about 2.0 µg/mL to about 0.9 µg/mL, about 2.0 µg/mL to about 1.0 µg/mL, 1.9 µg/mL to about 0.05 µg/mL, 1.9 µg/mL to about 0.06 µg/mL, about 1.9 µg/mL to about 0.07 µg/mL, about 1.9 µg/mL to about 0.08 µg/mL, about 1.9 µg/mL to about 0.09 µg/mL, about 1.9 µg/mL to about 0.1 µg/mL, about 1.9 µg/mL to about 0.2 µg/mL, about 1.9 µg/mL to about 0.3 µg/mL, about 1.9 µg/mL to about 0.40 µg/mL, about 1.9 µg/mL to about 0.5 µg/mL about 1.9 µg/mL to about 0.6 µg/mL, about 1.9 µg/mL to about 0.7 µg/mL, about 1.9 µg/mL to about 0.8 µg/mL, about 1.9 µg/mL to about 0.9 µg/mL, about 1.9 µg/mL to about 1.0 µg/mL, 1.8 µg/mL to about 0.05 µg/mL, 1.8 µg/mL to about 0.06 µg/mL, about 1.8 µg/mL to about 0.07 µg/mL, about 1.8 µg/mL to about 0.08 µg/mL, about 1.8 µg/mL to about 0.09 µg/mL, about 1.8 µg/mL to about 0.1 µg/mL, about 1.8 µg/mL to about 0.2 µg/mL, about 1.8 µg/mL to about 0.3 µg/mL, about 1.8 µg/mL to about 0.40 µg/mL, about 1.8 µg/mL to about 0.5 µg/mL about 1.8 µg/mL to about 0.6 µg/mL, about 1.8 µg/mL to about 0.7 µg/mL, about 1.8 µg/mL to about 0.8 µg/mL, about 1.8 µg/mL to about 0.9 µg/mL, about 1.8 µg/mL to about 1.0 µg/mL, 1.7 µg/mL to about 0.05 µg/mL, 1.7 µg/mL to about 0.06 µg/mL, about 1.7 µg/mL to about 0.07 µg/mL, about 1.7 µg/mL to about 0.08 µg/mL, about 1.7 µg/mL to about 0.09 µg/mL, about 1.7 µg/mL to about 0.1 µg/mL, about 1.7 µg/mL to about 0.2 µg/mL, about 1.7 µg/mL to about 0.3 µg/mL, about 1.7 µg/mL to about 0.40 µg/mL, about 1.7 µg/mL to about 0.5 µg/mL about 1.7 µg/mL to about 0.6 µg/mL, about 1.7 µg/mL to about 0.7 µg/mL, about 1.7 µg/mL to about 0.8 µg/mL, about 1.7 µg/mL to about 0.9 µg/mL, about 1.7 µg/mL to about 1.0 µg/mL, 1.6 µg/mL to about 0.05 µg/mL, 1.6 µg/mL to about 0.06 µg/mL, about 1.6 µg/mL to about 0.07 µg/mL, about 1.6 µg/mL to about 0.08 µg/mL, about 1.6 µg/mL to about 0.09 µg/mL, about 1.6 µg/mL to about 0.1 µg/mL, about 1.6 µg/mL to about 0.2 µg/mL, about 1.6 µg/mL to about 0.3 µg/mL, about 1.6 µg/mL to about 0.40 µg/mL, about 1.6 µg/mL to about 0.5 µg/mL about 1.6 µg/mL to about 0.6 µg/mL, about 1.6 µg/mL to about 0.7 µg/mL, about 1.6 µg/mL to about 0.8 µg/mL, about 1.6 µg/mL to about 0.9 µg/mL, about 1.6 µg/mL to about 1.0 µg/mL, 1.5 µg/mL to about 0.05 µg/mL, 1.5 µg/mL to about 0.06 µg/mL, about 1.5 µg/mL to about 0.07 µg/mL, about 1.5 µg/mL to about 0.08 µg/mL, about 1.5 µg/mL to about 0.09 µg/mL, about 1.5 µg/mL to about 0.1 µg/mL, about 1.5 µg/mL to about 0.2 µg/mL, about 1.5 µg/mL to about 0.3 µg/mL, about 1.5 µg/mL to about 0.40 µg/mL, about 1.5 µg/mL to about 0.5 µg/mL about 1.5 µg/mL to about 0.6 µg/mL, about 1.5 µg/mL to about 0.7 µg/mL, about 1.5 µg/mL to about 0.8 µg/mL, about 1.5 µg/mL to about 0.9 µg/mL or about 1.5 µg/mL to about 1.0 µg/mL. More specifically, the modified dosage forms of the present disclosure can, after oral administration to a subject in need of treatment thereof, produce in the subject, a $C_{max}$ of a xanthine oxidoreductase inhibitor or a pharmaceutically acceptable salt thereof in an amount of 2.5 µg/mL, about 2.4 µg/mL, about 2.3 µg/mL, about 2.2 µg/mL, about 2.1 µg/mL, 2.0 µg/mL about 1.9 µg/mL, about 1.8 µg/mL, about 1.7 µg/mL, about 1.6 µg/mL, about 1.5 µg/mL, about 1.4 µg/mL, about 1.3 µg/mL, about 1.2 µg/mL, about 1.1 µg/mL, about 1.0 µg/mL, about 0.9 µg/mL, about 0.8 µg/mL, about 0.7 µg/mL, about 0.6 µg/mL, about 0.5 µg/mL, about 0.4 µg/mL, about 0.3 µg/mL, about 0.2 µg/mL, about 0.1 µg/mL, about 0.099 µg/mL, about 0.098 µg/mL, about 0.097 µg/mL, about 0.096 µg/mL, about 0.095 µg/mL, about 0.094 µg/mL, about 0.093 µg/mL, about 0.092 µg/mL, about 0.091 µg/mL, about 0.090 µg/mL, about 0.089 µg/mL, about 0.088 µg/mL, about 0.087 µg/mL, about 0.086 µg/mL, about 0.085 µg/mL, about 0.084 µg/mL, about 0.083 µg/mL, about 0.082 µg/mL, about 0.081 µg/mL, about 0.080 µg/mL, about 0.079 µg/mL, about 0.078 µg/mL, about 0.077 µg/mL, about 0.076 µg/mL, about 0.075 µg/mL, about 0.074 µg/mL, about 0.073 µg/mL, about 0.072 µg/mL, about 0.071 µg/mL, about 0.070 µg/mL, about 0.069 µg/mL, about 0.068 µg/mL, about 0.067 µg/mL, about 0.066 µg/mL, about 0.065 µg/mL, about 0.064 µg/mL, about 0.063 µg/mL, about 0.062 µg/mL, about 0.061 µg/mL, about 0.060 µg/mL, about 0.059 µg/mL, about 0.058 µg/mL, about 0.057 µg/mL, about 0.056 µg/mL, about 0.055 µg/mL, about 0.054 µg/mL, about 0.053 µg/mL, about 0.052 µg/mL, about 0.051 µg/mL or about 0.050 µg/mL.

The dosage forms of the present disclosure can contain from about 5 mg to about 240 mg of at least one xanthine oxidoreductase inhibitor. More specifically, the dosage form can contain about 5 mg, about 6.25 mg, about 10 mg, about 20 mg, about 25 mg, about 30 mg, about 40 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg or about 240 mg of at least one xanthine oxidoreductase inhibitor.

In yet another embodiment, the modified release dosage forms of the present disclosure containing at least one xanthine oxidoreductase inhibitor after oral administration to a subject in need of treatment thereof exhibit at least two of the following: (a) maintain in the subject a plasma concentration of xanthine oxidoreductase inhibitor or pharmaceutically acceptable salt thereof greater than about 0.1 µg/mL for a period of about 5 hours to about 14 hours; or (b) produce in the subject a maximum plasma concentration ($C_{max}$) of a xanthine oxidoreductase inhibitor or a pharmaceutically acceptable salt thereof in an amount of between about 2.5 µg/mL to about 0.090 µg/mL. In yet another embodiment, the modified release dosage forms of the present disclosure after oral administration to a subject in need of treatment thereof exhibit at least two of the following: (a) maintain in the subject a plasma concentration of xanthine oxidoreductase inhibitor or pharmaceutically acceptable salt thereof greater than about 0.1 µg/mL for a period of about 5 hours to about 14 hours; or (b) produce in the subject a maximum plasma concentration ($C_{max}$) of a xanthine oxidoreductase inhibitor or a pharmaceutically acceptable salt thereof of between about 2.0 µg/mL to about 0.095 µg/mL. In still yet another embodiment, the modified release dosage forms of the present disclosure after oral administration to a subject in need of treatment thereof exhibit each of the following: (a) maintain in the subject a plasma concentration of xanthine oxidoreductase inhibitor or pharmaceutically acceptable salt thereof greater than 0.1 µg/mL for a period of about 5 hours to about 14 hours; and (b) produce in the subject a about maximum plasma concentration ($C_{max}$) of a xanthine oxidoreductase inhibitor or a pharmaceutically acceptable salt thereof in an amount of between about 2.5 µg/mL to about 0.090 µg/mL.

As mentioned previously herein, the modified dosage forms of the present disclosure, after oral administration to a subject in need of treatment thereof, can maintain in the subject, a plasma concentration of xanthine oxidoreductase inhibitor or pharmaceutically acceptable salt thereof greater than about 0.1 µg/mL for a period of from about 5 to about 14 hours. More specifically, the modified dosage forms of the present disclosure after oral administration to a subject in need of treatment thereof, can maintain in the subject, a plasma concentration of xanthine oxidoreductase inhibitor or pharmaceutically acceptable salt thereof greater than about 0.1 µg/mL for a period for about 5.0 hours, for about 6.0 hours, for about 7.0 hours, for about 8.0 hours, for about 9.0 hours, for about 10.0 hours, for about 11.0 hours, for about 12.0 hours, for about 13.0 hours or for about 14.0 hours.

As also mentioned previously herein, the modified dosage forms of the present disclosure after oral administration to a subject in need of treatment thereof, can produce, in the subject, a maximum plasma concentration ($C_{max}$) of a xanthine oxidoreductase inhibitor or a pharmaceutically acceptable salt thereof in an amount of between about 2.5 µg/mL to about 0.090 µg/mL (as well as any combination of ranges in between, such as, for example, about 2.5 µg/mL to about 0.1 µg/mL, about 2.5 µg/mL to about 0.2 µg/mL, about 2.5 µg/mL to about 0.3 µg/mL, about 2.5 µg/mL to about 0.40 µg/mL, about 2.5 µg/mL to about 0.5 µg/mL about 2.5 µg/mL to about 0.6 µg/mL, about 2.5 µg/mL to about 0.7 µg/mL, about 2.5 µg/mL to about 0.8 µg/mL, about 2.5 µg/mL to about 0.9 µg/mL, about 2.5 µg/mL to about 1.0 µg/mL, about 2.4 µg/mL to about 0.1 µg/mL, about 2.4 µg/mL to about 0.1 µg/mL, about 2.4 µg/mL to about 0.2 µg/mL, about 2.4 µg/mL to about 0.3 µg/mL, about 2.4 µg/mL to about 0.40 µg/mL, about 2.4 µg/mL to about 0.5 µg/mL about 2.4 µg/mL to about 0.6 µg/mL, about 2.4 µg/mL to about 0.7 µg/mL, about 2.4 µg/mL to about 0.8 µg/mL, about 2.4 µg/mL to about 0.9 µg/mL, 2.4 µg/mL to about 1.0 µg/mL, about 2.3 µg/mL to about 0.1 µg/mL, about 2.3 µg/mL to about 0.2 µg/mL, about 2.3 µg/mL to about 0.3 µg/mL, about 2.3 µg/mL to about 0.40 µg/mL, about 2.3 µg/mL to about 0.5 µg/mL about 2.3 µg/mL to about 0.6 µg/mL, about 2.3 µg/mL to about 0.7 µg/mL, about 2.3 µg/mL to about 0.8 µg/mL, about 2.3 µg/mL to about 0.9 µg/mL, about 2.3 µg/mL to about 1.0 µg/mL, about 2.2 µg/mL to about 0.1 µg/mL, about 2.2 µg/mL to about 0.2 µg/mL, about 2.2 µg/mL to about 0.3 µg/mL, about 2.2 µg/mL to about 0.40 µg/mL, about 2.2 µg/mL to about 0.5 µg/mL about 2.2 µg/mL to about 0.6 µg/mL, about 2.4 µg/mL to about 0.7 µg/mL, about 2.2 µg/mL to about 0.8 µg/mL, about 2.2 µg/mL to about 0.9 µg/mL, about 2.2 µg/mL to about 1.0 µg/mL, about 2.1 µg/mL to about 0.1 µg/mL, about 2.1 µg/mL to about 0.2 µg/mL, about 2.1 µg/mL to about 0.3 µg/mL, about 2.1 µg/mL to about 0.40 µg/mL, about 2.1 µg/mL to about 0.5 µg/mL about 2.1 µg/mL to about 0.6 µg/mL, about 2.1 µg/mL to about 0.7 µg/mL, about 2.1 µg/mL to about 0.8 µg/mL, about 2.1 µg/mL to about 0.9 µg/mL, about 2.1 µg/mL to about 1.0 µg/mL, about 2.0 µg/mL to about 0.1 µg/mL, about 2.0 µg/mL to about 0.2 µg/mL, about 2.0 µg/mL to about 0.3 µg/mL, about 2.0 µg/mL to about 0.40 µg/mL, about 2.0 µg/mL to about 0.5 µg/mL about 2.0 µg/mL to about 0.6 µg/mL, about 2.0 µg/mL to about 0.7 µg/mL, about 2.0 µg/mL to about 0.8 µg/mL, about 2.0 µg/mL to about 0.9 µg/mL, about 2.0 µg/mL to about 1.0 µg/mL, about 1.9 µg/mL to about 0.1 µg/mL, about 1.9 µg/mL to about 0.2 µg/mL, about 1.9 µg/mL to about 0.3 µg/mL, about 1.9 µg/mL to about 0.40 µg/mL, about 1.9 µg/mL to about 0.5 µg/mL about 1.9 µg/mL to about 0.6 µg/mL, about 1.9 µg/mL to about 0.7 µg/mL, about 1.9 µg/mL to about 0.8 µg/mL, about 1.9 µg/mL to about 0.9 µg/mL, about 1.9 µg/mL to about 1.0 µg/mL, about 1.8 µg/mL to about 0.1 µg/mL, about 1.8 µg/mL to about 0.2 µg/mL, about 1.8 µg/mL to about 0.3 µg/mL, about 1.8 µg/mL to about 0.40 µg/mL, about 1.8 µg/mL to about 0.5 µg/mL about 1.8 µg/mL to about 0.6 µg/mL, about 1.8 µg/mL to about 0.7 µg/mL, about 1.8 µg/mL to about 0.8 µg/mL, about 1.8 µg/mL to about 0.9 µg/mL, about 1.8 µg/mL to about 1.0 µg/mL, 1.7 µg/mL to about 0.05 µg/mL, about 1.7 µg/mL to about 0.1 µg/mL, about 1.7 µg/mL to about 0.2 µg/mL, about 1.7 µg/mL to about 0.3 µg/mL, about 1.7 µg/mL to about 0.40 µg/mL, about 1.7 µg/mL to about 0.5 µg/mL about 1.7 µg/mL to about 0.6 µg/mL, about 1.7 µg/mL to about 0.7 µg/mL, about 1.7 µg/mL to about 0.8 µg/mL, about 1.7 µg/mL to about 0.9 µg/mL, about 1.7 µg/mL to about 1.0 µg/mL, 1.6 µg/mL to about 0.1 µg/mL, about 1.6 µg/mL to about 0.2 µg/mL, about 1.6 µg/mL to about 0.3 µg/mL, about 1.6 µg/mL to about 0.40 µg/mL, about 1.6 µg/mL to about 0.5 µg/mL about 1.6 µg/mL to about 0.6 µg/mL, about 1.6 µg/mL to about 0.7 µg/mL, about 1.6 µg/mL to about 0.8 µg/mL, about 1.6 µg/mL to about 0.9 µg/mL, about 1.6 µg/mL to about 1.0 µg/mL, about 1.5 µg/mL to about 0.1 µg/mL, about 1.5 µg/mL to about 0.2 µg/mL, about 1.5 µg/mL to about 0.3 µg/mL, about 1.5 µg/mL to about 0.40 µg/mL, about 1.5 µg/mL to about 0.5 µg/mL about 1.5 µg/mL to about 0.6 µg/mL, about 1.5 µg/mL to about 0.7 µg/mL, about 1.5 µg/mL to about 0.8 µg/mL, about 1.5 µg/mL to about 0.9 µg/mL or about 1.5 µg/mL to about 1.0 µg/mL. More specifically, the modified dosage forms of the present disclosure can, after oral administration to a subject in need of treatment thereof, produce in the subject, a $C_{max}$ of a xanthine oxidoreductase inhibitor or a pharmaceutically acceptable salt thereof in an amount of 2.5 µg/mL, about 2.4 µg/mL, about 2.3 µg/mL, about 2.2 µg/mL, about 2.1 µg/mL, 2.0 µg/mL about 1.9 µg/mL, about 1.8 µg/mL, about 1.7 µg/mL, about 1.6 µg/mL, about 1.5 µg/mL, about 1.4 µg/mL, about 1.3 µg/mL, about 1.2 µg/mL, about 1.1 µg/mL, about 1.0 µg/mL, about 0.9 µg/mL, about 0.8 µg/mL, about 0.7 µg/mL, about 0.6 µg/mL, about 0.5 µg/mL, about 0.4 µg/mL, about 0.3 µg/mL, about 0.2 µg/mL, about 0.1 µg/mL, about 0.099 µg/mL, about 0.098 µg/mL, about 0.097 µg/mL, about 0.096 µg/mL, about 0.095 µg/mL, about 0.094 µg/mL, about 0.093 µg/mL, about 0.092 µg/mL, about 0.091 µg/mL or about 0.090 µg/mL.

The dosage forms of the present disclosure can contain from about 5 mg to about 240 mg of at least one xanthine oxidoreductase inhibitor. More specifically, the dosage form can contain about 5 mg, about 6.25 mg, about 10 mg, about 20 mg, about 25 mg, about 30 mg, about 40 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg or about 240 mg of at least one xanthine oxidoreductase inhibitor.

Methods for determining the $C_{max}$ of xanthine oxidoreductase inhibitors and the plasma concentration of xanthine oxidoreductase inhibitors are well known in the art. In order to determine the percentage of inhibition of xanthine oxidoreductase exhibited by a dosage form, the following equation can be used:

Percent Inhibition ("% Inhibition") of xanthine oxidoreductase activity:

$$\% \text{ Inhibition of xanthine oxidoreductase} = 100 \frac{C \cdot f_u}{C \cdot f_u + K_i}$$

where C=plasma concentration of xanthine oxidoreductase inhibitor ("XORI") in plasma of a subject, $f_u$=the free fraction of XORI in plasma and $K_i$=the xanthine oxidoreductase inhibitory constant of XORI.

The plasma concentration of XORI can be determined using techniques known in the art such as high performance liquid chromatography with fluorescence detection or validated high performance liquid chromatography tandem mass spectrometry (See Mayer, M. et al., *American Journal of Therapeutics*, 12:22-34 (2005)). The $f_u$ can be determined using the in-vitro binding of $^{14}C$ XORI at a nominal concentration of 1 μg/mL using an equilibrium dialysis technique, which is well known in the art. For example, the $f_u$ for a XORI such as febuxostat has been calculated to be 0.9±0.2 in normal patients and 1.2±0.2 in patients with severe renal impairment (See Mayer, M. et al., *American Journal of Therapeutics*, 12:22-34 (2005)). In another study with a larger number of subjects, the percent free fraction of febuxostat in plasma was calculated to be 0.7±0.1 in male, female, younger, and an elderly group of subjects (See Khosravan R., et al, *Clinic. Pharmacology & Therapeutics*, P50 (2005)).

The $K_i$ for XORIs can be determined using routine techniques known in the art. For example, the Ki for a XORI such as febuxostat has been determined using a xanthine oxidase assay such as that described in Osada Y., et al., *European J. Pharmacology*, 241:183-188 (1993). More specifically, the $K_i$ for febuxostat has been determined to be 0.7 nM and 0.6 nM, respectively (See, Osada Y., et al., *European J. Pharmacology*, 241:183-188 (1993) and Takano, Y., et al., *Life Sciences*, 76:1835-1847 (2005)).

In still yet another embodiment, the modified release dosage forms of the present disclosure contain at least one xanthine oxidase inhibitor. These modified release dosage forms containing at least one xanthine oxidase inhibitor, after oral administration to a subject, are expected to maintain critical concentration in plasma for longer durations compared to immediate release formulations containing allopurinol thereby inhibiting target enzyme for a prolonged period of time. Thus, these modified release dosage forms will be advantageous over immediate release tablets since these modified release dosage forms would reduce inter-patient variability due to variation of half life of oxypurinol and allopurinol, thereby improving therapeutic outcome.

The dosage forms of the present disclosure can contain, in addition to a xanthine oxidoreductase inhibitor or xanthine oxidase inhibitor, other drugs. These other drugs may be selected from any of the various classes of agents including, but not limited to, non-steroidal anti-inflammatory agents, analgesic agents, anesthetic agents, anti-anginal agents, anti-arthritic agents, anti-arrhythmic agents, antiasthmatic agents, antibacterial agents, anti-BPH agents, anticancer agents, anticholinergic agents, anticoagulants, anticonvulsants, antidepressants, antidiabetic agents, antidiarrheals, anti-epileptic agents, antifungal agents, antigout agents, antihelminthic agents, antihistamines, antihypertensive agents, antiinflammatory agents, antimalarial agents, antimigraine agents, antimuscarinic agents, antinauseants, antineoplastic agents, anti-obesity agents, antiosteoporosis agents, antiparkinsonism agents, antiprotozoal agents, antipruritics, antipsychotic agents, antipyretics, antispasmodics, antithyroid agents, antitubercular agents, antiulcer agents, anti-urinary incontinence agents, antiviral agents, anxiolytics, appetite suppressants, attention deficit disorder (ADD) and attention deficit hyperactivity disorder (ADHD) drugs, calcium channel blockers, cardiac inotropic agents, beta-blockers, central nervous system stimulants, cognition enhancers, corticosteroids, COX-2 inhibitors, decongestants, diuretics, gastrointestinal agents, genetic materials, drugs used in the management of gout (such as colchine; uricosuric agents such as probenecid, sulfinpyrazone, benziodarone; xanthine oxidase inhibitors such as oxypurinol, allopurinol, etc) histamine receptor antagonists, hormonolytics, hypnotics, hypoglycemic agents, immunosuppressants, keratolytics, leukotriene inhibitors, lipid-regulating agents, macrolides, mitotic inhibitors, muscle relaxants, narcotic antagonists, neuroleptic agents, nicotine, nutritional oils, xanthine derivatives (such as, but not limited to, caffeine and derivatives of caffeine), parasympatholytic agents, sedatives, sex hormones, sympathomimetic agents, tranquilizers, vasodilators, vitamins, and combinations thereof. Any of the aforementioned drugs may also be administered in combination with the xanthine oxidoreductase inhibitors or xanthine oxidase inhibitors used in the dosage forms of the present disclosure.

The benefits of the present disclosure are not limited to a single type of dosage form having a particular mechanism of drug release. This enhanced pharmacokinetic profile can be obtained with any of oral extended dosage form known in the art, such as, but not limited to, a pulsatile release dosage form, an extended release dosage form or a delayed release dosage form, following the teachings above.

Many different types of oral polymeric modified release dosages forms are known in the art and are contemplated for use in the present disclosure. Examples of three different types of oral polymeric modified release dosage forms, such as, matrix systems, osmotic pumps or membrane controlled technology (also referred to as reservoir system), are described in greater detail below. A detailed discussion of these dosage forms may also be found in: (i) *Handbook of pharmaceutical controlled release technology*, ed. D. L. Wise, Marcel Dekker, Inc. New York, N.Y. (2000), and (ii). Treatise on controlled drug delivery, fundamentals, optimization, and applications, ed. A. Kydonieus, Marcel Dekker, Inc. New York, N.Y. (1992), the contents of each which is hereby incorporated by reference. However, although these three oral polymeric modified release dosage forms are described in greater detail, other modified release dosage forms known to those skilled in the art are contemplated to be within the scope of the present disclosure.

Matrix Systems

Matrix systems are well known in the art. In a matrix system, the drug is homogeneously dispersed in a polymer in association with conventional excipients. This admixture is typically compressed under pressure to produce a tablet. Drug is released from this tablet by diffusion and erosion. Matrix systems are described in detail by Wise and Kydonieus, supra.

The matrix dosage forms of the present disclosure can comprise a xanthine oxidoreductase inhibitor or xanthine oxidase inhibitor and a pharmaceutically acceptable polymer. In one aspect, the xanthine oxidoreductase inhibitor is 2-[3-cyano-4-2(2-methylpropoxy)phenyl]-4-methylthiazole-5-carboxylic acid. In another aspect, the xanthine oxidase inhibitor is allopurinol.

The pharmaceutically acceptable polymer is a water-soluble hydrophilic polymer, or a water insoluble hydrophobic polymer (including waxes). Examples of suitable water soluble polymers include polyvinylpyrrolidine, hydroxypropylcellulose, hydroxypropyl methylcellulose, methyl cellulose, vinyl acetate copolymers, polysaccharides (such as alignate, xanthan gum, etc.), polyethylene oxide, methacrylic acid copolymers, maleic anhydride/methyl vinyl ether copolymers and derivatives and mixtures thereof. Examples of suitable water insoluble polymers include acrylates, cellulose derivatives such ethylcellulose or cellulose acetate, polyethylene, methacrylates, acrylic acid copolymers and high molecular weight polyvinylalcohols. Examples of suitable waxes include fatty acids and glycerides.

In one aspect, the polymer is selected from hydroxypropyl cellulose, hydroxypropyl methylcellulose, and methyl cellulose. In another aspect, the polymer is hydroxypropyl methylcellulose. In still yet another aspect, the polymer is a high viscosity hydroxypropyl-methyl cellulose with viscosity ranging from about 4,000 cps to about 100,000 cps. The most preferred high viscosity polymer is a hydroxypropyl methylcellulose with a viscosity of about 15,000 cps, commercially available under the tradename, Methocel®, from The Dow Chemical Company.

The amount of the polymer in the dosage form generally varies from about 10% to about 70% by weight of the composition.

The dosage forms of the present disclosure will typically include pharmaceutically acceptable excipients. As is well known to those skilled in the art, pharmaceutical excipients are routinely incorporated into solid dosage forms. This is done to ease the manufacturing process as well as to improve the performance of the dosage form. Common excipients include diluents or bulking agents, lubricants, binders, etc. Such excipients can be used in the dosage forms of the present disclosure.

Diluents, or fillers, can be added in order to increase the mass of an individual dose to a size suitable for tablet compression. Suitable diluents include powdered sugar, calcium phosphate, calcium sulfate, microcrystalline cellulose, lactose, mannitol, kaolin, sodium chloride, dry starch, sorbitol, etc.

Lubricants can be incorporated into the dosage form for a variety of reasons. Lubricants reduce friction between the granulation and die wall during compression and ejection. This prevents the granulate from sticking to the tablet punches, facilitates its ejection from the tablet punches, etc. Examples of suitable lubricants that can be used include, but are not limited to, talc, stearic acid, vegetable oil, calcium stearate, zinc stearate, magnesium stearate, etc.

Glidants can also be incorporated into the dosage form. A glidant improves the flow characteristics of the granulation. Examples of suitable glidant's include, but are not limited to, talc, silicon dioxide and cornstarch.

Binders can be incorporated into the dosage form. Binders are typically utilized if the manufacture of the dosage form includes a granulation step. Examples of suitable binders include, but are not limited to, povidone, polyvinylpyrrolidone, xanthan gum, cellulose gums such as carboxymethylcellulose, methylcellulose, hydroxyethyl cellulose, hydroxypropyl cellulose, hydroxypropyl methylcellulose, hydroxycellulose, gelatin, starch, and pregelatinized starch.

Other excipients that can be incorporated into the dosage form include, but are not limited to, preservatives, antioxidants, or any other excipient commonly used in the pharmaceutical industry, etc. The amount of excipients used in the dosage form will correspond to that typically used in a matrix system. The total amount of excipients, fillers and extenders, etc. can vary from about 10% to about 70% by weight of the dosage form.

The matrix dosage forms are generally prepared using standard techniques well known in the art. Typically, they are prepared by dry blending the polymer, filler, the xanthine oxidoreductase inhibitor, such as, 2-[3-cyano-4-2(2-methylpropoxy)phenyl]-4-methylthiazole-5-carboxylic acid, or xanthine oxidase inhibitor, such as allopurinol and oxypurinol, and other excipients followed by granulating the mixture using an alcohol until proper granulation is obtained. The granulation is done by methods known in the art. The wet granules are dried in a fluid bed dryer, sifted and ground to appropriate size. Lubricating agents are mixed with the dried granulation to obtain the final dosage form.

Alternatively, the matrix dosage forms can be made using direct compression of a powdered, crystalline or granular composition containing the active agent(s), alone or in combination with one or more carriers, additives, or the like. Methods of direct compression are well known in the art.

The dosage forms of the present disclosure can be administered orally in the form of tablets, pills, or the granulate may be loose filled into capsules. The tablets can be prepared by techniques known in the art and contain a therapeutically effective amount of the xanthine oxidoreductase inhibitor or xanthin oxidase inhibitor and such excipients as are necessary to form the tablet by such techniques. Tablets and pills can additionally be prepared with enteric coatings and other release-controlling coatings for the purpose of acid protection, easing swallow ability, etc. The coating may be colored with a pharmaceutically accepted dye. The amount of dye and other excipients in the coating liquid may vary and will not impact the performance of the modified release tablets. The coating liquid generally comprises film forming polymers such as, but not limited to, hydroxypropyl cellulose, hydroxypropyl methylcellulose, cellulose esters or ethers (such as cellulose acetate or ethylcellulose), an acrylic polymer or a mixture of polymers. The coating solution is generally an aqueous solution or an organic solvent further comprising propylene glycol, sorbitan monoleate, sorbic acid, fillers such as titanium dioxide, and a pharmaceutically acceptable dye.

Osmotic Pumps

In an osmotic pump system, a tablet core is encased by a semipermeable membrane having at least one orifice. The semipermeable membrane is permeable to water, but impermeable to the drug. When the system is exposed to body fluids, water will penetrate through the semipermeable membrane into the tablet core containing osmotic excipients and the active drug. Osmotic pressure increases within the dosage form and drug is released through the orifice in an attempt to equalize pressure.

In more complex pumps, the tablet core contains two internal compartments. The first compartment contains the drug. The second compartment contains a polymer which swells on contact with fluid. After ingestion, this polymer swells into the drug containing compartment at a predetermined rate and forces drug from the dosage form at that rate. Such dosage forms are often used when a zero order release profile is desired.

Osmotic pumps are well known in the art and have been described in the literature. U.S. Pat. Nos. 4,088,864; 4,200,098; and 5,573,776; all of which are hereby incorporated by reference, describe osmotic pumps and methods for their manufacture.

As a general guideline, the osmotic pumps of the present disclosure can be formed by compressing a tablet of an osmotically active drug (or an osmotically inactive drug in combination with an osmotically active agent or osmagent) and then coating the tablet with a semipermeable membrane which is permeable to an exterior aqueous-based fluid but impermeable to the passage of drug and/or osmagent. One or more delivery orifices may be drilled through the semipermeable membrane wall. Alternatively, orifice(s) through the wall may be formed in situ by incorporating leachable pore forming materials in the wall. In operation, the exterior aqueous based fluid is imbibed through the semipermeable membrane wall and contacts the drug and/or salt to form a solution or suspension of the drug. The drug solution or suspension is then pumped out through the orifice as fresh fluid is imbibed through the semipermeable membrane.

In one embodiment, the tablet contains two distinct compartments. The first compartment contains the drug as described above. The second compartment contains an expandable driving member consisting of a layer of a swellable hydrophilic polymer, which operates to diminish the volume occupied by the drug, thereby delivering the drug from the device at a controlled rate over an extended period of time.

Typical materials for the semipermeable membrane include semipermeable polymers known to the art as osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethyl aminoacetate, cellulose acetate ethyl carbamate, cellulose acetate chloracetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876; 3,276,586; 3,541,005; 3,541,006; and 3,546,142, semipermeable polymers as disclosed by Loeb and Sourirajan in U.S. Pat. No. 3,133,132, lightly cross-linked polystyrene derivatives, cross-linked poly(sodium styrene sulfonate), poly(vinylbenzyltrimethyl ammonium chloride), cellulose acetate having a degree of substitution up to 1 and an acetyl content up to 50%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 4,160,020.

The osmotic agent present in the pump, which may be used when the drug itself is not osmotically active, are osmotically effective compounds soluble in the fluid that enters the device, and exhibits an osmotic pressure gradient across the semipermeable wall against the exterior fluid. Osmotically effective osmagents useful for the present purpose include, but are not limited to, magnesium sulfate, calcium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, hydrophilic polymers such as cellulose polymers, mixtures thereof, and the like. The osmagent is usually present in an excess amount, and it can be in any physical form, such as particle, powder, granule, and the like. The osmotic pressure in atmospheres of the osmagents suitable for the disclosure will be greater than zero and generally up to about 500 atm, or higher.

The expandable driving member is typically a swellable, hydrophilic polymer which interacts with water and aqueous biological fluids and swells or expands to an equilibrium state. The polymers exhibit the ability to swell in water and retain a significant portion of the imbibed water within the polymer structure. The polymers swell or expand to a very high degree, usually exhibiting a 2 to 50 fold volume increase. The polymers can be noncross-linked or cross-linked. The swellable, hydrophilic polymers can be lightly cross-linked, such cross-links being formed by covalent ionic bonds or hydrogen bonds. The polymers can be of plant, animal or synthetic origin. Hydrophilic polymers suitable for use in the present disclosure include, but are not limited to, poly(hydroxy alkyl methacrylate) having a molecular weight of from 30,000 to 5,000,000; kappa carrageenan, polyvinylpyrrolidone having molecular weight of from 10,000 to 360,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methyl cellulose; cross-linked agar and carboxymethyl cellulose; a water insoluble, water swellable copolymer produced by forming a dispersion of finely divided copolymer of maleic anhydride with styrene, ethylene, propylene, butylene or isobutylene cross-linked with from 0.001 to about 0.5 moles of saturated cross-linking agent per mole of maleic anhydride in copolymer; water swellable polymers of N-vinyl lactams, and the like.

The expression "orifice" as used herein comprises means and methods suitable for releasing the drug from the system. The expression includes one or more apertures or orifices which have been bored through the semipermeable membrane by mechanical procedures. Alternatively, it may be formed by incorporating an erodible element, such as a gelatin plug, in the semipermeable membrane. In cases where the semipermeable membrane is sufficiently permeable to the passage of drug, the pores in the membrane may be sufficient to release the agent/drug in therapeutically effective amounts. In such cases, the expression "passageway" refers to the pores within the membrane wall even though no bore or other orifice has been drilled therethrough. A detailed description of osmotic passageways and the maximum and minimum dimensions for a passageway are disclosed in U.S. Pat. Nos. 3,845,770 and 3,916,899, the disclosures of which are incorporated herein by reference.

The osmotic pumps of the present disclosure can be manufactured by standard techniques. For example, in one embodiment, the drug and other ingredients that may be housed in one area of the compartment adjacent to the passageway, are pressed into a solid possessing dimension that corresponds to the internal dimensions of the area of the compartment the agent will occupy, or the agent and other ingredients and a solvent are mixed into a solid or semisolid form by conventional methods such as ballmilling, calendaring, stirring or rollmilling, and then pressed into a preselected shape. Next, a layer of a hydrophilic polymer is placed in contact with the layer of agent in a like manner, and the two layers surrounded with a semipermeable wall. The layering of agent formulation and hydrophilic polymer can be fabricated by conventional two-layer press techniques. The wall can be applied by molding, spraying or dipping the pressed shapes into a wall forming material. Another technique that can be use for applying the wall is the air suspension procedure. This procedure consists of suspending and tumbling the pressed agent and dry hydrophilic polymer in a current of air and a wall forming composition until the wall is applied to the agent-hydrophilic polymer composite. The air suspension procedure is described in U.S. Pat. No. 2,799,241; *J. Am. Pharm. Assoc.*, Vol. 48, pp. 451-459, (1979). Other standard manufacturing procedures are described in *Modern Plastics Encyclopedia*, Vol. 46, pp. 62-70 (1969); and in *Pharmaceutical Sciences*, by Remington, Fourteenth Edition, pp. 1626-1678 (1970), published by Mack Publishing Company, Easton, Pa.

Reservoir Polymeric Systems

Reservoir systems are well known in the art. This technology is also commonly referred to as microencapsulation, bead technology or coated tablets. Small particles of the drug are encapsulated with pharmaceutically acceptable polymer(s). This polymer, and its relative quantity, offers a predetermined resistance to drug diffusion from the reservoir to the gastrointestinal tract. Thus, the drug is gradually released from the beads into the gastrointestinal tract and provides the desired controlled release of (1) a xanthine oxidoreductase inhibitor, such as, 2-[3-cyano-4-2(2-methylpropoxy)phenyl]-4-methylthiazole-5-carboxylic acid or (2) a xanthine oxidase inhibitor, such as allopurinol and oxypurinol.

These dosage forms are well known in the art. U.S. Pat. Nos. 5,286,497 and 5,737,320, both of which are hereby incorporated by reference, describe such formulations and their methods of production. One skilled in the art, taking into account the teachings in this application as well as those of the '320 and '497 patents, could produce a bead or pellet based dosage form matching the pharmacokinetic profile described above.

As a general guideline, however, a bead is formed with an inert core sphere and a xanthine oxidoreductase inhibitor or xanthine oxidase inhibitor, optionally in association with conventional excipients. The core of said beads may optionally comprise any materials commonly used in pharmaceutics and should be selected on the basis of compatibility with the active drug and the physicochemical properties of the beads. Additional components may include, but are not limited to binders, disintegration agents, filling agents, surfactants, solubilizers, stabilizers, and the like. Additionally, this core is then coated with one, or more, pharmaceutically acceptable polymers capable of imparting varied release characteristics. The central core may be prepared by a number of techniques known in the art. Typically, the xanthine oxidoreductase inhibitor or xanthine oxidase inhibitor is bound to an inert core with a conventional binding agent. The inert core typically comprises a starch, sugar or microcrystalline cellulose. One of skill in the art will appreciate that a variety of sugars may be incorporated into the bead core, and that compatibility issues should be considered when selecting the appropriate sugar. Before the xanthine oxidoreductase inhibitor or xanthine oxidase inhibitor is bound to the inert core, it is typically blended with conventional excipients to expedite its handling and to improve the properties of the final dosage form. These excipients are identical to those described above for the matrix systems. The quantity of these excipients can vary widely, but will generally be used in conventional amounts. The inert core is then produced by utilizing a binding agent to attach the powdered xanthine oxidoreductase inhibitor or xanthine oxidase inhibitor blend to the solid carrier. This can be accomplished by means known in the art for producing pharmaceutical beads. Suitable means include utilization of a conventional coating pan, a fluid-bed processor, extrusion-spheronization, or a rotogranulator. The production of these central cores is described in more detail in *Pharmaceutical Pelletization Technology*, ed. I. Ghebre-Sellassie, Marcel Dekker, Inc. New York, N.Y. (1989) which is hereby incorporated by reference.

The second major component of the beads is the polymeric coating. As noted above, the polymeric coating is responsible for giving the beads their extended release characteristics. The polymeric coating may be applied to the central core using methods and techniques known in the art. Examples of suitable coating devices include, but are not limited to, fluid bed coaters, pan coaters, etc. The application techniques are described in more detail in: 1) *Aqueous polymeric coatings for pharmaceutical dosage forms*, ed. J. W. McGinity, Marcel Dekker, Inc. New York, N.Y. (1997); and 2) *Pharmaceutical Dosage Forms: Tablets Vol.* 3. ed. H. A. Lieberman, L. Lachman and J. B. Schwartz, Marcel Dekker, Inc. New York, N.Y. pp. 77-287, (1990), the contents of which are hereby incorporated by reference.

The polymer may be incorporated into the beads by means of a layer attached to the pharmaceutical active, distal to the core and also may be provided in multiple layers, with each layer incorporating distinct polymers, providing for varied release characteristics in each layer. One such polymeric layer includes a modified release polymeric layer. The pharmaceutical active may be released from the modified release polymeric layer, such that the active particles are released as the polymer becomes soluble with the surrounding environment. Suitable examples of the immediate release polymers that may be used for the immediate release polymeric layer include, but are not limited to ethylcellulose, hydroxypropyl methylcellulose, hydroxylpropyl cellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride), polyurethane, ethylcellulose aqueous dispersions (AQUACOAT®, SURELEASE®), poly(butyl methacrylate, (2-dimethylaminoethyl) methacrylate, methyl methacrylate), poly(methacrylic acid, methyl methacrylate), poly(methacrylic acid, ethylacrylate), poly (methyl acrylate, methyl methacrylate, methacrylic acid), poly(ethylacrylate, methylmethacrylate, trimethylammonioethyl methacrylate chloride), poly(ethylacrylate, methyl methacrylate), poly(methacrylic acid, ethylacrylate), type A methacrylic acid copolymer, type B methacrylic acid copolymer, type C methacrylic acid copolymer, methacrylic acid copolymer dispersion, aqueous acrylic polymer dispersion, (EUDRAGIT® compounds), OPADRY® and the like, and mixtures thereof. In one aspect, the immediate release polymer comprises hydroxypropyl methylcellulose.

The polymeric layer that encapsulates the core becomes soluble and begins releasing the active drug immediately after ingestion by the patient. Under certain circumstances it may be beneficial to coat the core with a polymer, sealing the core material and providing easier coating of the core.

The beads of the current disclosure may also comprise an enteric coating layer that is applied onto the cores with or without seal coating by conventional coating techniques, such as pan coating or fluid bed coating using solutions of polymers in water or suitable organic solvents or by using aqueous polymer dispersions. All commercially available pH-sensitive polymers are included in the scope of the disclosure. With enteric coating layers, the pharmaceutical active is not released in the acidic stomach environment of approximately below pH 4.5, but not limited to this value. The pharmaceutical active is typically released when the pH-sensitive layer dissolves at the greater pH. Suitable examples of delayed release enteric polymers include, but are not limited to cellulose acetate phthalate, cellulose acetate trimellitate, hydroxypropyl methylcellulose phthalate, polyvinyl acetate phthalate, carboxymethylethylcellulose, co-polymerized methacrylic acid/methacrylic acid methyl esters such as, for instance, materials known under the trade name EUDRAGIT® L12.5, L100, EUDRAGIT® 512.5, 5100, or similar compounds used to obtain enteric coatings. Co-polymerized methacrylic acid/methacrylic acid methyl esters generally comprise three subclasses of compound: methacrylic acid copolymer type A, methacrylic acid copolymer type B, and methacrylic acid copolymer type C. The various types of copolymers represent compounds with varying ratios of methacrylic acid to methacrylic acid methyl ester. Accordingly, methacrylic acid copolymer type A has a ratio of methacrylic acid to methacrylic acid methyl ester of approximately 1:1, type B has a ratio of approximately 1:2, and type C has a ratio similar to type A, but may incorporate additional components, such as surfactants. Aqueous colloidal polymer dispersions or re-dispersions can be also applied, including, for example, the polymers sold under the trade name EUDRAGIT® L 30D-55, EUDRAGIT® L100-55, EUDRAGIT® S100, EUDRAGIT® preparation 4110D (Rohm Pharma); EUDRAGIT® FS 30 D; AQUATERIC®, AQUACOAT® CPD 30 (FMC); KOLLICOAT MAE® 30D and 30DP (BASF); and EASTACRYL® 30D (Eastman Chemical). In one aspect, the delayed release enteric polymer comprises methacrylic acid copolymer type A. In still yet another aspect, the delayed release enteric polymer comprises a mixture of methacrylic acid copolymer type A and methacrylic acid copolymer type B.

One skilled in the art will appreciate that additional components may be added to the delayed release polymers without departing from the scope of the disclosure. For instance, a plasticizer may be added to the delayed release enteric polymers to improve the physical characteristics of the delayed release polymeric layer. Non-limiting examples of plasticizers include triethyl citrate, acetyl triethyl citrate, tributyl citrate, acetyl tributyl citrate, trihexyl citrate, acetyl trihexyl citrate, trioctyl citrate, acetyl trioctyl citrate, butyryl trihexyl citrate, acetyl butyryl trihexyl citrate, trimethyl citrate, acetylated monoglycerides, and alkyl sulphonic acid phenyl esters. In yet another aspect, the plasticizer comprises triethyl citrate.

Furthermore, the enteric polymers used in this disclosure can be modified by mixing with other known coating products that are not pH sensitive. Examples of such coating products include the neutral methacrylic acid esters with a small portion of trimethylammonioethyl methacrylate chloride, sold currently under the trade names EUDRAGIT® and EUDRAGIT® RL; a neutral ester dispersion without any functional groups, sold under the trade names EUDRAGIT® NE30D and EUDRAGIT® NE30; and other pH independent coating products.

It is also within the scope of this disclosure that an additional modifying layer may be added on top of the enteric coating layer. This modifying layer can include a water penetration barrier layer (semipermeable polymer) which can be successively coated after the enteric coating to reduce the water penetration rate through the enteric coating layer and thus increase the lag time of the drug release. Controlled-release coatings commonly known to one skilled in the art can be used for this purpose by conventional coating techniques such as pan coating or fluid bed coating using solutions of polymers in water or suitable organic solvents or by using aqueous polymer dispersions. For example, the following non-limiting list of controlled release polymers may be used in the current disclosure: cellulose acetate, cellulose acetate butyrate, cellulose acetate propionate, ethylcellulose, hydroxypropyl methylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly (lauryl methacrylate), poly(phenyl methacrylate), poly(methyl acrylate), poly(isopropyl acrylate), poly(isobutyl acrylate), poly(octadecyl acrylate), poly(ethylene), poly (ethylene) low density, poly(ethylene) high density, poly (propylene), poly(ethylene oxide), poly(ethylene terephthalate), poly(vinyl isobutyl ether), poly(vinyl acetate), poly(vinyl chloride), polyurethane, ethylcellulose aqueous dispersions such as AQUACOAT® and SURELEASE®, poly(butyl methacrylate, (2-dimethylaminoethyl) methacrylate, methyl methacrylate), poly(methacrylic acid, methyl methacrylate), poly(methacrylic acid, ethylacrylate), poly(methyl acrylate, methyl methacrylate, methacrylic acid), poly(ethylacrylate, methylmethacrylate, trimethylammonioethyl methacrylate chloride), poly(ethylacrylate, methyl methacrylate), poly(methacrylic acid, ethylacrylate), type A methacrylic acid copolymer, type B methacrylic acid copolymer, type C methacrylic acid copolymer, methacrylic acid copolymer dispersion, aqueous acrylic polymer dispersion, (EUDRAGIT® compounds), OPADRY®, fatty acids and their esters, waxes, zein, and aqueous polymer dispersions such as EUDRAGIT® RS and RL 30D, EUDRAGIT® NE 30D, cellulose acetate latex. The combination of above polymers and hydrophilic polymers such as hydroxyethyl cellulose, hydroxypropyl cellulose (KLUCEL®, Hercules Corp.), hydroxypropyl methylcellulose (METHOCEL®, Dow Chemical Corp.), and polyvinylpyrrolidone may also be incorporated. In one aspect, the controlled release polymer comprises ethylcellulose, hydroxypropyl methylcellulose, and combinations thereof. In yet another aspect, the controlled release polymer comprises a combination of ethylcellulose and hydroxypropyl methylcellulose in a ratio of ethylcellulose to hydroxypropyl methylcellulose ranging from about 0.1 to about 10, from about 0.2 to about 5, from about 0.5 to about 3, and from about 1 to about 2. In still yet another aspect, the controlled release polymer comprises a combination of ethylcellulose aqueous dispersion and hydroxypropyl methylcellulose in a ratio of ethylcellulose aqueous dispersion to hydroxypropyl methylcellulose ranging from about 0.1 to about 10, from about 0.1 to about 5, from about 0.5 to about 4, and from about 1.5 to about 3.

The pharmaceutical composition of the current disclosure, in one aspect, comprises one or more types of bead, can be incorporated in multiple dosage forms such as capsules, pills, and tablets. Capsules, including hard gelatin capsules, may be produced according to methods known in the art. Generally, the capsules may incorporate the beads discussed herein, and may optionally incorporate additional excipients, as previously described. The pharmaceutical composition may also be incorporated into a tablet. Generally, this process involves incorporation of the beads into a tablet matrix, as previously described. One skilled in the art will appreciate that additional components may be added to the formulation to impart the desired physical characteristics, without departing from the scope of the disclosure.

Types of Beads

There are many types of bead formulations that are encompassed within the scope of the current disclosure, incorporating various polymers in accordance with the polymers previously described. One skilled in the art may modify bead formulations to impart specific chemical characteristics. In one aspect, the current disclosure describes four primary types of beads. Namely, the four types of beads may be described as immediate release beads, delayed release beads, controlled release beads, and delayed-controlled release beads. The immediate release beads comprise a xanthine oxidoreductase inhibitor or xanthine oxidase inhibitor layered on an inert core such as sugar spheres or microcrystalline cellulose spheres by means of a suitable polymeric binder. The polymeric binder functions to create a sealcoat around the inert core material, improving the friability of the inert core. The polymeric binder may comprise any of the immediate release polymers previously described. In one aspect, the polymeric binder comprises hydroxypropyl methylcellulose. For the purposes of the various bead compositions described herein, the polymeric binder component will comprise the same material as the immediate release polymer, and the percentage composition of immediate release polymer will include the immediate release polymer used in the immediate release layer surrounding the inert core, as well as the polymeric binder providing the sealcoat for the inert core.

The immediate release bead typically comprises from about 5% to about 55% (w/w) xanthine oxidoreductase inhibitor or xanthine oxidase inhibitor, from about 20% to about 80% (w/w) inert core, and from about 1% to about 40% (w/w) immediate release polymer. In one aspect, the immediate release bead typically comprises from about 25% to about 35% (w/w) xanthine oxidoreductase inhibitor or xanthine oxidase inhibitor, from about 40% to about 60% (w/w) inert core, and from about 10% to about 20% (w/w) immediate release polymer. In another aspect the xanthine oxidoreductase inhibitor or xanthine oxidase inhibitor comprises from about 29% to about 34% (w/w) of the total composition, the inert core comprises from about 50% to about 55% (w/w) of the total composition, and the immediate release polymer comprises from about 14% to about 18% (w/w) of the total composition.

An additional type of bead that is contemplated by the current disclosure is a delayed release bead. Delayed release beads are coated beads obtained by coating immediate release beads with a delayed release enteric polymer either in an aqueous dispersion or in an organic solvent. These polymers have pH dependent solubility depending on the functional groups on the polymer. For a delayed release bead coated with suitable amount of delayed release enteric polymer, drug release will not occur in a medium unless medium pH is above the pH at which the polymer dissolves. The delayed release enteric polymers of the current disclosure generally become soluble when the bead is exposed to a pH level generally less acidic than the environment of the stomach. Specifically, the delayed release polymer may become soluble at pH levels greater than or equal to 4.5; 4.6; 4.7; 4.8; 4.9; 5.0; 5.1; 5.2; 5.3; 5.4; 5.5; 5.6; 5.7; 5.8; 5.9; 6.0; 6.1; 6.2; 6.3; 6.4; 6.5; 6.6; 6.7; 6.8; 6.9; 7.0; 7.1; 7.2; 7.3; 7.4; 7.5; 7.6; 7.7; 7.8; 7.9; 8.0; 8.1; 8.2; 8.3; 8.4; 8.5; 8.6; 8.7; 8.8; 8.9; 9.0; 9.1; 9.2; 9.3; 9.4; 9.5; 9.6; 9.7; 9.8; 9.9; and 10.0. In one aspect, the delayed release polymer becomes soluble at pH levels greater than or equal to 5.5, 6.0, and 6.8.

The composition of the immediate release component of the delayed release bead is the same as previously described, and generally comprises a xanthine oxidoreductase inhibitor or xanthine oxidase inhibitor, an inert core, and an immediate release polymer, as previously described. The delayed release bead additionally comprises a pH-sensitive enteric polymer, as previously described. A non-limiting example of a delayed release bead is one in which the bead has a solubility at pH levels greater than or equal to 6.0. This delayed release pH 6.0 bead typically comprises a xanthine oxidoreductase inhibitor or xanthine oxidase inhibitor from about 5% to about 50% (w/w) of the overall delayed release bead, an inert core comprising from about 20% to about 70% (w/w) of the total delayed release bead, an immediate release polymer comprising from about 1% to about 35% (w/w) of the total delayed release bead, and a delayed release enteric polymer in an amount ranging from about 1% to about 35% (w/w) of the total delayed release bead. In one aspect, the delayed release bead comprises from about 20% to about 30% (w/w) xanthine oxidoreductase inhibitor or xanthine oxidase inhibitor, from about 40% to about 50% (w/w) of an inert core, from about 10% to about 16% (w/w) immediate release polymer, and from about 13% to about 20% (w/w) delayed release polymer. In a further iteration of this example, the delayed release pH 6.0 bead further comprises approximately 1% to approximately 3% (w/w) plasticizer.

Another non-limiting example of a delayed release bead is one in which the bead has a solubility at pH levels greater than or equal to 6.8. This delayed release pH 6.8 bead typically comprises a xanthine oxidoreductase inhibitor or xanthine oxidase inhibitor from about 5% to about 50% (w/w) of the overall delayed release bead, an inert core comprising from about 20% to about 70% (w/w) of the total delayed release bead, an immediate release polymer comprising from about 1% to about 35% (w/w) of the total delayed release bead, and a delayed release enteric polymer in an amount ranging from about 1% to about 35% (w/w) of the total delayed release bead. In one aspect, the delayed release pH 6.8 bead comprises from about 20% to about 30% (w/w) xanthine oxidoreductase inhibitor or xanthine oxidase inhibitor, from about 40% to about 50% (w/w) of an inert core, from about 10% to about 16% (w/w) immediate release polymer, and from about 13% to about 20% (w/w) delayed release polymer. In one aspect, the delayed release pH 6.8 bead comprises from about 23% to about 27% (w/w) xanthine oxidoreductase inhibitor or xanthine oxidase inhibitor, from about 40.5% to about 43% (w/w) of an inert core, from about 12% to about 14% (w/w) immediate release polymer, and from about 17% to about 19% (w/w) of one or more delayed release enteric polymers. In a further iteration of this example, the delayed release pH 6.8 bead further comprises approximately 1% to approximately 3% (w/w) plasticizer.

An additional type of bead that is contemplated by the current disclosure is a controlled release bead. Controlled release beads are coated beads obtained by coating immediate release beads with a controlled release polymer according to methods currently known in the art. Generally, the controlled release beads incorporate one or more polymers that decrease the release rate of the drug from the bead, so that the drug is released over an extended period of time. Controlled release beads differ from delayed release beads in that the release from controlled release beads is continuous after exposure to dissolution medium, over an extended period of time, whereas release from delayed release beads is very rapid once the beads are exposed to a pH above which the delayed release enteric polymer is soluble. In general, the composition of the controlled release polymeric layer may be modified such that release is possible over periods of time ranging from approximately 1 hour to approximately 24 hours. Specifically, the controlled release formulation may release active drug over a period of 1, 2, 3, 4, 5, 6, 7, 8, 9, 10, 11, 12, 13, 14, 15, 16, 17, 18, 19, 20, 21, 22, 23, and 24 hours.

In one embodiment of the current disclosure, the controlled release beads incorporate a composition capable of releasing the active compound over a period of time ranging from approximately four hours to approximately six hours. The controlled release beads of this embodiment generally comprise from about 5% to about 40% (w/w) xanthine oxidoreductase inhibitor or xanthine oxidase inhibitor, from about 20% to about 50% (w/w) of an inert core, from about 5% to about 25% (w/w) immediate release polymer, from about 10% to about 50% (w/w) controlled release polymer. In one aspect, the controlled release beads comprise from about 20% to about 24% (w/w) xanthine oxidoreductase inhibitor or xanthine oxidase inhibitor, from about 30% to about 40% (w/w) of an inert core, from about 9% to about 13% (w/w) immediate release polymer, from about 25% to about 35% (w/w) controlled release polymer. In one aspect, the controlled release beads comprise from about 25% to about 35% (w/w) xanthine oxidoreductase inhibitor or xanthine oxidase inhibitor, from about 40% to about 60% (w/w) of an inert core, from about 12% to about 18% (w/w) immediate release polymer, from about 3% to about 9% (w/w) controlled release polymer.

In an additional embodiment, the controlled release beads incorporate a composition capable of releasing the active compound over a period of time ranging from approximately ten hours to approximately twelve hours. The controlled release beads of this embodiment generally comprise from about 10% to about 50% (w/w) xanthine oxidoreductase inhibitor or xanthine oxidase inhibitor, from about 30% to about 70% (w/w) of an inert core, from about 5% to about 25% (w/w) immediate release polymer, and from about 1% to about 15% (w/w) controlled release polymer. In one aspect, the controlled release beads comprise from about 25% to about 35% (w/w) xanthine oxidoreductase inhibitor or xanthine oxidase inhibitor, from about 40% to about 60% (w/w) of an inert core, from about 12% to about 18% (w/w) immediate release polymer, and from about 3% to about 9% (w/w) controlled release polymer. In one aspect, the controlled release beads comprise from about 28% to about 31% (w/w) xanthine oxidoreductase inhibitor or xanthine oxidase inhibitor, from about 47% to about 51% (w/w) of an inert core, from about 14% to about 16% (w/w) immediate release polymer, and from about 5% to about 7% (w/w) controlled release polymer.

A further type of bead that is contemplated by the current disclosure is a delayed-controlled release bead. The delayed-controlled release bead combines the attributes of the delayed release beads described above and the controlled release beads described above, with the goal of delaying drug release until the beads are exposed to a pH greater than the pH at which the polymer dissolves, and subsequently prolonging drug release over an extended period of time. To illustrate, a controlled release bead, administered alone, would typically release the active component over an extended period of time, with release beginning immediately after ingestion. Delayed release beads, administered alone, would not begin releasing the active component until the environment meets a minimum pH level. For instance, the pH level in the intestine is higher than that of the stomach, therefore, a delayed release bead may be designed to release the active component once it reaches the pH level found in the intestine, without releasing any active component in regions where the pH level is lower, such as the stomach. However, once the pH level is triggered, drug release is typically rapid.

In the instant embodiment, the delayed release polymeric layer encapsulates the controlled release polymeric layer, such that the prolonged release of active component allowed by the controlled release polymer will not begin until the delayed-controlled release bead is exposed to a minimum pH level. Accordingly, one skilled in the art will appreciate that the characteristics of the delayed-controlled release bead may be modified such that the delayed release polymer does not become soluble until the bead is exposed to pH levels generally ranging from about 5 to about 10, as previously described. Furthermore, the delayed-controlled release beads may be designed to release the active component for a period ranging from about one hour to about twenty-four hours, as previously described.

In one embodiment, of the current disclosure, the delayed-controlled release bead incorporates a delayed release enteric polymer with a solubility at pH levels greater than or equal to 6.8, and a controlled release polymer allowing for prolonged delivery of the active compound over four to six hours. The delayed-controlled release beads of this embodiment generally comprise from about 5% to about 35% (w/w) xanthine oxidoreductase inhibitor or xanthine oxidase inhibitor, from about 20% to about 50% (w/w) of an inert core, from about 5% to about 20% (w/w) immediate release polymer, from about 5% to about 20% (w/w) controlled release polymer, and from about 5% to about 35% (w/w) delayed release enteric polymer. In one aspect, the delayed-controlled release beads comprise from about 15% to about 25% (w/w) xanthine oxidoreductase inhibitor or xanthine oxidase inhibitor, from about 30% to about 40% (w/w) of an inert core, from about 8% to about 14% (w/w) immediate release polymer, from about 8% to about 15% (w/w) controlled release polymer, and from about 13% to about 22% (w/w) delayed release enteric polymer. In another aspect, the delayed-controlled release bead comprises from about 20% to about 23% (w/w) xanthine oxidoreductase inhibitor or xanthine oxidase inhibitor, from about 34% to about 37% (w/w) of an inert core, from about 10% to about 12% (w/w) immediate release polymer, from about 11% to about 13% (w/w) controlled release polymer, and from about 17% to about 20% (w/w) delayed release enteric polymer.

One skilled in the art will appreciate that the various modified release beads of the current disclosure may be manufactured by any means known in the art. Examples of non-limiting methods of manufacturing the beads include fluid bed processing, centrifugal granulation, extrusion-spheronization, high shear granulation, melt extrusion, and solution or suspension layering. In a fluid bed process, the immediate release polymer is dissolved in water and micronized drug is suspended in the immediate release polymer solution. This suspension is then sprayed onto inert spherical support beads such as sugar spheres or microcrystalline cellulose spheres. Alternately, non-micronized drug can be suspended in the immediate release polymer solution and the suspension can be passed through a mill. In the centrifugal granulation process, the inert beads are placed in the granulator on a rotating disc at the bottom of the granulator. Micronized drug is introduced into the granulator and a solution of the immediate release polymer is sprayed at the same time. Extrusion and spheronization is another manufacturing method for immediate release beads, wherein the drug is mixed with dry excipients and wet-massed by addition of a binder solution and extruded to form spaghetti-like strands. The extrudate is then chopped and converted to dense spherical beads using a spheronizer. Another method of producing beads includes high shear granulation. High shear granulation involves dry mixing the active component and other components. Then the mixture is wetted by addition of a binder solution in a high shear-granulator/ mixer. The granules are kneaded after wetting by the combined action of mixing and milling. The resulting granules or pellets are subsequently dried and sieved. An additional method comprises melt-extrusion or melt-granulation. This process generally involves melting a normally solid hydrophobic binder material, e.g. a wax or similar substance, and incorporating a powdered drug therein. To obtain a controlled or extended release dosage form, additional hydrophobic release materials, e.g. ethylcellulose or a water-insoluble acrylic polymer, may be incorporated into the molten wax hydrophobic binder material. Further, solution or suspension layering involves a process whereby an active component solution or dispersion with or without a binder is sprayed onto starting seeds with a certain particle size in a fluidized bed processor or other suitable equipment. The drug thus is coated on the surface of the starting seeds. The drug-loaded pellets are dried for further applications.

Pharmaceutical Dosage Forms

It will be understood by one skilled in the art that the various types of beads described herein, with distinct active release profiles may be combined in single or multiple pharmaceutical dosage forms to provide pulsed drug delivery of the xanthine oxidoreductase inhibitor or xanthine oxidase inhibitors described herein. Various combinations of immediate release beads, delayed release beads, controlled release beads, and delayed-controlled release beads may be used to impart distinct release profiles. It should be understood that any potential combination of immediate release, delayed release, controlled release, and delayed-controlled release beads for the distribution of the xanthine oxidoreductase inhibitor or xanthine oxidase inhibitors described herein are within the scope of the current disclosure.

In one embodiment, the current disclosure encompasses a single pharmaceutical composition that incorporates both immediate release beads and delayed release beads with a solubility at pH levels greater than or equal to 6.8. The pharmaceutical composition of this embodiment comprises immediate release xanthine oxidoreductase inhibitor or xanthine oxidase inhibitor beads in an amount ranging from approximately 20% to approximately 40% (w/w) of the total composition weight and pH 6.8 delayed release xanthine oxidoreductase inhibitor or xanthine oxidase inhibitor beads in an amount ranging from approximately 60% to approximately 80% (w/w) of the total composition weight.

The immediate release beads comprise: a.) an inert core in an amount ranging from about 50% to about 55% (w/w) of the weight of the immediate release bead; and b.) an immediate release layer that encapsulates the inert core comprising a mixture of xanthine oxidoreductase inhibitor or xanthine oxidase inhibitor and a binder such as hydroxypropyl methylcellulose or hydroxypropyl cellulose in an amount ranging from about 45% to about 50% (w/w) of the weight of the immediate release bead, the ratio of xanthine oxidoreductase inhibitor or xanthine oxidase inhibitor to hydroxypropyl methylcellulose ranging from about 1.5 to about 3. An insoluble disintegrant such as low substituted hydroxylpropyl cellulose (L-HPC) may be added to speed release of the active.

The pH 6.8 delayed release beads comprise a.) an inert core in an amount ranging from about 40.5% to about 43% (w/w) of the weight of the delayed release bead; b.) an immediate release layer encapsulating the inert core (as described before) in an amount ranging from about 35% to about 40% (w/w) of the weight of the delayed release bead, the ratio of xanthine oxidoreductase inhibitor or xanthine oxidase inhibitor to hydroxypropyl methylcellulose ranging from about 1.5 to about 3; c.) a delayed release enteric polymer layer encapsulating the immediate release layer comprising a delayed release enteric polymer in an amount ranging from about 17% to about 20% (w/w) of the delayed release bead, said delayed release enteric polymer comprising a mixture of methacrylic acid copolymer type A and methacrylic acid copolymer type B in a ratio ranging from approximately 0.1 to approximately 0.5; and d.) a plasticizer in an amount ranging from about 1% to about 3% (w/w) of the weight of the delayed-controlled release bead. In one aspect of the pharmaceutical composition, the xanthine oxidoreductase inhibitor comprises febuxostat and the plasticizer comprises triethyl citrate. In another aspect, the xanthine oxidase inhibitor in the pharmaceutical composition comprises allopurinol and the plasticizer comprises triethyl citrate.

In yet another embodiment of the current disclosure, the pharmaceutical dosage form encompasses a single pharmaceutical composition that incorporates immediate release beads, delayed release beads with solubility at pH levels greater than or equal to 6.0, and delayed release beads with solubility at pH levels greater than or equal to 6.8. The pharmaceutical composition of this embodiment comprises immediate release xanthine oxidoreductase inhibitor or xanthine oxidase inhibitor beads in an amount ranging from approximately 25% to approximately 35% (w/w) of the total composition weight, pH 6.0 delayed release xanthine oxidoreductase inhibitor or xanthine oxidase inhibitor beads in an amount ranging from approximately 25% to approximately 35% (w/w) of the total composition weight, and pH 6.8 delayed release xanthine oxidoreductase inhibitor or xanthine oxidase inhibitor beads in an amount ranging from approximately 35% to approximately 45% (w/w) of the total composition weight.

The immediate release beads comprise: a.) an inert core in an amount ranging from about 50% to about 55% (w/w) of the weight of the immediate release bead; and b.) an immediate release layer that encapsulates the inert core comprising a mixture of xanthine oxidoreductase inhibitor or xanthine oxidase inhibitor and hydroxypropyl methylcellulose in an amount ranging from about 45% to about 50% (w/w) of the weight of the immediate release bead, the ratio of xanthine oxidoreductase inhibitor or xanthine oxidase inhibitor to hydroxypropyl methylcellulose ranging from about 1.5 to about 3.

The delayed release pH 6.0 beads comprise: a.) an inert core in an amount ranging from about 40.5% to about 43% (w/w) of the weight of the delayed release pH 6.0 bead; b.) an immediate release layer encapsulating the inert core comprising a mixture of xanthine oxidoreductase inhibitor or xanthine oxidase inhibitor and hydroxypropyl methylcellulose in an amount ranging from about 35% to about 40% (w/w) of the weight of the delayed release pH 6.0 bead, the ratio of xanthine oxidoreductase inhibitor or xanthine oxidase inhibitor to hydroxypropyl methylcellulose ranging from about 1.5 to about 3; c.) a delayed release pH 6.0 enteric polymer layer encapsulating the immediate release layer comprising a delayed release enteric polymer in an amount ranging from about 17% to about 19% (w/w) of the delayed release bead, said delayed release pH 6.0 enteric polymer comprising methacrylic acid copolymer type A; and d.) a plasticizer in an amount ranging from about 1% to about 3% (w/w) of the weight of the delayed-controlled release bead.

Two types of beads, namely immediate release and pH 6.0 delayed release beads can be combined together into a single bead for convenience by applying an immediate release coat on the top of a pH 6.0 delayed release coat. The resulting composition contains a.) an inert core in an amount ranging from about 25% to about 35% (w/w) of the weight of the combined immediate release-delayed release pH 6.0 bead; b.) an immediate release layer encapsulating the inert core comprising a mixture of xanthine oxidoreductase inhibitor or xanthine oxidase inhibitor and hydroxypropyl methylcellulose in an amount ranging from about 25% to about 31% (w/w) of the weight of the combined bead; c.) a delayed release pH 6.0 enteric polymer layer encapsulating the immediate release layer comprising a delayed release enteric polymer in an amount ranging from about 11% to about 15% (w/w) of the delayed release bead, said delayed release pH 6.0 enteric polymer comprising methacrylic acid copolymer type A; d.) a plasticizer in an amount ranging from about 1% to about 3% (w/w) of the weight of the delayed-controlled release bead; and e.) an immediate release overcoat layer comprising a mixture of xanthine oxidoreductase inhibitor or xanthine oxidase inhibitor and hydroxypropyl methylcellulose in an amount ranging from about 23% to about 29% (w/w) of the weight of the combined bead.

The delayed release pH 6.8 beads comprise: a.) an inert core in an amount ranging from about 40.5% to about 43% (w/w) of the weight of the delayed release bead; b.) an immediate release layer encapsulating the inert core comprising a mixture of xanthine oxidoreductase inhibitor or xanthine oxidase inhibitor and hydroxypropyl methylcellulose in an amount ranging from about 35% to about 40% (w/w) of the weight of the delayed release bead, the ratio of xanthine oxidoreductase inhibitor or xanthine oxidase inhibitor to hydroxypropyl methylcellulose ranging from about 1.5 to about 3; c.) a delayed release pH 6.8 enteric polymer layer encapsulating the immediate release layer comprising a delayed release enteric polymer in an amount ranging from about 17% to about 20% (w/w) of the delayed release pH 6.8 bead, said delayed release enteric polymer comprising a mixture of methacrylic acid copolymer type A and methacrylic acid copolymer type B in a ratio ranging from approximately 0.1 to approximately 0.5; and d.) a plasticizer in an amount ranging from about 1% to about 3% (w/w) of the weight of the delayed-controlled release bead, said plasticizer comprising triethyl citrate. In another aspect of the pharmaceutical composition, the xanthine oxidoreductase inhibitor comprises febuxostat, and the plasticizer comprises triethyl citrate. In still yet another aspect of this pharmaceutical composition, the xanthine oxidase inhibitor comprises allopurinol, and the plasticizer comprises triethyl citrate.

In a further embodiment of the current disclosure, the pharmaceutical composition encompasses a single pharmaceutical composition that incorporates immediate release beads and delayed-controlled release beads, with the delayed release polymer having solubility at a pH level of at least 6.8 and a controlled release rate of approximately four to six hours. The pharmaceutical composition of this embodiment comprises immediate release xanthine oxidoreductase inhibitor or xanthine oxidase inhibitor beads in an amount ranging from approximately 20% to approximately 40% (w/w) of the total composition weight and delayed-controlled release xanthine oxidoreductase inhibitor or xanthine oxidase inhibitor beads having a solubility at pH levels greater than or equal to 6.8 and providing prolonged release of xanthine oxidoreductase inhibitor or xanthine oxidase inhibitor over a period of about 4 hours to about 6 hours, in an amount ranging from approximately 60% to approximately 80% (w/w) of the total composition weight. For example, in one aspect, the pharmaceutical composition comprises immediate release xanthine oxidoreductase inhibitor or xanthine oxidase inhibitor beads in an amount of approximately 20% (w/w) of the total composition weight delayed release xanthine oxidoreductase inhibitor or xanthine oxidase inhibitor beads that release at a pH of 6.8 in an amount of approximately 80% (w/w) of the total composition weight. In yet another aspect, the pharmaceutical composition comprises immediate release xanthine oxidoreductase inhibitor or xanthine oxidase inhibitor beads in an amount of approximately 25% (w/w) of the total composition weight delayed release xanthine oxidoreductase inhibitor or xanthine oxidase inhibitor beads that release at a pH of 6.8 in an amount of approximately 75% (w/w) of the total composition weight. In still yet another aspect, the pharmaceutical composition comprises immediate release xanthine oxidoreductase inhibitor or xanthine oxidase inhibitor beads in an amount of approximately 30% (w/w) of the total composition weight delayed release xanthine oxidoreductase inhibitor or xanthine oxidase inhibitor beads that release at a pH of 6.8 in an amount of approximately 70% (w/w) of the total composition weight. In still yet another aspect, the pharmaceutical composition comprises immediate release xanthine oxidoreductase inhibitor or xanthine oxidase inhibitor beads in an amount of approximately 40% (w/w) of the total composition weight delayed release xanthine oxidoreductase inhibitor or xanthine oxidase inhibitor beads that release at a pH of 6.8 in an amount of approximately 60% (w/w) of the total composition weight.

The immediate release beads comprise: a.) an inert core in an amount ranging from about 50% to about 55% (w/w) of the weight of the immediate release bead; and b.) an immediate release layer that encapsulates the inert core comprising a mixture of xanthine oxidoreductase inhibitor or xanthine oxidase inhibitor and hydroxypropyl methylcellulose in an amount ranging from about 45% to about 50% (w/w) of the weight of the immediate release bead, the ratio of xanthine oxidoreductase inhibitor or xanthine oxidase inhibitor to hydroxypropyl methylcellulose ranging from about 1.5 to about 3.

The delayed-controlled release beads comprise: a.) a inert core in an amount ranging from about 34% to about 37% (w/w) of the weight of the delayed-controlled release bead; b.) an immediate release layer that encapsulates the inert core comprising a mixture of xanthine oxidoreductase inhibitor or xanthine oxidase inhibitor and hydroxypropyl methylcellulose in an amount ranging from about 31% to about 34% (w/w) of the weight of the delayed-controlled release bead, the ratio of xanthine oxidoreductase inhibitor or xanthine oxidase inhibitor to hydroxypropyl methylcellulose ranging from about 1.5 to about 2.5; c.) a controlled release layer that encapsulates the immediate release layer comprising a controlled release polymer in an amount ranging from about 10% to about 14% (w/w) of the weight of the delayed-controlled release bead, said controlled release polymer comprising a mixture of ethylcellulose aqueous dispersion and hydroxypropyl methylcellulose, the ratio of ethylcellulose dispersion to hydroxypropyl methylcellulose ranging from about 1.5 to about 3; d.) a delayed release pH 6.8 layer that encapsulates the controlled release layer comprising a delayed release pH 6.8 polymer in an amount ranging from about 17.5% to about 20% (w/w) of the weight of the delayed-controlled release bead, said delayed release pH 6.8 polymer comprising a mixture of methacrylic acid copolymer type A and methacrylic acid copolymer type B, the ratio of copolymer type A to copolymer type B ranging from about 0.1 to about 0.5; and e.) a plasticizer in an amount ranging from about 1% to about 3% (w/w) of the weight of the delayed-controlled release bead, said plasticizer comprising triethyl citrate. In one aspect of the pharmaceutical composition, the xanthine oxidoreductase inhibitor comprises febuxostat, and the plasticizer comprises triethyl citrate. In yet another aspect of this pharmaceutical composition, the xanthine oxidase inhibitor comprises allopurinol, and the plasticizer comprises triethyl citrate.

In still another embodiment of the current disclosure, the pharmaceutical composition encompasses a single pharmaceutical composition that incorporates immediate release beads and controlled release beads capable of active release over approximately ten to approximately twelve hours. The pharmaceutical composition of this embodiment generally comprises immediate release xanthine oxidoreductase inhibitor or xanthine oxidase inhibitor beads in an amount ranging from approximately 10% to approximately 30% (w/w) of the total composition weight and controlled release xanthine oxidoreductase inhibitor or xanthine oxidase inhibitor beads providing prolonged release of xanthine oxidoreductase inhibitor or xanthine oxidase inhibitor over a period of about 10 hours to about 12 hours, in an amount ranging from approximately 70% to approximately 90% (w/w) of the total composition weight.

The immediate release beads comprise: a.) an inert core in an amount ranging from about 50% to about 55% (w/w) of the weight of the immediate release bead; and b.) an immediate release layer that encapsulates the inert core comprising a mixture of xanthine oxidoreductase inhibitor or xanthine oxidase inhibitor and hydroxypropyl methylcellulose in an amount ranging from about 45% to about 50% (w/w) of the weight of the immediate release bead, the ratio of xanthine oxidoreductase inhibitor or xanthine oxidase inhibitor to hydroxypropyl methylcellulose ranging from about 1.5 to about 3.

The ten to twelve hour controlled release beads comprise: a.) an inert core in an amount ranging from about 47% to about 51% (w/w) of the weight of the controlled release bead; b.) an immediate release layer that encapsulates the inert core comprising a mixture of xanthine oxidoreductase inhibitor or xanthine oxidase inhibitor and hydroxypropyl methylcellulose in an amount ranging from about 42% to about 48% (w/w) of the weight of the controlled release bead, the ratio of xanthine oxidoreductase inhibitor or xanthine oxidase inhibitor to hydroxypropyl methylcellulose ranging from about 1.5 to about 2.5; and c.) a controlled release layer that encapsulates the immediate release layer comprising a controlled release polymer, said controlled release polymer comprising a mixture of ethylcellulose and hydroxypropyl methylcellulose in an amount ranging from about 4% to about 8% (w/w) of the weight of the controlled release bead, the ratio of ethylcellulose to hydroxypropyl methylcellulose ranging from about 1 to about 2. In yet another aspect of the pharmaceutical composition, the xanthine oxidoreductase inhibitor comprises febuxostat. In still yet another aspect of this pharmaceutical composition, the xanthine oxidase inhibitor comprises allopurinol.

One of skill in the art will appreciate that the various embodiments and dosage forms described herein may incorporate any dosage form known in the art. In one aspect, the dosage forms including pills, tablets, and capsules. Furthermore, the pharmaceutical compositions may have total composition weights ranging from approximately 5 mg to approximately 240 mg. In one aspect, the overall pharmaceutical composition weight (total weight) comprises approximately 60 mg to approximately 100 mg. In another aspect, the total pharmaceutical composition weight of approximately 80 mg.

Methods of Treatment

The dosage forms of the present disclosure can be used in treating a variety of disease conditions. When the dosage forms of the present disclosure contain febuxostat, such dosage forms can be used in treating conditions such as, but not limited to, gout, hyperuricemia, prostatitis, inflammatory bowel disease, QT interval prolongation, myocardial infarction, cardiac hypertrophy, hypertension, nephrolithiasis, renal impairment, chronic kidney disease, metabolic syndrome (also referred to as "Syndrome X" and includes, at least one of abdominal obesity, atherogenic dyslipidemia, insulin resistance, glucose intolerance, a prothrombotic state or a proinflammatory state), diabetes, diabetic nephropathy, congestive heart failure, etc. Subjects suffering from one of the above disease conditions and in need of treatment thereof can be administered an effective amount (or therapeutically effective amount) of the dosage form of the present disclosure to treat said disease condition.

When the dosage forms of the present disclosure contain allopurinol or oxypurinol, such dosage forms can be used in treating conditions such as, but not limited to, gout, hyperuricemia, prostatitis, inflammatory bowel disease, QT interval prolongation, myocardial infarction, cardiac hypertrophy, hypertension, nephrolithiasis, renal impairment, chronic kidney disease, metabolic syndrome (also referred to as "Syndrome X" and includes, at least one of abdominal obesity, atherogenic dyslipidemia, insulin resistance, glucose intolerance, a prothrombotic state or a proinflammatory state), diabetes, diabetic nephropathy, congestive heart failure, etc. Subjects suffering from one of the above disease conditions and in need of treatment thereof can be administered an effective amount (or therapeutically effective amount) of the dosage form of the present disclosure to treat said disease condition.

By way of example, and not of limitation, examples of the present disclosure will now be given.

Example 1: Methods for Obtaining A High Level of Xanthine Oxidase Inhibition

Comparative Example

In healthy human subjects, the majority of orally administered febuxostat is absorbed in approximately 1 hour (i.e., the $t_{max}$ is approximately one hour). Moreover, the oral clearance of febuxostat from the plasma is approximately 7.3-15.1 L/hr, with an effective half-life of approximately six (6) hours. In fact, the drug is highly bound to albumin in the blood (~99.3%) and appears to have a low to medium apparent volume of distribution of approximately 0.7 L/kg.

Despite the relatively short effective half-life of febuxostat, clinical studies have shown that once a day dosing with immediate release formulations containing as little as 10 mg of febuxostat lowers concentrations of uric acid with minimal fluctuations in the serum uric acid concentrations in healthy subjects. This is due to the nature of the pharmacokinetic (PK)-pharmacodynamic (PD) relationship between the plasma concentrations of febuxostat (the PK marker) and the serum uric acid concentrations (the PD marker). Once a day dosing with immediate release dosage forms containing as little as 10 mg febuxostat is expected to effectively decrease and maintain serum uric acid concentrations at a therapeutic target (i.e. <6 mg/dL) for a gout patient with low serum uric acid concentration (i.e. 7 mg/dL); however, these dosage forms fail to maintain a high degree of inhibition, namely at least 80% inhibition of the xanthine oxidase enzyme during the dosing interval (namely, 24 hours) even after multiple dosings.

Table 1 below shows the results from a Phase 1, multiple-dose, randomized, placebo-controlled, double-blind, single-center, multiple-location dose escalation study involving febuxostat. This study evaluated the pharmacokinetics and pharmacodynamics of febuxostat in healthy subjects. In this study, oral doses of an immediate release dosage form of febuxostat ranged from 10 mg once a day to 240 mg once a day (hereinafter "QD") and as 30 mg twice a day (hereinafter "BID"). Plasma, serum and urine samples were collected for the determination of febuxostat and metabolites, uric acid, xanthine and hypoxanthine concentrations. Samples were analyzed by high performance liquid chromatography.

Furthermore, the percent inhibition of xanthine oxidase at 12, 16, and 24 hours (post dose) following multiple dosings with immediate release dosage forms containing 70 mg and 120 mg of febuxostat in healthy subjects were calculated using Equation 1 below. The results of this calculation were incorporated into Equation 2, discussed below, and the results of Equation 2 are listed in Table 2 below:

Percent Inhibition ($"\%\ Inhibition"$)
of xanthine oxidase ($"XOD"$)

TABLE 1

Pharmacokinetics and Pharmacodynamics of Febuxostat Administration at Multiple Doses with Multiple Release Profiles

| Dose | $t_{max}$ (h) | $C_{max}$ (µg/mL) | AUC$^a$ (µg · h/mL) | $t_{1/2z}{}^b$ (h) | $V_{ss}/F$ (L) | Cl/F (L/h) | $C_{max}/D$ | AUC$^a$/D |
|---|---|---|---|---|---|---|---|---|
| 10 mg QD | | | | | | | | |
| Day 1 | 0.99 | 0.3362 | 0.7769 | 1.5 (1.3) | 38.2 | 15.12 | 0.0336 | 0.0727 |
| Day 14 | 0.70 | 0.3995 | 0.9505 | 3.0 (2.0) | 42.7 | 11.39 | 0.0399 | 0.0950 |
| 20 mg QD | | | | | | | | |
| Day 1 | 1.06 | 1.1123 | 2.1816 | 3.2 (2.6) | 29.2 | 10.00 | 0.0556 | 0.1091 |
| Day 14 | 0.89 | 0.9342 | 2.1125 | 4.7 (3.8) | 33.3 | 10.01 | 0.0467 | 0.1056 |
| 30 mg QD | | | | | | | | |
| Day 1 | 0.72 | 1.1192 | 2.5469 | 9.2 (4.6) | 75.0 | 12.37 | 0.0373 | 0.0849 |
| Day 14 | 0.89 | 1.2835 | 2.5681 | 6.7 (5.7) | 62.7 | 12.19 | 0.0428 | 0.0856 |
| 40 mg QD | | | | | | | | |
| Day 1 | 1.44 | 1.5282 | 3.9770 | 4.2 (3.8) | 48.7 | 12.60 | 0.0382 | 0.0994 |
| Day 14 | 1.19 | 1.8221 | 4.2998 | 10.3 (6.3) | 49.5 | 10.63 | 0.0456 | 0.1075 |
| 50 mg QD | | | | | | | | |
| Day 1 | 0.78 | 1.9697 | 4.4073 | 5.0 (4.5) | 43.2 | 12.38 | 0.0394 | 0.0881 |
| Day 14 | 1.14 | 1.7917 | 4.3785 | 10.1 (6.7) | 59.1 | 12.30 | 0.0358 | 0.0876 |
| 70 mg QD | | | | | | | | |
| Day 1 | 1.00 | 3.0819 | 6.9335 | 5.0 (4.7) | 41.6 | 11.21 | 0.0440 | 0.0990 |
| Day 14 | 1.10 | 2.6899 | 6.9489 | 12.5 (8.5) | 54.1 | 10.95 | 0.0384 | 0.0993 |
| 90 mg QD | | | | | | | | |
| Day 1 | 0.95 | 3.4806 | 9.0977 | 9.3 (6.8) | 56.7 | 11.68 | 0.0387 | 0.1010 |
| Day 14 | 0.95 | 4.0589 | 9.6467 | 14.6 (10.0) | 63.7 | 11.17 | 0.0451 | 0.1072 |
| 120 mg QD | | | | | | | | |
| Day 1 | 1.00 | 4.4720 | 11.3131 | 11.4 (9.1) | 57.8 | 11.09 | 0.0373 | 0.0943 |
| Day 14 | 1.11 | 5.3076 | 11.9599 | 18.2 (11.9) | 55.1 | 10.47 | 0.0442 | 0.0997 |
| 160 mg QD | | | | | | | | |
| Day 1 | 0.75 | 7.2978 | 20.7463 | 10.7 (9.8) | 40.7 | 8.22 | 0.0456 | 0.1297 |
| Day 14 | 0.80 | 8.7711 | 22.2821 | 11.8 (9.5) | 36.1 | 7.82 | 0.0548 | 0.1393 |
| 180 mg QD | | | | | | | | |
| Day 1 | 1.07 | 8.3986 | 25.5887 | 23.6 (11.0) | 54.6 | 7.75 | 0.0467 | 0.1422 |
| Day 14 | 1.00 | 8.0488 | 23.9545 | 20.8 (15.8) | 45.6 | 8.07 | 0.0447 | 0.1331 |
| 240 mg QD | | | | | | | | |
| Day 1 | 1.06 | 8.3858 | 28.2692 | 12.7 (10.2) | 54.6 | 9.53 | 0.0349 | 0.1178 |
| Day 14 | 0.94 | 11.2630 | 34.9763 | 9.9 (8.1) | 31.3 | 7.28 | 0.0469 | 0.1457 |
| 30 mg BID | | | | | | | | |
| Day 1 | 0.90 | 1.3091 | 2.8169 | 4.0 (3.8) | 34.4 | 11.30 | 0.0436 | 0.0939 |
| Day 14 (AM) | 0.70 | 1.4882 | 2.9146 | 4.9 (4.8) | 41.1 | 10.81 | 0.0496 | 0.0972 |
| Day 14 (PM) | 1.75 | 0.8986 | 3.3083 | 11.1 (5.8) | 61.0 | 9.88 | 0.0300 | 0.1103 |

$^a$AUC refers to AUC$_\infty$, AUC$_{24}$, and AUC$_{12}$ for Day 1 (QD & BID), Day 14 (QD), and Day 14 (BID), respectively.
$^b$Arithmetic Mean (Harmonic Mean)

$$\% \text{ Inhibition of } XOD = 100 \frac{C \cdot f_u}{C \cdot f_u + K_i} \quad \text{Equation 1}$$

where C=plasma concentration of febuxostat in plasma, $f_u$=the free fraction of febuxostat in plasma and $K_i$=the xanthine oxidase inhibitory constant of febuxostat.

The plasma concentration of febuxostat can be determined using a validated high performance liquid chromatography with fluorescence detection (See *Biopharmaceutics Coordinating Committee in the Center for Drug Evaluation and Research* (CDER). *Guidance for industry: bioanalytical method validation*. May 2001 and Mayer, M. et al., *American Journal of Therapeutics*, 12:22-34 (2005), herein each incorporated by reference). The lower limit of quantitation with a 0.5 mL plasma sample was 0.01 μg/mL for febuxostat.

The $f_u$ can be determined using the in-vitro binding of $^{14}C$ febuxostat at a nominal concentration of 1 μg/mL using an equilibrium dialysis technique, which is well known in the art. For example, the percent $f_u$ for febuxostat has been calculated to be 0.9±0.2 in normal patients and 1.2±0.2 in patients with severe renal impairment (See Mayer, M. et al., *American Journal of Therapeutics*, 12:22-34 (2005), herein incorporated by reference). In another study with a larger number of subjects, the percent free fraction of febuxostat in plasma was calculated to be 0.7±0.1 in male, female, younger and an elderly group of subjects (See Khosravan R., et al, *Clinic. Pharmacology & Therapeutics*, P50 (2005), herein incorporated by reference).

The $K_i$ for febuxostat has been determined using a xanthine oxidase assay such as that described in Osada Y., et al., *European J. Pharmacology*, 241:183-188 (1993), herein incorporated by reference. More specifically, the $K_i$ for febuxostat has been determined to be 0.7 nM and 0.6 nM, respectively (See, Osada Y., et al., *European J. Pharmacology*, 241:183-188 (1993) and Takano, Y., et al., *Life Sciences*, 76:1835-1847 (2005)). The $K_i$ for febuxostat is known in the art to be 0.6 nM (See, Takano, Y., et al., *Life Sciences*, 76:1835-1847 (2005), herein incorporated by reference).

Additionally, concentrations of febuxostat that exhibited 50%, 60%, 70%, 80%, 90%, 95%, and 99% inhibition of xanthine oxidase activity were calculated using the below Equation 2 (based on the calculation made above using Equation 1). The result of this calculation for all dosage regimens is listed below in Table 2.

$$C = \frac{\% \text{ Inhibition of } XOD \cdot K_i}{(100 - \% \text{ Inhibition of } XOD) \cdot f_u} \quad \text{Equation 2}$$

where C=plasma concentration of febuxostat in plasma, $f_u$=the free fraction of febuxostat in plasma and $K_i$=the xanthine oxidase inhibitory constant of febuxostat.

TABLE 2

Percentage Inhibition Following Administration of IR Formulations

| Dosing Regimen | Time Post Dose | | | |
|---|---|---|---|---|
| | 8 hours | 12 hours | 16 hours | 24 hours |
| 10 mgQD | 43.6 | 27.3 | 0 | 0 |
| 20 mgQD | 55.9 | 54.0 | 42.8 | 0 |
| 30 mgQD | 62.3 | 52.5 | 37.1 | 35.9 |
| 40 mgQD | 69.8 | 55.9 | 43.3 | 36.2 |
| 50 mgQD | 77.9 | 64.9 | 49.1 | 38.5 |
| 70 mgQD | 81.2 | 66.3 | 56.0 | 35.3 |
| 80 mgQD* | 82.7 | 71.9 | 60.8 | 37.0 |
| 90 mgQD | 85.6 | 77.7 | 68.1 | 50.3 |
| 120 mgQD | 89.0 | 82.6 | 75.8 | 60.5 |
| 160 mgQD | 93.9 | 90.9 | 81.4 | 67.6 |
| 180 mgQD | 94.7 | 91.7 | 81.5 | 68.4 |
| 240 mgQD | 95.7 | 91.4 | 86.5 | 72.4 |

*The 80 mg data was the result of simulated data used to calculate a simulated percentage inhibition As shown in Table 2, even when subjects received high doses of febuxostat (120 mg), at least 80% of inhibition of the xanthine oxidase enzyme was not provided for greater than sixteen (16) hours. Additionally, other studies involving 120 mg immediate release dosage forms of febuxostat demonstrated that such dosage forms provide a $C_{max}$ of about 3.9 and about 4.2 μg/mL and exhibited at least 80% inhibition of xanthine oxidase for about fourteen (14) hours. Further studies involving 240 mg immediate release dosage forms of febuxostat demonstrated that such dosage forms provide a $C_{max}$ of 10.2 μg/mL and exhibit at least 80% inhibition of xanthine oxidase for about 22 hours. Thereupon, in view of these results, the present inventors conceived of the modified release dosage forms of the present disclosure. These dosage forms exhibit high levels (at least 80%) inhibition of xanthine oxidase for a period of greater than sixteen (16) hours while not compromising patient compliance. The dosage forms of the present disclosure maintain high levels of inhibition of the xanthine oxidase enzyme at similar or lower total plasma exposure levels compared to high doses of febuxostat (namely, 120 mg and 240 mg QD).

Example 2: Estimated Plasma Profiles for Extended Release Febuxostat Formulations In view of the pharmacokinetic data pertaining to immediate release febuxostat formulations included in Example 1, the inventors developed estimated plasma profiles for various extended release formulations. Specifically, the inventors developed estimated plasma profiles for three types of formulations: extended release formulations, two-pulse formulations, and three-pulse formulations. The plasma profile information for the extended release formulations is based on a formulation with a polymeric component that provides febuxostat release at a constant rate over time, and may incorporate technology such as a matrix formulation. The estimated two-pulse formulation data is based on a febuxostat formulation having immediate release beads and beads that release febuxostat after approximately 5 hours. The estimated three-pulse formulation data is based on a febuxostat formulation having immediate release beads, beads that release febuxostat after approximately 5 hours, and beads that release febuxostat after approximately 10 hours. The estimated plasma profiles for the various formulations are found in Table 3. It should be noted that the plasma profile information pertaining to the immediate release formulations found in Table 3 represent actual data obtained in clinical testing.

TABLE 3

Estimated Plasma Profiles for Febuxostat Extended Release Formulations

| For-mulation | Dosing Regimen | Tmax (h) | Cmax (µg/mL) | Cmin (µg/mL) | AUC∞ (µg · h/mL) | Duration Time Conc. >0.1 µg/mL (hours) |
|---|---|---|---|---|---|---|
| IR* | 80 QD | 0.5 | 3.06 | 0.0159 | 7.99 | 8 |
| SR | 80 QD | 2.5 | 0.99 | 0.020 | 7.32 | 13.75 |
| 2PS-5 h | 80 QD | 5.75 | 1.69 | 0.025 | 7.46 | 15 |
| 3PS-5 h | 80 QD | 5.5 | 0.77 | 0.028 | 5.95 | 17.25 |

*The plasma profiles for the immediate release formulations represent actual data, and are not estimated values Example 3: Bioavailability of Febuxostat Released in Various Locations of the Gastrointestinal Tract The inventors tested the relative bioavailability of 80 mg of febuxostat released in the proximal small intestine, the distal small intestine, and the colon of 12 healthy male subjects, as compared to the bioavailability of an immediate release dosage form.

The subjects were randomly assigned in equal numbers to one of four regimen sequences, as set forth in Table 4. Subjects all received regimens in a crossover fashion according to a randomization schedule. Extra periods (up to 2 per subject) were added where subject dose release issues required repeating a regimen. There was a washout interval of at least 7 days between the dose in a period and the next dose in the subsequent period.

TABLE 4

Subjects and Regimen Schedules for Febuxostat administration

| Sequence | # Subjects | Period 1 | Period 2 | Period 3 | Period 4 |
|---|---|---|---|---|---|
| 1 | 3 | Regimen A | Regimen B | Regimen C | Regimen D |
| 2 | 3 | Regimen B | Regimen A | Regimen D | Regimen C |
| 3 | 3 | Regimen C | Regimen D | Regimen A | Regimen B |
| 4 | 3 | Regimen D | Regimen C | Regimen B | Regimen A |

Regimen A: Febuxostat 80 mg immediate release tablet (reference)
Regimen B: InteliSite capsule containing 80 mg of febuxostat drug substance released in the proximal small intestine
Regimen C: InteliSite capsule containing 80 mg of febuxostat drug substance released in the distal small intestine
Regimen D: InteliSite capsule containing 80 mg of febuxostat drug substance released in the colon Blood samples were obtained prior to dosing (0 hour) on Day 1 of each period, before the investigational product was released from the InteliSite capsule (0 hour preactivation) for Regimens B, C, and D and at 0.25, 0.5, 1, 1.5, 2, 3, 4, 6, 8, 10, 12, 16, 24, 30, and 36 hours after tablet dosing or release of febuxostat in the selected segment of the gastrointestinal tract. Plasma concentrations of febuxostat were determined from EDTA-treated samples using a validated liquid chromatography assay with mass spectrometric detection using positive ion electrospray ionization at PPD (Richmond, Va.). The method utilizes protein precipitation with acetonitrile of a 100 µL aliquot of plasma, with a lower limit of detection of 10.0 ng/mL.

Pharmacokinetic parameters for febuxostat were estimated using standard noncompartmental methods. Calculations were performed using the WinNonlin Pro Version 5.2 (Mountain View, Calif., USA). The descriptive statistics for pharmacokinetic parameter estimates were computed. Analyses of variance (ANOVA) were performed on febuxostat $T_{max}$ and the natural logarithms of $C_{max}$, AUC (0-tlqc), and AUC(0-inf) with factors for sequence, subject nested within sequence, period, and regimen. The effect of the release in the proximal small intestine, the distal small intestine, and the colon on the bioavailability of febuxostat was assessed via point estimates and 90% confidence intervals for the ratio of the central values for febuxostat $C_{max}$ and AUCs of Regimen B to Regimen A, Regimen C to Regimen A, and Regimen D to Regimen A, respectively. The subjects who had improper capsule release were allowed to repeat up to two extra periods after their scheduled sequence had ended. For ANOVA purposes, the missing or incomplete data from the periods with improper capsule release was replaced by the data from the corresponding repeated periods using the originally planned period for that regimen.

Figure 1:
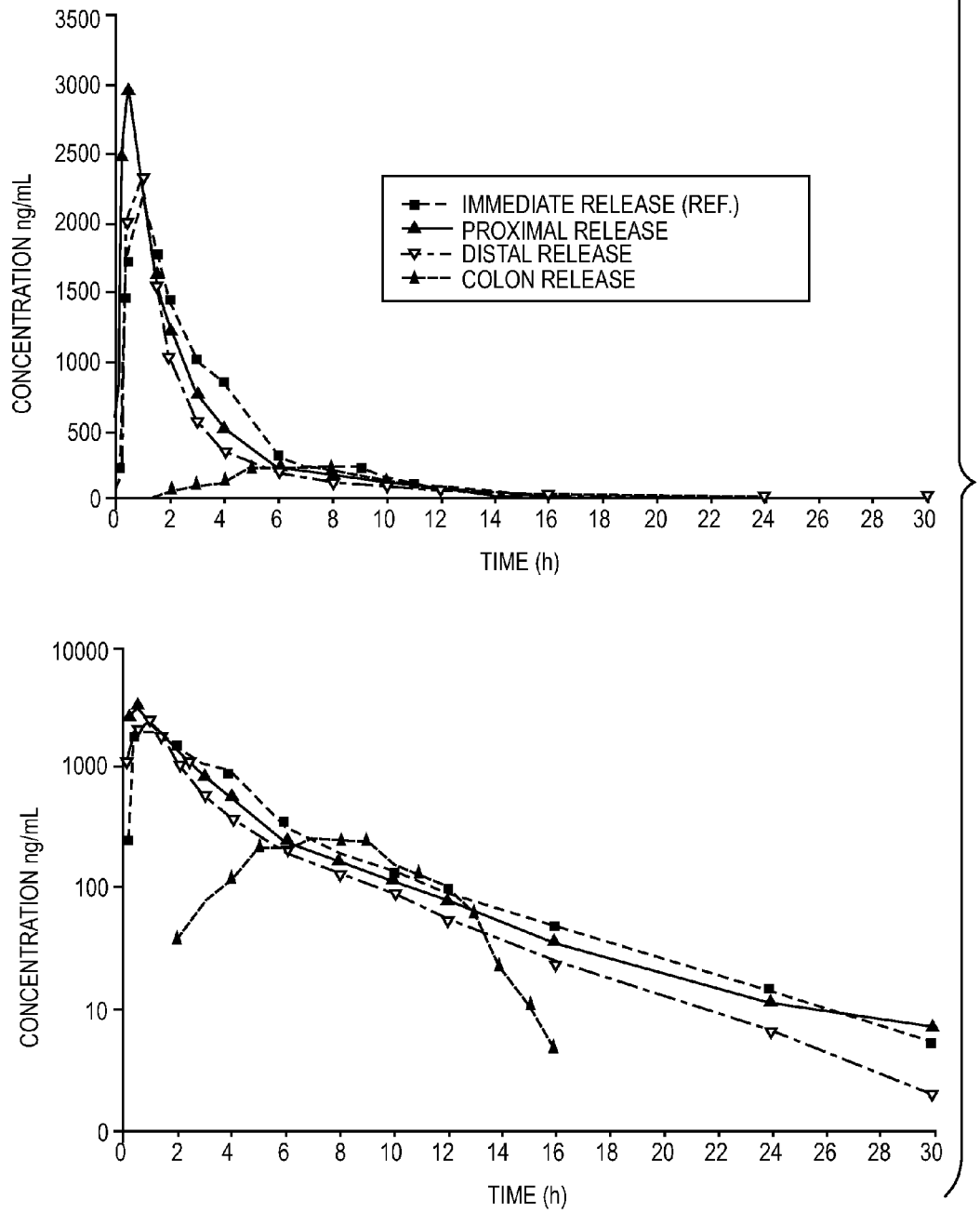
FIG. 1 shows the mean febuxostat plasma concentration-time profile for multiple 80 mg febuxostat formulations designed to release febuxostat in different portions of the gastrointestinal tract. Specifically.

The mean plasma febuxostat concentration-time profiles (linear and log-linear formats) for each regimen and site of absorption are depicted in FIG. 1. The summary of the mean pharmacokinetic parameter estimates for febuxostat following a single dose of febuxostat 80 mg for all four periods are displayed in Table 5. All febuxostat plasma concentrations from each subject were used for the pharmacokinetic parameter estimations; however, Subject 017-JDF (randomization number 112) had considerably less plasma exposure ($C_{max}$ and AUC) because of an apparent delayed (approximately 3 hours) release of drug product into the distal portion of the small intestine (Regimen C) when compared to all others. Subject 017-JDF distal intestinal release afforded a febuxostat $C_{max}$ value that was 5-13%, and an AUC value that was 12-28% that of all other distal releases. Therefore, data from the distal intestinal release for this subject was not included in the statistical analysis.

TABLE 5

Mean Pharmacokinetic Parameter Estimates for Febuxostat Following a Single Dose of Febuxostat 80 mg

| | Tmax (h) | Cmax (ng/mL) | AUC(0-tlqc) (ng · h/mL) | AUC(0-inf) (ng · h/mL) |
|---|---|---|---|---|
| Reference 80 mg Febuxostat Immediate Release (Regimen A) | | | | |
| N | 12 | 12 | 12 | 12 |
| Mean | 1.42 | 2650.83 | 7944.75 | 8051.70 |
| SD | 1.08 | 762.84 | 3265.12 | 3277.36 |
| Min | 0.50 | 1610.00 | 4394.53 | 4494.66 |
| Max | 4.00 | 4550.00 | 13795.70 | 13873.87 |
| 80 mg Febuxostat Proximal Intestinal Release (Regimen B) | | | | |
| N | 12 | 12 | 12 | 12 |
| Mean | 0.50 | 3026.67 | 7600.62 | 7703.35 |
| SD | 0.18 | 1491.51 | 3039.19 | 3042.99 |
| Min | 0.25 | 1480.00 | 4441.30 | 4524.33 |
| Max | 1.00 | 6540.00 | 14797.40 | 14904.24 |
| 80 mg Febuxostat Distal Intestinal Release (Regimen C) | | | | |
| N | 12 | 12 | 12 | 12 |
| Mean | 0.73 | 2561.83 | 5964.61 | 6072.24 |
| SD | 0.29 | 1055.49 | 2352.75 | 2352.01 |
| Min | 0.25 | 212.00 | 1021.80 | 1182.78 |
| Max | 1.00 | 4400.00 | 9839.35 | 9967.74 |
| 80 mg Febuxostat Distal Intestinal Release without Subject 017 (Regimen C) | | | | |
| N | 11 | 11 | 11 | 11 |
| Mean | 0.77 | 2775.45 | 6413.95 | 6516.73 |
| SD | 0.26 | 789.36 | 1850.34 | 1864.71 |
| Min | 0.50 | 1660.00 | 4144.80 | 4218.01 |
| Max | 1.00 | 4400.00 | 9839.35 | 9967.74 |

TABLE 5-continued

Mean Pharmacokinetic Parameter Estimates for Febuxostat Following a Single Dose of Febuxostat 80 mg

| | Tmax (h) | Cmax (ng/mL) | AUC(0-tlqc) (ng · h/mL) | AUC(0-inf) (ng · h/mL) |
|---|---|---|---|---|
| 80 mg Febuxostat Colon Release (Regimen D) | | | | |
| N | 12 | 12 | 12 | 12 |
| Mean | 3.25 | 382.50 | 2761.97 | 2953.24 |
| SD | 1.91 | 173.04 | 1119.74 | 1094.88 |
| Min | 0.50 | 100.00 | 1299.93 | 1455.35 |
| Max | 6.00 | 630.00 | 5259.23 | 5411.25 |

Regimen A: 80 mg febuxostat immediate release reference.
Regimen B: 80 mg febuxostat proximal intestinal release.
Regimen C: 80 mg febuxostat distal intestinal release.
Regimen D: 80 mg febuxostat colon release.

Following administration of febuxostat 80 mg released in the proximal small intestine (Regimen B) or the distal small intestine (Regimen C), mean $T_{max}$ values were 65% and 49% shorter (46% with Subject 017-JDF excluded), respectively, when compared to that of the immediate release tablet (Regimen A). In the colon (Regimen D), mean $T_{max}$ was more than twice that of the immediate release tablet (Regimen A). When febuxostat was released in the proximal (Regimen B) or distal (Regimen C) small intestine (regardless of Subject 017-JDF), both mean $C_{max}$ values were approximately equal to the mean $C_{max}$ value obtained from the immediate release tablet (Regimen A); whereas, febuxostat mean $C_{max}$ value for the colon release (Regimen D) was 14% that of the mean $C_{max}$ value from the immediate release tablet (Regimen A). Mean febuxostat AUC values were generally similar after febuxostat release in the proximal (Regimen B) intestine and from the immediate release tablet (Regimen A); however, for the distal (Regimen C) release, mean AUC values were reduced to 75% (81% when excluding Subject 017-JDF) when compared to the immediate release tablet (Regimen A) mean AUC values. After febuxostat release in the colon (Regimen D), mean AUC values were approximately 35% of those AUC values from the immediate release tablet (Regimen A).

Statistical assessments on the bioavailability of febuxostat administered (Regimens, B, C, and D) relative to that febuxostat immediate release (Regimen A) was assessed via point estimates and 90% confidence intervals for the ratios of the central values for $C_{max}$, AUC(0-tlqc), and AUC(0-inf) and are summarized in Table 6 (excluding Subject 017-JDF distal intestinal release data).

TABLE 6

Statistical Assessment of the Bioavailability of Regimens B, C, and D, Compared to Regimen A

| Parameter | Point Estimate of the Relative Bioavailability | 90% Confidence Interval for the Point Estimate |
|---|---|---|
| Regimen B vs. Regimen A | | |
| $C_{max}$ | 1.0660 | (0.7988-1.4226) |
| AUC(0-tlqc) | 0.9663 | (0.7731-1.2078) |
| AUC(0-inf) | 0.9663 | (0.7839-1.1911) |
| Regimen C vs. Regimen A (Subject 017 Excluded) | | |
| $C_{max}$ | 1.0555 | (0.7810-1.4267) |
| AUC(0-tlqc) | 0.8405 | (0.6659-1.0609) |
| AUC(0-inf) | 0.8429 | (0.6776-1.0487) |
| Regimen D vs. Regimen A | | |
| $C_{max}$ | 0.1356 | (0.1015-0.1811) |
| AUC(0-tlqc) | 0.3475 | (0.2777-0.4347) |
| AUC(0-inf) | 0.3706 | (0.3004-0.4572) |

Regimen A: 80 mg febuxostat immediate release reference.
Regimen B: 80 mg febuxostat proximal intestinal release.
Regimen C: 80 mg febuxostat distal intestinal release.
Regimen D: 80 mg febuxostat colon release.

Based on the data from 12 subjects (11 for the distal intestinal release—Regimen C), the 90% confidence intervals for the ratios of the central values when febuxostat 80 mg was administered in the proximal small intestine, distal small intestine, or colon (Regimens B, C or D, respectively) relative to dosing as an immediate release tablet (Regimen A) were outside of the bioequivalence limit of 0.80 to 1.25 for febuxostat $C_{max}$, AUC(0-tlqc) or AUC(0-inf). The febuxostat $C_{max}$ central value for the proximal (B) and distal (Regimen C) release were approximately 7% and 6% greater, respectively, than the $C_{max}$ central value after an immediate release tablet (Regimen A). The AUC central values for the proximal release (Regimen B) or distal release (Regimen C) were reduced by about 3% and 16%, respectively, when compared to those after an immediate release tablet (Regimen A). The febuxostat $C_{max}$, AUC(0-tlqc) and AUC(0-inf) central values for the colon release (Regimen D) were respective 14%, 35%, and 37% of those values after an immediate release tablet (Regimen A).

Accordingly, it was observed that following single dose oral administrations of febuxostat 80 mg released in the proximal small intestine, distal small intestine or colon (Regimens B, C or D) in 12 healthy male subjects (excluding Subject 017-JDF for the distal intestinal release), the systemic exposure of febuxostat was not bioequivalent to that obtained after administration of the febuxostat 80 mg immediate release tablet (A).

Figure 2:
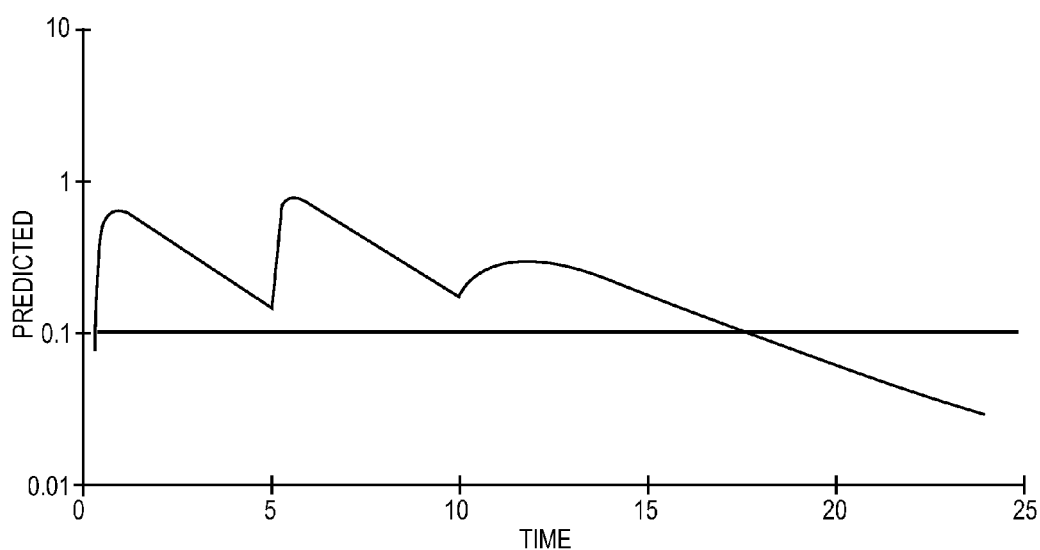
FIG. 2 shows the simulated febuxostat plasma concentration-time profile for a dosage form comprising an 80 mg 3-pulse febuxostat formulation, in which 30% of the febuxostat dose is released immediately (at time=0 hours) (i.e., pulse 1), 30% of the febuxostat dose is released after 5 hours (i.e., pulse 2), and 40% of the febuxostat formulation is released after 10 hours (i.e., pulse 3). The simulated data was calculated using parameters obtained from the site of absorption data referenced and discussed in Example 3.
Figure 3:
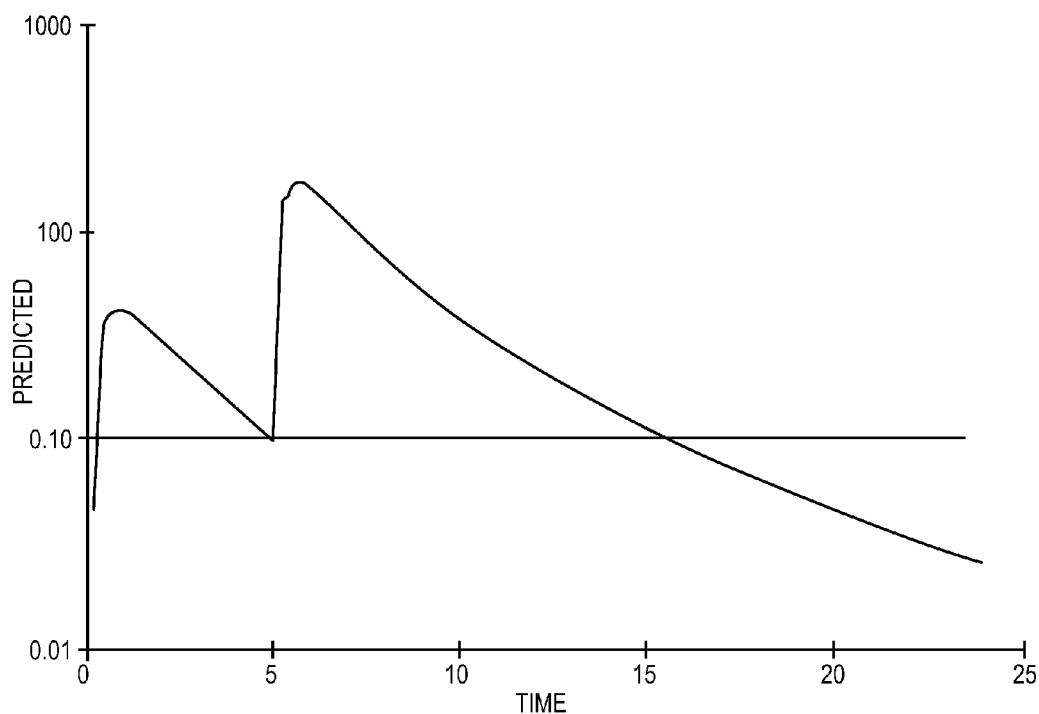
FIG. 3 shows the simulated febuxostat plasma concentration-time profile for a dosage form comprising an 80 mg 2-pulse febuxostat formulation, in which 20% of the febuxostat dose is released immediately (at time=0 hours) (i.e., pulse 1), 75% of the febuxostat dose is released after 5 hours, and 5% of the febuxostat formulation is released in the colon after 10 hours (the 5 hour and 10 hour releases collectively comprising pulse 2). The simulated data was calculated using parameters obtained from the site of absorption data referenced and discussed in Example 3.
Figure 4:
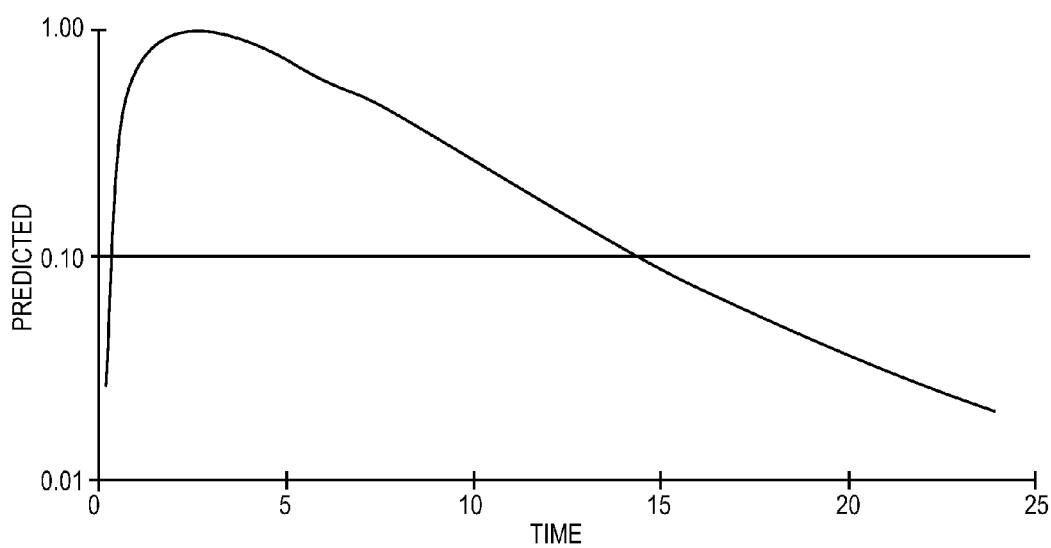
FIG. 4 shows the simulated febuxostat plasma concentration-time profile for a dosage form comprising an 80 mg extended release (ER) febuxostat formulation, in which 90% of the febuxostat dose is absorbed within 6 hours after dosing and the remaining 10% of the febuxostat dose is absorbed by the colon. The simulated data was calculated using parameters obtained from the site of absorption data referenced discussed in Example 3.

In addition, the inventors used the estimated data included in Tables 3, 4, and 5 to produce FIGS. 2-4. The inventors calculated estimated pharmacokinetic values for the absorption of febuxostat in various portions of the gastrointestinal tract (i.e., the stomach, proximal small intestine, distal small intestine, and the colon) and used these parameters to develop the log-linear graphs of the febuxostat plasma concentration over time for various dosage forms including an 80 mg 3-Pulse febuxostat formulation, an 80 mg 2-Pulse febuxostat formulation, and an 80 mg extended release (ER) febuxostat formulation.

Example 4: Modified Release Matrix Tablet Formulations

Figure 6:
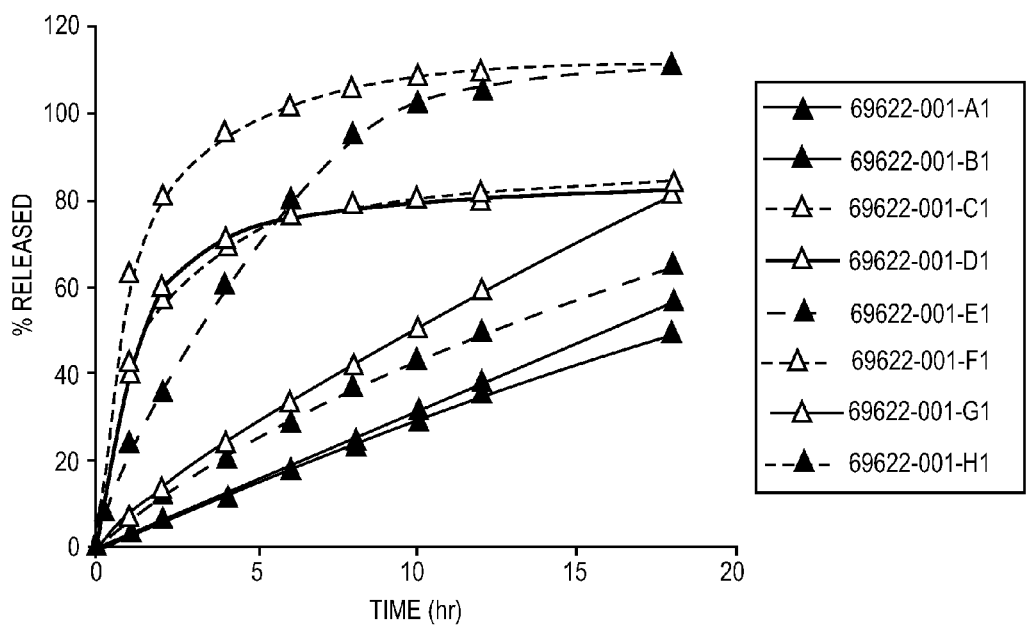
FIG. 6 illustrates the dissolution profiles for the eight distinct febuxostat modified release matrix tablet formulations over time. Specifically, the dissolution profiles were obtained by dissolving 50 mg modified release matrix tablet formulations a solution with a pH of 6.8 and in the presence of a 0.5 M phosphate buffer.

Modified release dosage forms that continuously release a xanthine oxidoreductase inhibitor, namely febuxostat, were prepared as matrix tablets containing the ingredients shown in FIG. 5 (the ingredients are shown in weight percentages). More specifically, the tablets were made by wet granulation using a Black & Decker Handy Chopper. The order in which the ingredients were added was not critical. A V-blender (Blend Master Lab, LC 9292659) was used to manufacture the final blend. Tablets were compressed on a carver press into a round shape by utilizing A-2308 tooling or oval shape (A-2253) device. For each of the dosage forms shown in FIG. 5, the drug release characteristics were determined and the resulting dissolution profiles are shown in FIG. 6. More specifically, with respect to the drug release characteristics and dissolution profiles, the oral dosage forms of febuxostat as described herein and containing the ingredients shown in FIG. 5 were evaluated for dissolution in 900 mL of 0.5 M phosphate buffer, pH 6.8, equilibrated at 37° C.±0.0.5° C. using a paddle method (USP Apparatus 2) at 50 rpm. Sample aliquots were taken at different time intervals and analyzed by high performance liquid chromatography. The compositions shown in FIG. 5 represent extended release febuxostat formulations.

Example 5: Triphasic Dosage Forms

Triphasic dosage forms that release a xanthine oxidoreductase inhibitor, such as febuxostat, can be prepared containing the ingredients (shown in weight percentages) listed in Table 7 below. These dosage forms comprise three (3) sets of granules. Granule A is designed to release the active agent in the stomach. Granule B is designed to release the active agent in the jejunum. Granule C is designed to release the active agent in the distal portion of the ileum and ascending colon.

More specifically, an active-agent loaded layer can be deposited by spraying an aqueous suspension of the active agent on to a number of neutral cores in order to obtain a plurality of drug granules. These drug granules are identified as "Granule A". A first portion of Granule A are removed and then coated with a methacrylic acid copolymer dispersion (such as Eudragit® L30D-55 or Eudragit® L100-55) that contains the active agent. The methacrylic acid copolymer dispersion can be applied to Granule A by spraying this aqueous dispersion directly onto Granule A. This methacrylic acid copolymer coated Granule A is now referred to as "Granule B." A second portion of Granule A is removed and coated with an aqueous dispersion which contains a mixture of methacrylic acid copolymer Type A (such as Eudragit® L100 and Eudragit® L12.5) and Type B (such as Eudragit® S100 and Eudragit® S12.5) and the active agent. This aqueous dispersion containing a mixture of methacrylic acid copolymer Type A and Type B can be applied to Granule A by spraying this mixture directly on to Granule A. This coated Granule A is now referred to as "Granule C." Next, remaining Granules A are then blended together with Granules B and C and filled in hard gelatin size 0 capsules.

TABLE 7

Febuxostat Modified Release Formulations

| Components | Granule A | Granule B | Granule C |
|---|---|---|---|
| Febuxostat | 20.0 | 20.0 | 80.0 |
| Microcrystalline cellulose sphere | 20.0 | 20.0 | 80.0 |
| Citric Acid | 7.0 | 7.0 | 15.0 |
| Sucrose | 25.0 | 25.0 | 50.0 |
| Low-Substituted Hydroxypropyl Cellulose | 5.0 | 5.0 | 20.0 |
| Eudragit L30D-55 | | 15.0 | |
| Polyethylene Glycol | | 2.0 | |
| Titanium Dioxide | | 1.0 | |
| Talc | | 2.0 | |
| Methacrylic Acid Copolymer Type B | | | 30.0 |
| Methacrylic Acid Copolymer Type A | | | 45.0 |
| Triethyl Citrate | | | 6 |

FIG. 2 shows the estimated plasma profile for a dosage form having three type of granules (3 Pulse), as shown in Table 7 above (incorporating all three granules). Specifically, FIG. 2 shows the estimated plasma febuxostat concentration-time profile following multiple dosings with a febuxostat controlled release (3-Bead, IR=24 mg, CR=24 mg released at 5.0 hours, CR=32 mg released at 10 hours) dosage form using the human pharmacokinetic data from Examples 1-3 and other studies and a two-compartmental model with first order absorption, and comparing the estimated plasma profile to an 80 mg immediate release formulation.

Example 6: Composition with 30% Immediate Release Febuxostat Beads and 70% Delayed Release 6.8 Febuxostat Beads The following composition was developed as a two pulse drug delivery system, wherein a single capsule included two types of febuxostat beads. The first pulse consists of 24 mg of immediate release febuxostat beads, wherein the febuxostat is released immediately after ingestion by the patient. The second pulse consists of 56 mg of delayed release 6.8 febuxostat beads, wherein the febuxostat is released when the beads are exposed to a pH level of at least 6.8. Tables 8 and 9 below list the components of the immediate release and delayed release 6.8 beads.

TABLE 8

Composition of Immediate Release Febuxostat Beads

| Ingredient | % Content |
|---|---|
| Febuxostat | 31.5 |
| Sugar sphere | 52.25 |
| Hypromellose | 16.25 |

TABLE 9

Composition of Delayed Release 6.8 Febuxostat Beads

| Ingredient | % Content |
|---|---|
| Febuxostat | 25.2 |
| Sugar sphere | 41.8 |
| Hypromellose | 13.0 |
| Methacrylic Acid Copolymer Type A | 4.5 |
| Methacrylic Acid Copolymer Type B | 13.7 |
| Triethyl citrate | 1.8 |

Example 7: Composition with 30% Immediate Release Febuxostat Beads, 30% Delayed Release 6.0 Febuxostat, and 40% Delayed Release Febuxostat Beads The following composition was developed as a three pulse drug delivery system, wherein a single capsule includes three types of febuxostat beads. The first pulse consists of 24 mg of immediate release febuxostat beads, wherein the febuxostat is released immediately after ingestion by the patient. The second pulse consists of 24 mg of delayed release 6.0 febuxostat beads, wherein the febuxostat is released when the beads are exposed to a pH level of at least 6.0. The third pulse consists of 42 mg of delayed release 6.8 febuxostat beads, wherein the febuxostat is released when the beads are exposed to a pH level of at least 6.8. The composition of the immediate release febuxostat beads and the delayed release 6.8 febuxostat beads are listed in Tables 8 and 9 above, respectively. The composition of the delayed release 6.0 beads is listed in Table 10 below.

TABLE 10

Composition of Delayed Release 6.0 Beads

| Ingredient | % Content |
|---|---|
| Febuxostat | 25.2 |
| Sugar sphere | 41.8 |
| Hypromellose | 13.0 |
| Methacrylic Acid Copolymer Type A | 18.0 |
| Triethyl citrate | 2.0 |

Example 8: Composition with 30% Immediate Release Febuxostat Beads and 70% Delayed-Controlled Release Febuxostat Beads The following composition was developed as a one pulse and delayed controlled release drug delivery system, wherein a single capsule includes two types of febuxostat beads. The one pulse consists of 24 mg of immediate release febuxostat beads, wherein the febuxostat is released immediately after ingestion by the patient. The remainder of the capsule comprises 56 mg of delayed controlled release beads, whereby the outermost delayed release layer becomes soluble at pH levels of 6.8 or greater and after the outermost layer has dissolved, the controlled release layer releases the febuxostat over a prolonged period of four to six hours. The composition of the immediate release febuxostat beads is listed in Table 8 above. The composition of the delayed-controlled release beads is listed in Table 11 below.

TABLE 11

Composition of Delayed-Controlled Release Febuxostat Beads

| Ingredient | % Content |
|---|---|
| Febuxostat | 21.4 |
| Sugar sphere | 35.5 |
| Hypromellose (in IR bead) | 11.1 |
| Surelease E-7-19010 (solid content) | 8.4 |
| Hypromellose (in CR coat) | 3.6 |
| Methacrylic Acid Copolymer Type A | 4.6 |
| Methacrylic Acid Copolymer Type B | 13.6 |
| Triethyl citrate | 1.8 |

Example 9: Composition with 20% Immediate Release Febuxostat Beads and 80% Controlled Release 10-12 Hour Beads The following composition was developed as a one pulse and controlled release drug delivery system, wherein a single capsule includes two types of febuxostat beads. The one pulse consists of 16 mg of immediate release febuxostat beads, wherein the febuxostat is released immediately after ingestion by the patient. The remainder of the capsule comprises 64 mg of controlled release febuxostat beads, whereby the febuxostat is released over a prolonged period of ten to twelve hours, beginning immediately after ingestion by the patient. The composition of the immediate release febuxostat beads is listed in Table 8 above. The composition of the controlled release 10-12 hour beads is listed in Table 12 below.

TABLE 12

Composition of Controlled Release 10-12 Hour Febuxostat Beads

| Ingredient | % Content |
|---|---|
| Febuxostat | 29.6 |
| Sugar sphere | 49.1 |
| Hypromellose (in IR bead) | 15.3 |
| Ethylcellulose | 3.6 |
| Hypromellose (in CR coat) | 2.4 |

Example 10: Febuxostat Modified Release Pharmacokinetic Data in Dogs

A study was performed in which eight distinct febuxostat formulations were administered to 6 dogs in a cross-over manner, and the plasma concentration (ng/ml) for the dog was measured at 0.25, 0.5, 1, 2, 3, 4, 5, 6, 8, 12, 18, and 24 hours post dosing. The test was performed to determine how the various formulations are absorbed in the dog model, and to determine plasma concentration profiles over time. Specifically, six male purebred beagle dogs were used in the study, wherein each of the eight test formulations was administered to the same set of six dogs. The dogs were individually housed and were not commingled for at least 24 hours after dose administration to allow monitoring of any test article-related effects. The test formulations were administered as an oral dosage form comprising either a capsule or tablet. The dogs were fasted overnight through approximately 4 hours post dose. Individual doses were calculated based on body weights taken on each day of dosing. A 6 μg/kg (0.048 mL/kg) intramuscular dose of pentagastrin was administered to each dog approximately 1 hour before test formulation administration. The mean plasma febuxostat concentration was measured by blood samples (approximately 2 mL), which were collected from a jugular vein via syringe and needle into tubes containing $K_2$ EDTA anticoagulant predose, at the time intervals listed above. Subsequently, the plasma samples were shipped off-site for analysis. The dog model was chosen because of prior experience with dosing delayed release beads for other drugs in dogs and the relationship of dog data with human data. In previous studies, a delay in $T_{max}$ for delayed release beads, with observed $T_{max}$ of about 2 hours in dogs had resulted in a delayed $T_{max}$ up to 8 hours in humans.

All eight febuxostat formulations comprised a total dose of 80 mg febuxostat, with different compositions of immediate release, delayed release, controlled release, and delayed-controlled release beads. The eight febuxostat formulations included:

(1) 80 mg of immediate release tablet (Reference formulation) (termed "Phase 1");
(2) 80 mg of delayed release 5.5 beads, having solubility at a pH level of at least 5.5 (termed "Phase 2");
(3) 24 mg of immediate release beads and 56 mg of delayed release pH 6.0 beads (termed "Phase 3");
(4) 24 mg of immediate release beads and 56 mg of delayed release pH 6.8 beads (termed "Phase 4");
(5) 24 mg of immediate release beads, 24 mg of delayed release pH 6.0 beads, and 32 mg of delayed release pH 6.8 beads (termed "Phase 5");
(6) 24 mg of immediate release beads and 56 mg of controlled release 4-6 hour beads (termed "Phase 6");
(7) 24 mg of immediate release beads and 56 mg of delayed-controlled release beads, wherein the delayed release layer is soluble at pH levels of at least 6.0, and the controlled release layer releases febuxostat over a period of 4-6 hours (termed "Phase 7"); and (8) 24 mg of immediate release beads and 56 mg of controlled release 10-12 hour beads (termed "Phase 8").

Figure 7:
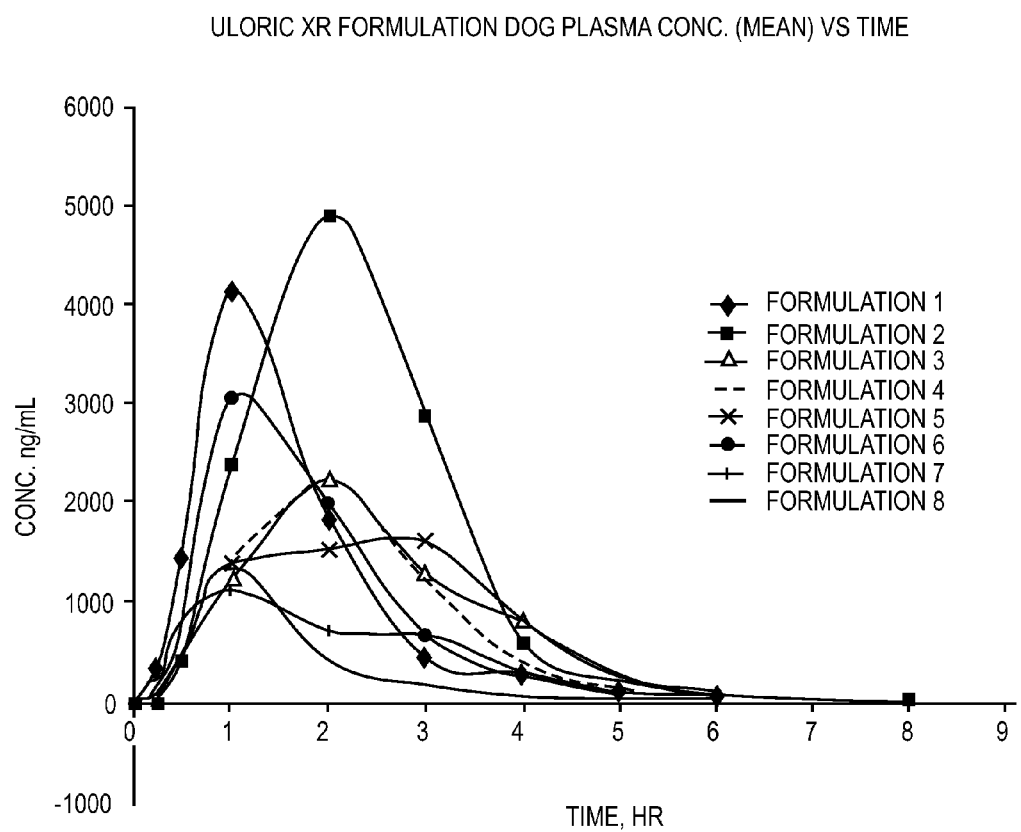
FIG. 7 illustrates the plasma febuxostat concentration-time profile for multiple modified release dosage forms, as described in Example 10, as tested in a dog model.

The plasma concentrations for the various dosage forms are shown in FIG. 7. Specifically, FIG. 7 illustrates a line graph for each formulation, disclosing the average febuxostat plasma concentration for each formulation over a six hour period after ingestion of the dosage forms. Although plasma samples were collected up to 24 hours, very low plasma concentrations were measured beyond 6-8 hours for most animals. This is consistent with literature reports, which suggest that the length of the gastro-intestinal tract in dogs is short compared to humans. Therefore, solid dosage forms transition quicker through the dog gastro-intestinal tract compared to humans. As a result, delayed release formulations designed to release febuxostat rapidly at specific pH triggers were absorbed much better compared to controlled release formulations which release drugs over a period of time.

In addition, a comparison for all eight formulations was performed, examining the mean plasma concentration of febuxostat for each Phase of the study at four hours, five hours, and six hours post dosing. The results were generally expected as the formulations comprising controlled release beads did not achieve febuxostat plasma concentrations significantly higher than the formulation comprising only immediate release beads. To reiterate, this result is expected as the gastrointestinal tract of dogs is much shorter than that of a human. This physiological consequence related to pharmacokinetic testing in dog models is discussed in more detail in the following articles: Stephen C. Sutton, *Companion animal physiology and dosage form performance*, ADVANCED DRUG DELIVERY REVIEWS, 2004, vol. 56, pp. 1383-1398; and Jennifer B. Dressman, *Comparison of Canine and Human Gastrointestinal Physiology*, PHARMACEUTICAL RESEARCH, 1986, vol. 3, no. 3, pp. 123-131. Accordingly, controlled release formulations that do not completely release the active component until 4-6 hours or 10-12 hours after ingestion may have passed through the majority, if not the entirety, of the dog's gastrointestinal tract by the time the active begins release, and high plasma concentrations cannot be achieved. A summary of these results is included in Table 13 below.

TABLE 13

Mean Plasma Concentrations for Febuxostat Formulations in Dogs

| Formulation Description | Mean Concentration (ng/ml) | | |
|---|---|---|---|
| | 4 hrs | 5 hrs | 6 hrs |
| Reference Tablet (Phase 1) | 289.8 | 73.2 | 53.8 |
| DR 5.5 (phase 2) | 632.6 | 207.8 | 79.1 |
| IR + DR 6.0 (Phase 3) | 785.2 | 283.7 | 105.3 |
| IR + DR 6.8 (Phase 4) | 448.3 | 151.3 | 69.3 |
| IR + DR 6.0 + DR 6.8 (Phase 5) | 827.9 | 249.1 | 104.9 |
| IR + CR Short (Phase 6) | 319.0 | 124.2 | 64.2 |
| IR + DCR 6.0 (Phase 7) | 329.8 | 95.5 | 44.3 |
| IR + CR Long (Phase 8) | 86.2 | 50.2 | 25.6 |

At four hours after dosing, the Phase 1 formulation, comprising 80 mg of immediate release beads, had a mean plasma concentration of 289.8 ng/ml. This value was significantly lower than the mean plasma concentrations for the dosage forms incorporating delayed release beads, as the Phase 2, Phase 3, Phase 4, and Phase 5 formulations showed mean concentrations of 632.6 ng/ml, 785.2 ng/ml, 448.3 ng/ml, and 827.9 ng/ml, respectively. The dog gastrointestinal pH levels are similar to those found in a human, so the delayed release beads were not affected by the length of the dog gastrointestinal tract, as seen with the controlled release beads. The dosage forms incorporating a combination of immediate release beads and controlled release beads generally experienced mean plasma concentrations similar to Phase 1, as expected. Phase 6, Phase 7, and Phase 8 formulations saw mean plasma concentrations of 319.0 ng/ml, 329.8 ng/ml, and 86.2 ng/ml, respectively. In these cases it is likely that only small amounts of the febuxostat in the controlled release beads was released, as the plasma concentrations were dependent, at least in part, on the immediate release beads found in the Phase 6, Phase 7, and Phase 8 formulations.

Looking at the mean concentrations seen at 5 hours post dosing, the Phase 1 formulation had a mean plasma concentration of 73.2 ng/ml. In comparison, the delayed release formulations of Phase 2, Phase 3, Phase 4, and Phase 5 showed higher mean plasma concentrations of 207.8 ng/ml, 283.7 ng/ml, 151.3 ng/ml, and 249.1 ng/ml, respectively. The controlled release formulations of Phase 6, Phase 7, and Phase 8 showed mean plasma concentrations of 124.2 ng/ml, 95.5 ng/ml, and 50.2 ng/ml, respectively.

In addition, the mean plasma concentrations at 6 hours post dosing showed similar comparative data to the data at 4 hours and 5 hours post dosing. The Phase 1 Formulation had a mean plasma concentration of 53.8 ng/ml. Similar to the data at 4 and 5 hours, the delayed release formulations of Phase 2, Phase 3, Phase 4, and Phase 5 showed higher mean plasma concentrations of 79.1 ng/ml, 105.3 ng/ml, 69.3 ng/ml, and 104.9 ng/ml, respectively. The controlled release formulations of Phase 6, Phase 7, and Phase 8 showed mean plasma concentrations of 64.2 ng/ml, 44.3 ng/ml, and 25.6 ng/ml, respectively.

Thus, even though the collection of plasma concentrations in the dog model is inherently limited by the shorter length of the dog gastrointestinal tract compared to the human gastrointestinal tract, the results of the comparison support improved febuxostat plasma concentrations for modified release formulations compared to immediate release formulations. The delayed release formulations of Phase 2, Phase 3, Phase 4, and Phase 5 displayed higher mean plasma concentrations at 4, 5, and 6 hours post dosing for all formulations compared to the reference immediate release formulation. The controlled release formulations of Phase 6 and Phase 7 (both incorporating 4-6 hour controlled release beads) showed improved mean plasma concentrations at 4, 5 and 6 hours (with the exception of the mean concentration for Phase 7 at 6 hours), although not to the extent seen with the delayed release formulations. These results are likely due to the fact that the controlled release component for Phase 6 and 7 were designed to release the active over 4-6 hours, meaning that the formulations may have released only a portion of the febuxostat before the formulation passed through the entire length of the gastrointestinal tract. The controlled release formulation of Phase 8 (incorporating 10-12 hour controlled release beads) displayed the lowest mean plasma concentration, lower than the reference immediate release formulation. As discussed previously, this result is not unexpected, as it is likely that the controlled release 10-12 hours beads (comprising 70% of the formulation) released only a small portion of the febuxostat prior to passing through the dog's gastrointestinal tract.

Example 11: Results of a Phase 1, Single-Dose Study in Humans of Four Febuxostat Extended Release Formulations and One Immediate Release Febuxostat Formulation This examples describes the results of a phase 1, single-center, open-label, randomized, 5-way crossover study. Thirty-five adult male and female subjects aged 18 to 55 years, inclusive, in good health, were selected to participate in this study. Subjects were randomly assigned in equal numbers to 1 of 5 formulation sequence groups as shown in Table 14.

TABLE 14

| | | Formulation Sequence Groups | | | | |
|---|---|---|---|---|---|---|
| | Number of | | | Formulations | | |
| Sequence | Subjects | Period 1 | Period 2 | Period 3 | Period 4 | Period 5 |
| 1 | 7 | A | B | E | C | D |
| 2 | 7 | B | C | A | D | E |
| 3 | 7 | C | D | B | E | A |
| 4 | 7 | D | E | C | A | B |
| 5 | 7 | E | A | D | B | C |

Formulation A (reference): Febuxostat (Uloric ®) IR 80 mg tablet.
Formulation B (test): Two-pulsatile prototype (80 mg) febuxostat capsule (TMX-67 XR Formulation B).
Formulation C (test): Three-pulsatile prototype (80 mg) febuxostat capsule (TMX-67 XR Formulation C).
Formulation D (test): Combination of pulsatile and continuous release (80 mg) febuxostat capsule (TMX-67 Formulation D).
Formulation E (test): Continuous release (80 mg) prototype febuxostat capsule (TMX-67 XR Formulation E).

All subjects in the study received 5 febuxostat formulations (IR, 2-pulsatile, 3-pulsatile, combination of pulsatile and continuous release, and continuous release) in a crossover fashion, according to the randomization schedule. A schematic of the study design is shown in Table 15.

TABLE 15

| | | Schematic of Study Design | |
|---|---|---|---|
| Screening | Check-in | Treatment Period | Washout |
| Days −28 to −2 | Day −1 of each period | Febuxostat 80 mg QD on Day 1 of each period [1 of 5 different formulations (A-E) containing febuxostat 80 mg dose given in each period] Days 1-3 of each period ← Confinement to Unit → | At least 7 days between the dose received in one period and the dose in the subsequent period |

Pharmacokinetic Sample Collection

Blood samples (4 mL) for the determination of plasma febuxostat concentration were collected at designated time points for 48 hours following administration of febuxostat 80 mg in Periods 1 through 5. Febuxostat plasma concentrations were quantified using a validated liquid chromatography/tandem mass spectrometry (LC\MS\MS) assay.

Pharamcokinetic Results

Figure 8A:
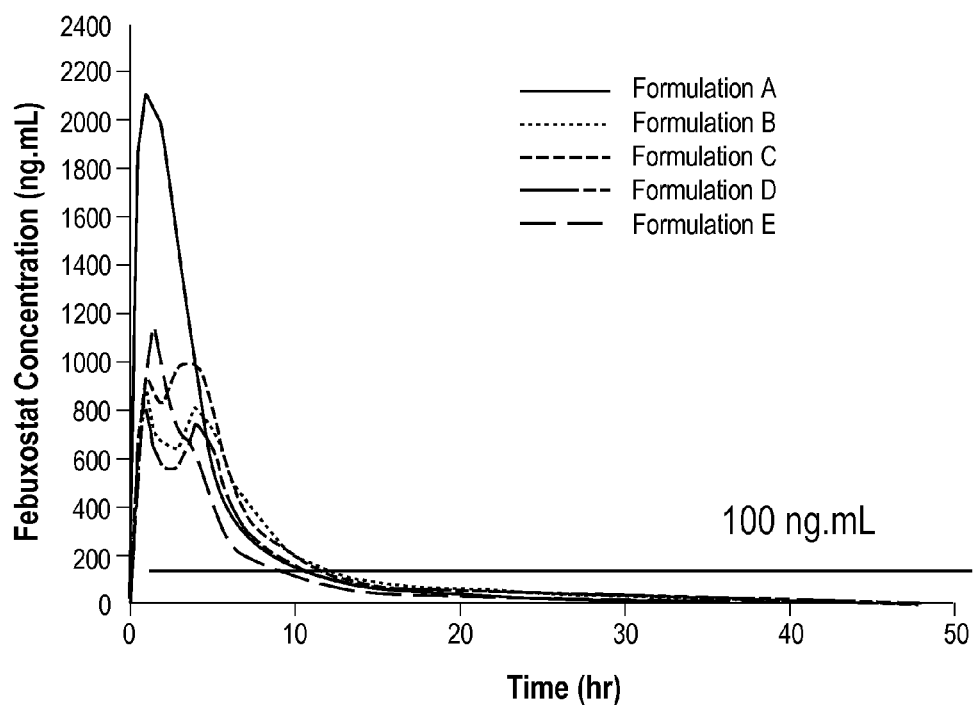
FIGS. 8A and 8B show the mean febuxostat plasma concentration-time profiles (Linear and cLogarithmic) following administration of a single 80 mg oral dose of 4 extended-release and IR febuxostat formulations as described in Example 11.
Figure 8B:
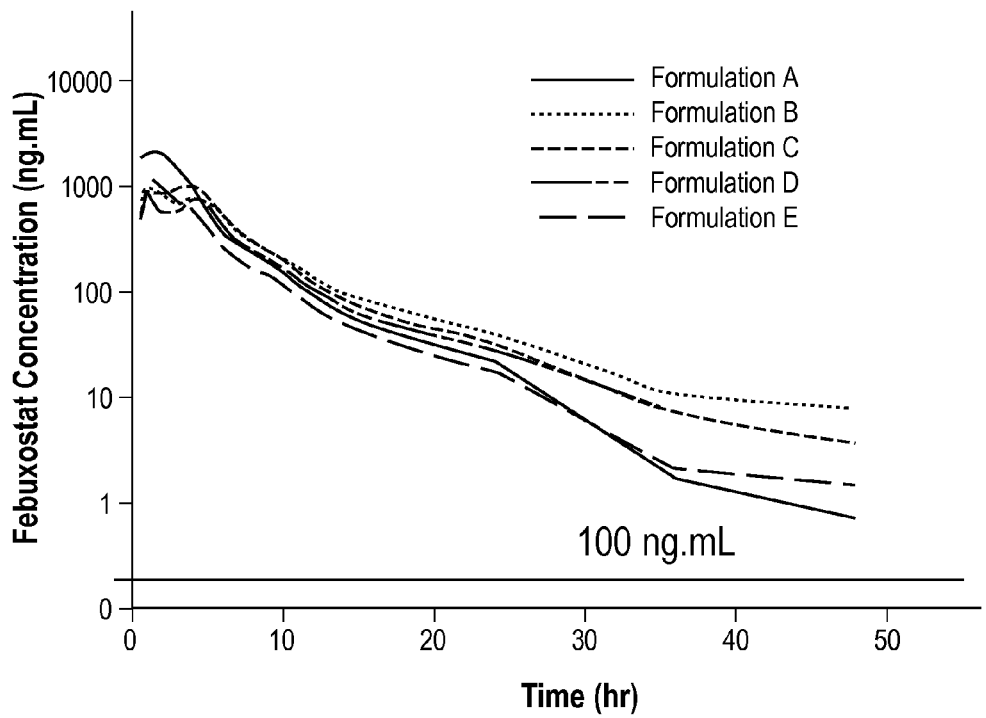

Summary of the mean pharmacokinetic parameters estimated for febuxostat following administration of five different 80 mg febuxostat formulations are summarized in Table 16. Mean plasma concentration-time profiles (linear and log-linear formats) for febuxostat following oral administration of a single 80 mg dose of febuxostat immediate release tablet and four extended release 80 mg capsule formulations are presented in FIGS. 8A and 8B. In all subjects, febuxostat was detected in plasma immediately with no absorption lag-time after oral dosing. The plasma febuxostat concentrations fell below the target concentration of 100 ng/mL at approximately 16 hours postdose following administration of extended release formulations (Formulations B-E).

TABLE 16

SUMMARY OF PLASMA PHARMACOKINETIC PARAMETERS
FOR FEBUXOSTAT FOLLOWING ADMINISTRATION OF SINGLE ORAL 80 MG
DOSE OF FEBUXOSTAT IMMEDIATE RELEASE TABLET AND FOUR 80 MG
EXTENDED RELEASE FORMULATIONS.

| | Tmax (a) (hr) | Cmax (ng/mL) | AUC (0-tlqc) (ng · hr/mL) | AUC (0-inf) (ng · hr/mL) | T1/2 (h) | CL/F (L/hr) | Vz/F (L) |
|---|---|---|---|---|---|---|---|
| IR Formulation A | | | | | | | |
| N | 35 | 35 | 35 | 33 | 33 | 33 | 33 |
| Mean | 1.0 | 3136.5 | 9495.8 | 9679.8 | 6.5 | 9.18 | 85.3 |
| SD | 0.5-3.0 | 1139.73 | 2769.23 | 2836.58 | 1.88 | 3.693 | 34.91 |
| % CV | — | 36 | 29 | 29 | 29 | 40 | 41 |
| Extended-Release Formulation B | | | | | | | |
| N | 34 | 34 | 34 | 27 | 27 | 27 | 27 |
| Mean | 3.0 | 1186.6 | 6749.3 | 7133.2 | 9.7 | 12.52 | 171.1 |
| SD | 0.5-6.0 | 407.31 | 2198.84 | 2497.88 | 3.65 | 4.333 | 78.2 |
| % CV | — | 34 | 33 | 35 | 38 | 35 | 46 |
| Extended-Release Formulation C | | | | | | | |
| N | 34 | 34 | 34 | 32 | 32 | 32 | 32 |
| Mean | 3.0 | 1292.2 | 7407.7 | 7726.7 | 9.0 | 11.49 | 146.6 |
| SD | 0.5-6.0 | 477.16 | 2556.45 | 2668.54 | 3.90 | 3.683 | 77.26 |
| % CV | — | 37 | 35 | 35 | 43 | 32 | 53 |
| Extended-Release Formulation D | | | | | | | |
| N | 35 | 35 | 35 | 31 | 31 | 31 | 31 |
| Mean | 1.0 | 1132.9 | 5832.0 | 6175.8 | 9.3 | 14.55 | 187.7 |
| SD | 0.5-6.0 | 424.30 | 2254.62 | 2357.24 | 3.78 | 4.844 | 82.04 |
| % CV | — | 37 | 39 | 38 | 41 | 33 | 44 |
| Extended-Release Formulation E | | | | | | | |
| N | 34 | 34 | 34 | 31 | 31 | 31 | 31 |
| Mean | 1.5 | 1246.6 | 5182.8 | 5334.2 | 7.6 | 17.05 | 169.1 |
| SD | 0.5-3.0 | 382.04 | 1911.91 | 2019.25 | 4.48 | 7.423 | 71.78 |
| % CV | — | 31 | 37 | 38 | 59 | 44 | 42 |

A = Febuxostat 80 mg IR Tablet
B = Febuxostat 80 mg extended release (Two pulsatile) capsule formulation
C = Febuxostat 80 mg extended release (Three pulsatile) capsule formulation
D = Febuxostat 80 mg extended release (Combination of pulsatile and Continuous) capsule formulation.
E = Febuxostat 80 mg extended release (Continuous Release) capsule formulation.

Example 12: Osmotic Tablets of Febuxostat

An osmotic tablet formulation was prepared using the swellable core technology. The tablet consists of a drug layer and a swellable polymer layer. This bilayer tablet is coated with a semipermeable membrane comprising cellulose acetate and polyethylene glycol. A hole was drilled on the top surface of the tablet by laser. The semipermeable membrane allows water to be absorbed into the tablet, however does not allow diffusion of any other material across the membrane. The swellable polymer layer swells as it absorbs water and pushes the drug out of the laser drilled orifice. Composition of the swellable polymer layer and thickness of the semipermeable membrane affect release of the drug. A tablet composition various tablet formulations is shown in Table 17 below. Formulation 1 is designed to give a longer duration of release since it contains lower amount of osmogen NaCl. Higher amount of osmogen in formulation 2 is expected to produce faster swelling of the polymer.

TABLE 17

| | Formulation 1 | | Formulation 2 | | Formulation 3 | |
|---|---|---|---|---|---|---|
| | Wt % of Layer | Weight per tab (mg) | Wt % of Layer | Weight per tab (mg) | Wt % of Layer | Weight per tab (mg) |
| Drug Layer | | 300 | | 300 | | 225 |
| Febuxostat | 26.7 | | 26.7 | | 35.6 | |
| PEO WSRN 10 | 72.8 | | 72.8 | | 63.9 | |
| Magnesium stearate | 0.5 | | 0.5 | | 0.5 | |
| Push layer | | 150 | | 150 | | 150 |
| PEO Coag | 64.5 | | 49.7 | | 64.5 | |
| NaCl | 34.8 | | 49.6 | | 34.8 | |
| Blue Lake #2 | 0.2 | | 0.2 | | 0.2 | |
| Magnesium stearate | 0.5 | | 0.5 | | 0.5 | |

Formulation 3 was coated with a semipermeable coat consisting of cellulose acetate (CA) and PEG 3350. The ratio of CA:PEG can be varied. For example, the ratio of CA:PEG can be in the range of 5:5 to 9:1. A CA:PEG ratio 6:4 results in faster release from the tablet compared to 7:3 ratio as seen in the FIG. 9. The amount of coating can be varied using routine techniques known in the art to adjust the dissolution profile as desired.

Osmotic tablets can be overcoated with an immediate release layer of the drug (febuxostat) to overcome time-lag as shown in FIG. 10. In this FIG. 10, a 60 mg tablet of febuxostat (formulation 2 above) is over-coated with 20 mg of febuxostat which is expected to be release immediately and thus become available for absorption.

Osmotic multiparticulates were prepared by layering febuxostat on microcrystalline cellulose spheres using routine techniques in the art. The drug layered beads are coated with a layer of disintegrant (such as croscarmellose sodium, crospovidone, etc.) and then overcoated with an aqueous dispersion of ethylcellulose. As seen in the FIG. 11, it is possible to obtain a multiparticulates of the desired release characteristics by varying the amount of ethylcellulose coating. Bursting multiparticulates can be combined uncoated beads to provide a 2-pulse formulation systems similar to other 2-pulse systems described herein.

One skilled in the art would readily appreciate that the present disclosure is well adapted to carry out the objects and obtain the ends and advantages mentioned, as well as those inherent therein. It will be readily apparent to one skilled in the art that varying substitutions and modifications may be made to the disclosure disclosed herein without departing from the scope and spirit of the disclosure. All patents and publications mentioned in the specification are indicative of the levels of those skilled in the art to which the disclosure pertains. All patents and publications are herein incorporated by reference to the same extent as if each individual publication was specifically and individually indicated to be incorporated by reference.

The disclosure illustratively described herein suitably may be practiced in the absence of any element or elements, limitation or limitations, which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

What is claimed is:

1. A modified release oral dosage form comprising:
   (a) an immediate release febuxostat component, the immediate release component comprising a first portion of febuxostat or pharmaceutically acceptable salt, and
   (b) a delayed release febuxostat component, the delayed release component comprising a second portion of febuxostat or pharmaceutically acceptable salt, and a coating layer which prevents release of the second portion of febuxostat,
   wherein the coating layer begins to dissolve at a pH of about 5.0 to 6.8,
   wherein febuxostat is the only active agent in the modified release oral dosage form,
   wherein the weight ratio of febuxostat or pharmaceutically acceptable salt in the immediate release febuxostat component to the febuxostat or pharmaceutically acceptable salt in the delayed release febuxostat component is about 1:9 to about 4:6 based on the weight of the febuxostat;
   wherein the modified release oral dosage form produces a median time to peak concentration ($T_{max}$) of febuxostat of equal or greater than about 3 hours in the fed state when administered to a subject, and maintains in the subject a plasma concentration of febuxostat or pharmaceutically acceptable salt thereof greater than about 0.1 µg/mL for a period of from about 5 hours to about 24 hours in a day and wherein the oral dosage form is selected from the group consisting of a pill, a tablet, and a capsule.

2. The oral dosage form of claim 1, wherein a single administration of a 80 mg of febuxostat in the oral dosage form to the subject inhibits greater than 80% of xanthine oxidase for a period of greater than 16 hours.

3. The oral dosage form of claim 1, wherein the ratio of febuxostat in the immediate release febuxostat component to the febuxostat in the delayed release febuxostat component is about 2:8 to about 4:6.

4. The oral dosage form of claim 1, wherein the delayed release febuxostat composition comprises a delayed release enteric polymer layer encapsulating the delayed release febuxostat composition containing febuxostat.

5. The oral dosage form of claim 1, wherein the coating layer begins to dissolve at a pH of about 5.5 to 6.8.

6. The oral dosage form of claim 1, wherein the coating layer allows for release of the febuxostat in an adult human subject's proximal intestine and distal intestine and minimizes febuxostat exposure in the colon.

7. The oral dosage form of claim 1, wherein a single administration of 80 mg of febuxostat in the oral dosage form of to an adult human subject produces in the subject a half-life of febuxostat at least about 1.5 times greater than a half-life of febuxostat from a single administration of 80 mg of febuxostat in an immediate release oral dosage form to an adult human subject.

8. The oral dosage form of claim 1, wherein the modified release oral dosage form produces in the subject a mean maximum plasma concentration ($C_{max}$) of febuxostat between about 0.8 µg/mL to about 1.7 µg/mL.

9. The oral dosage form of claim 1, wherein the coating layer is an enteric coating having a solubility at pH levels greater than or equal to 6.8.

10. The oral dosage form of claim 1, wherein the modified release oral dosage form produces the median time to peak concentration ($T_{max}$) of febuxostat of about 3 hours to about 9 hours.

11. A modified release oral dosage form comprising:
    (a) an immediate release febuxostat component, the immediate release component comprising a first portion of febuxostat or pharmaceutically acceptable salt, and
    (b) a delayed release febuxostat component, the delayed release component comprising a second portion of febuxostat or pharmaceutically acceptable salt, and a coating layer which prevents release of the second portion of febuxostat,
    wherein the coating layer allows for release of the febuxostat in an adult human subject's proximal intestine and distal intestine,
    wherein febuxostat is the only active agent in the modified release oral dosage form and the modified release oral dosage form contains 40 to 240 mg febuxostat, and
    wherein the weight ratio of febuxostat or pharmaceutically acceptable salt in the immediate release febuxostat component to the febuxostat or pharmaceutically acceptable salt in the delayed release febuxostat component is about 1:9 to about 4:6 based on the weight of the febuxostat, so that when ingested orally by a human subject, the dosage form induces inhibition greater than 80% of xanthine oxidase for a period greater than an immediate release composition comprising the same amount of febuxostat, and while maintaining a $C_{max}$ in the subject that is lower than a $C_{max}$ produced by the immediate release composition comprising the same amount of febuxostat, wherein the oral dosage form is selected from the group consisting of a pill, a tablet, and a capsule.

12. The oral dosage form of claim 11, wherein the ratio of febuxostat in the immediate release febuxostat component to the febuxostat in the delayed release febuxostat component is about 2:8 to about 4:6.

13. The oral dosage form of claim 11, wherein the delayed release febuxostat composition comprises a delayed release enteric polymer layer encapsulating the delayed release febuxostat composition containing febuxostat.

14. The oral dosage form of claim 11, wherein the coating layer begins to dissolve at a pH of about 5 to 6.8.

15. The oral dosage form of claim 11, wherein the coating layer minimizes febuxostat exposure in the colon.

16. The oral dosage form of claim 11, wherein a single administration of 80 mg of febuxostat in the oral dosage form of to an adult human subject produces in the subject a half-life of febuxostat at least about 1.5 times greater than a half-life of febuxostat from a single administration of 80 mg of febuxostat in an immediate release oral dosage form to an adult human subject.

17. The oral dosage form of claim 11, wherein the modified release oral dosage form produces in the subject a mean maximum plasma concentration ($C_{max}$) of febuxostat between about 0.8 µg/mL to about 1.7 µg/mL.

18. The oral dosage form of claim 17, wherein the modified release oral dosage form produces the median time to peak concentration ($T_{max}$) of febuxostat of about 3 hours to about 9 hours.

19. The oral dosage form of claim 11, wherein the coating layer is an enteric coating having a solubility at pH levels greater than or equal to 6.8.

20. The oral dosage form of claim 11, wherein the modified release oral dosage form contains 40 to 80 mg febuxostat.

* * * * *